(12) United States Patent
Morein et al.

(10) Patent No.: US 6,607,732 B2
(45) Date of Patent: *Aug. 19, 2003

(54) ISCOM OR ISCOM-MATRIX COMPRISING A MUCOUS TARGETTING SUBSTANCE AND AN ANTIGEN

(76) Inventors: Bror Morein, Ollonstigen 3, Vreta, Uppsala (SE), S-755 90; Karin Lovgren Bengtsson, Hojdvagen 30A, Uppsala (SE), S-756 53; Jill Ekstrom, Klev, Alunda (SE), S-740 50

( * ) Notice: Subject to any disclaimer, the term of this patent is extended or adjusted under 35 U.S.C. 154(b) by 0 days.

This patent is subject to a terminal disclaimer.

(21) Appl. No.: 09/137,236

(22) Filed: Aug. 20, 1998

(65) Prior Publication Data

US 2002/0131982 A1 Sep. 19, 2002

Related U.S. Application Data

(63) Continuation of application No. PCT/SE97/00289, filed on Feb. 20, 1997.

(30) Foreign Application Priority Data

Feb. 21, 1996 (SE) .............................................. 9600647

(51) Int. Cl.$^7$ .............................................. A61K 45/00
(52) U.S. Cl. .............................. 424/278.1; 424/204.1; 424/234.1; 424/265.1; 424/279.1; 424/282.1; 424/283.1
(58) Field of Search .......................... 424/204.1, 278.1, 424/279.1, 282.1, 283.1

(56) References Cited

U.S. PATENT DOCUMENTS 6,290,962 B1 * 9/2001 Michetti et al. .......... 424/185.1

OTHER PUBLICATIONS

Powell et al., Eds. Vaccine Design The Subunit and Adjuvant Approach, Plenum Press, New York 1995. p. 177.*
Powell et al., Eds. Vaccine Design The Subunit and Adjuvant Approach. Plenum Press, New York 1995. pp. 152–153 and 182.*
by K. Scheepers et al.,"Protection of mice against an influenza virus infection by oral vaccination with viral nucleoprotein incorporated into immunostimulating complexes", *Medical Microbiology and Immunology*, vol. 183, 1994, pp. 266–277.
by M. Hazama et al., "Intranasal immunization against herpes simplex virus infection by using a recombinant glycoprotein D fused with immunomodulating proteins, the B subunit of *Escherichia coli* heat–labile enterotoxin and interleukin–2", *Immunology*, vol. 78, 1993, pp. 643–648.
by C.R. Alving, et al., "Effectiveness of liposomes as potential carriers of vaccines: applications to cholera toxin and human malaria sporozoite antigen", *Vaccine*, vol. 4, 1986, pp. 166–172.
by J. Holmgren et al., "Chlolera toxin and cholera B subunit as oral–mucosal adjuvant and antigen vector systems", *Vaccine*, vol. 11, issue 12, 1993, pp. 1179–1183.
by J. Vadolas et al., "Intranasal immunization with liposomes induces strong mucosal immune responses in mice", *Eur. J. Immunol.*, vol. 25, 1995, pp. 969–975.
by N.M. Wassef et al., "Prostaglandin and Thromboxane in Liposomes: Suppression of the Primary Immune Response to Liposomal Antigens", *Biochemical and Biophysical Research Communications*, vol. 160, No. 2, 1989, pp. 565–572.
by A.J. Husband, "Novel vaccination strategies for the control of mucosal infection", *Vaccine*, vol. 11, 1993, pp. 107–111.
by F. Helling et al., "$G_{D3}$ Vaccines for Melanoma: Superior Immunogenicity of Keyhole Limpet Hemocyanin Conjugate Vaccines", *Cancer Research*, vol. 54, 1994, pp. 197–202.

* cited by examiner

*Primary Examiner*—Donna Wortman
(74) *Attorney, Agent, or Firm*—Young & Thompson

(57) ABSTRACT

An immunogenic complex includes at least one glycoside and at least one lipid. The complex further contains a) at least one mucosal surface targeting protein, protein derivative or carbohydrate that targets lymphatic tissue and induces an immune response when administered locally on mucous membranes; and b) at least one passenger immunogen that lacks tropism for mucous membranes.

**

ISCOM OR ISCOM-MATRIX COMPRISING A MUCOUS TARGETTING SUBSTANCE AND AN ANTIGEN

This is a continuation of International Application PCT/SE97/00289 filed Feb. 20, 1997, which designated the United States.

The present invention relates to Immunogenic complex in the form of ISCOM™ (complexes as described for example in U.S. Pat. No. 4,578,269) and/or ISCOM™ matrix (complexes as described for example in U.S. Pat. No. 5,679,354) and mucus targeting molecules for use for preparing vaccines and immune stimulating compositions for oral, nasal, urogenital and/or rectal administration.

Immunization strategies have been available for many years. However, there has been a remarkable lack of success in vaccination to control mucosal diseases. Earlier findings indicate that antigen presentation of non-replicating antigens via the mucosal surface is an inefficient means of immune response stimulation and that novel strategies are required in this route (Novel vaccination strategies for the control of mucosal infection, Alan J. Husband, Vaccine, Vol. 11, Issue 2, 107–112). Vaccination with living attenuated microorganisms has been the only possible way of protection against mucosal diseases.

It has now unexpectedly been shown that ISCOMs™ containing, and ISCOM™ matrix mixed with, mucosal targeting molecules or antigens give raise to high titers of antibodies when administered to mucosas. Moreover ISCOMs™, containing such mucosal targeting molecules together with antigens which do not readily immunize by the mucosal mode of administration (so called passenger antigens), give raise to an immune response even in several other mucosals remote from the site of administration.

The mucosal targeting molecules have the capacity to target the lymphatic system following mucosal administration. They may be antigens which assist passenger antigens in inducing immune response and often, they will also induce immune response to themselves. In a complex mixture of antigens, some may exhibit a capacity for being target molecules for passenger molecules as well as for themselves. The strategy of using a mixture of two or more components also involves the prospect of modulating the ensuing immune response to itself as well as to passenger antigens. The modulatory effect is particularly prominent in iscom formulations with targeting molecules exemplified by IgG2a enhancement, as well as the capacity for iscoms to enhance conversion of the mucosal antibody response to IgA in mucus which is best illustrated by the enhancing effect on the IgA response to CTB. ISCOM™-matrix simply added to other antigens and mixed as a separate entity has similar properties as well as but they are often less prominent.

BACKGROUND

Lipid-containing and quillaja saponin-containing structures such as ISCOMs™ (immunostimulating complexes) and ISCOM™-matrices have been reported to be effective carriers of pharmacologically and/or immunologically active substances or molecule complexes. See for example WO-A1-90/03184. In many cases, parenteral immunization of laboratory animals with structures incorporating different antigens has been demonstrated to give rise to a stronger immune response against the antigens at issue than that which is obtained after immunization with the corresponding antigen(s) in a free form.

ISCOMs™ are documented to be effective carriers in enhancing the immunogenicity of small and large molecules (antigens) using parenteral administration. It has been shown that iscoms with incorporated antigens, such as protein, according to EP 0 109 942, and ISCOMs™ that are carriers for small molecules, such as small antigens and oligopeptides, according to EP 0 180 564, effectively evoke immune response toward both large and small molecules.

It has also been shown that protein antigen, such as ovalbumin (OVA), in ISCOM™ is able to evoke immune response even after oral immunization that includes antibody formation, T-helper cells under MHC class-2 restriction and cytotoxic T-cells (CTL) (killer cells) under MHC class 1-restriction, but that several immunizations are required (and unrealistically high doses) (Morein, B., Lovgren, K., Ronnberg, B. Clin. Immunother. 3, 461–75, 1995). On the contrary, after giving large doses (hundreds or several hundreds of $\mu$g per dose of ovalbumin orally in free form, ie unincorporated in iscom), there is either no immune response or a low one. Free ovalbumin gives rise to tolerance and suppression to a subsequent parenteral immunization.

ISCOM™-matrices (and ISCOM™ have well-documented, built-in adjuvant activity that evokes antibody-mediated and cell-mediated immune response. Cell-mediated immune responses under both class 1 and class 2 MHC-restrictions are evoked by ISCOMs™.

In comparison to parenteral immunization, the immune response after oral and intranasal administration of ISCOMs™ has been low (Mowat et al, Immunology 72, 317–322 (1991); Mowat et al., Immunology, 80, 527 (1993)). Moreover, in applying intranasal and oral immunizations, certain antigens that are incorporated in ISCOM™, such as the g-protein of the rabies virus or gp 120/160 of HIV-1, have not evoked measurable immune response in the form of serum antibody response measured in ELISA. In all likelihood this is due to the fact that only a small number of the perorally or intranasally administered particles can penetrate the mucous layer, be absorbed by the intestinal epithelium barrier or M-cells of Peyers patches and there come in contact locally with the immune system.

Problems involving limited absorption and insufficient antigen presentation caused by the inability of antigens to penetrate the mucous barrier and target antigen presenting cells (APC), lymphatic tissue and/or the epithelium layer, eg Peyer's patches (PP) or Lamina propria (LP) in the intestines, or lymphatic tissues in the tonsil region in the pharynx or other mucous-coated surfaces. Mucosal immune response will generally only occur when mucosal administration is carried out locally. ISCOMs™, like other antigen-presented structures, have a limited ability to penetrate mucus, and, in varying degrees, a limited ability to bind and be absorbed by the epithelium, or to reach and be absorbed by M-cells in PP to thereafter be forwarded to antigen-presented cells (APC) and to stimulate lymphocyte populations. Even when administration is done into the nasal mucosa, the targeting and antigen uptake by APC and the induction of the immune response is insufficient when using current technology. CT and LT have been used as mucus targeting molecules but due to high toxicity those are not suitable for use in man and animals. The B-subunit of these toxins are not toxic but very much less effective and for that reason not practically suitable for prophylactic or clinical use. There is thus a need for better presentation systems for antigens that are intended for use in oral or nasal administration. An important reason why there is this need for better antigen-presenting systems that are effective in administration via mucosal membranes is that this kind of administration evokes a local immune response in the membranes.

Although it is known that common lymphatic systems exist where immunization e.g. in the gut will result in immune responses in remote mucosal surfaces via gut associated lymphatic tissue (GALT) or immunization in the respiratory tract with result in immune response in other mucosal surfaces via broncho-associated lymphatic tissue (BALT) these responses are generally low and mucus targeting molecules or antigen presenting systems promoting remote mucosal targeting is not particularly defined. A number of infections occur via mucosal membranes in places like the respiratory passages, the intestinal tracts or the genital tract, and a first immune defence barrier exists in the mucosal membranes. Moreover, both oral and nasal administrations in contrast to parenteral administration by injection have the advantage of not requiring medically-trained personnel.

SUMMARY OF THE INVENTION

The invention relates to Immunogenic complex in the form of ISCOM™ and/or ISCOM™ matrix and mucus targeting molecules for use for preparing vaccines and immune stimulating compositions for oral, nasal, urogenital and/or rectal administration.

It has been shown that by using immunoenhancing complexes chose from ISCOMs™ and ISCOM™ matrices contained at least one glycoside, at least one lipid of which one being cholesterol a) at least one mucus targeting molecule chosen from substances that target lymphatic tissue and thereby induce immune response in local mucosal membranes; and possibly b) at least one passenger antigen chosen from pharmacological immuno-affecting or enhancing or immunogenic substances that do not easily reach lymphatic tissue through mucous membranes, vaccines and immunostimulating agents can be prepared for oral, nasal, urogenital and/or rectal administration. This will provide antibodies against the passenger antigen in serum, local IgA immune response in secretions in the local membrane at the site of the administration and also in membranes in other places, particularly in the respiratory tract in the intestines and in the genital tract.

DETAILED DESCRIPTION

One aspect of the invention relates to the use of ISCOM™ complexes containing at least one mucus targeting molecules for preparing a vaccine or immune modulating composition directed against that molecule. The ISCOM™ may also contain at least one passenger antigen together with the mucus targeting molecule or molecules in order to give raise to an immune response against the targeting molecule(s) and the passenger antigen(s).

The invention also relates to the use of ISCOM™ matrices that are mixed with at least one mucus targeting molecule for preparing a vaccine or immune modulating composition directed against that molecule. The ISCOM™ matrices may also be mixed with at least one passenger antigen together with the mucus targeting molecule or molecules in order to give raise to an immune response against the targeting molecule(s) and the passenger antigen(s).

ISCOM™ contains at least on glycoside, at least one lipid and at least one type of antigenic substances, especially proteins and peptides. These complexes enhance the immunogenicity of the administered antigens and may contain one or more immunomodulating (adjuvant-active) substances as described in EP 0 109 942 B1, EP 0 242 380 B1 and EP 0 180 564 B1.

Because certain antigens do not require physical integration in the ISCOM™ particle, great advantages are also to be gained from local mucosal administration using ISCOM™-matrix mixed with passenger antigen in separate entities. Such antigen is exemplified by gB2 of Herpes simplex 2 virus, which induce immune response by mucosal administration but the immune response is considerably enhanced by both matrix and iscom.

Matrices contain at least on glycoside that is an adjuvant-active substance and at least one lipid. Matrices have an immunostimulating effect on administration together with antigenic substances, see EP 0 436 620 B1. The matrices may have various kinds of immunoactive, immunoenhancing components (see EP).

According to the invention, complexes may be composed of an ISCOM™ complex with a mucus targeting molecule and/or passenger molecule(s) (that are) integrated into the ISCOM™ complex or else tied to a ready-made iscom complex.

They may also be made up of ISCOM™ matrices to which the mucus targeting and passenger antigens can be chemically coupled or bound by hydrophobic interactions, making them ISCOM™ or ISCOM™ matrices that are separated entities mixed with the antigen formula.

According to the invention, these complexes can be used to prepare vaccines and immunostimulating agents for oral, nasal or rectal modes of administration, or other types of local mucosal administration. They induce immune response in other mucous membranes than the ones they are administrated in, such as the urogenitals, the intestines, the upper respiratory tracts and the lungs as well as circulating antibodies.

According to the invention, these complexes also modulate the immune response to encompass strong specific IgA in various mucosal secretions and to encompass an increased IgG2a response in serum indicating a participation of interferon-gamma and T-helper 1 response.

ISCOM™, like ISCOM™ matrices, can, according to the invention, modulate antibody-mediated immune responses and the cell-mediated immune response that differ from immunomodulation evoked by a parenteral mode of immunization. Local mucosal administration also gives rise to immune response against other antigens or antigen determinants. From this point of view, new possibilities arise to elicit immune response that is not recognizable in parenteral immunization, eg against carbohydrate structures.

It is also of interest to use them in the preparation of vaccines intended for immunotherapy or for the treatment of allergies e.g. by desensitation via immunotherapy. They are also useful in breaking tolerance to antigens induced by CTB or LTB or other tolerance conditions caused by local application.

Mucus targeting molecules and passenger antigens are derived from microorganisms such as bacteria, viruses or parasites, in particular those named in EP 0 109 942 B1.

Mucus targeting molecules are substances that target lymphatic tissue to induce immune response in local mucosal administration in various mucosal surfaces as well as systemic immune response. In particular, antigen substances such as proteins, peptides, carbohydrates are intended. The carbohydrates may be polysacharides, glucolipides or glucopeptides.

Mucus targeting molecules may be of bacterial or viral origin, such as the bacterial cholera toxin and its subunit B (CTB), or the heat-labile toxin i *E-coli* and its subunit B (LTB). Other examples are enveloped proteins from viruses or proteins from bacteria, which can penetrate the mucosal membranes and infect the respiratory passages, such as the influenza virus, respiratory syncytial virus (RSV), corona virus, herpes viruses, pox virus, membrane proteins from Mycoplasma and fimbriae from bacteria such as hexons and pentons from adenovirus, Norwalk virus, rotavirus, and enterovirus from the family of picornaviridae and astrovirus. Other examples of usable antigens are the enveloped proteins from viruses and bacteria that infect the intestines, such as influenza virus adenovirus, reoviruses, corona virus and fimbriae from *Excherichia coli* (K88, K99, K981-B), Shigella, Clamydia and membrane proteins from Mycoplasma.

Such microorganisms can be the measles, German measles and chicken pox viruses; *Mycoplasma pneumoniae, Mycoplasma mycoides, Chlamydia pneumoniae, Neisseria meningitidis, Neisseria gonorrhoea, Vibrio cholerae, Salmonella typhi, Streptococcus mutans, Helicobacter pylori, Streptococcus pyogenes, Corynebacterium diphtheriae, Mycobecterium tuberculosis, Yersinia pestis, Salmonella typhi, Borrelia burgdorferi, Plasmodium vivax, Plasmodium falciparium, Toxoplasma gondii, Trypanosoma cruzi Trypanosoma brucei, Gardia lambiia* and *Entamoeba histolytica*; and *Cryptococcus neoformans* and *Histoplasma capsulatum, Pneumococcus pneumonia, Haemophilus influenzae.*

Passenger antigens may be chosen either from the group of pharmacological antigen substances or from antigen substances that are relevant from immunization and that lack tropism for mucous membranes, i.e., less effectively penetrate mucous membranes, for instance gB and gD in various Herpes viruses including Herpes Simplex 1 and 2, bovine herpes virus 1, picorna virus, gp 120 and gp 160 in HIV-1 or the corresponding envelope protein in HIV-2, as well as from other retroviruses, hepadna viruses e.g. pox virus, adenoviruses, cardivirus, togavirus, flavavirus, irdiovirus, birnavirus, provovirus, popovavirus, picornavirus, calicivirus, astrovirus, arenavirus, bunyavirus, ortomyxovirus, paramyxovirus, G-protein from the rabies virus, or from bacteria such as salmonella, *E. coli*, Shigella, Chlamydia, ricketsia, bartonella or Mycoplasma. They may also be various recombinant products or synthetic antigens that lose or do not lose their capacity after cloning or that increase their capacity to induce immune response via incorporation in iscom with mucus targeting molecules or with matrices since they are mucus targeting to the lymphatic tissue when applied on mucous membranes.

In those cases where the complexes are ISCOMs™, they may be prepared as described in the European patent EP 0 109 942 B1. Here, viruses, mycoplasma, bacteria, parasites and animal cells are mixed, containing antigens or antigenic determinants, particularly proteins or peptides or isolated molecules that have hydrophobic or amphiphilic regions, are mixed with one or more solubilizing agents, after which the antigens or determinants are separated from the solubilizing agent in the present of, or is separated from the solubilizing agent and is directly transferred to a glycoside solution, containing cholesterol, phospholipids and one or more glycosides with hydrophobic or hydrophilic domains in a concentration of at least a minimum of the critical micellar concentration, after which a protein complex is formed and then isolated and purified.

One can start from whole microorganisms containing passenger, antigen and/or mucus targeting molecules, whereby mucus targeting molecules or passenger antigens that are either more or less purely prepared, synthetic or prepared using a hybrid-DNA technique may be added. The additive may be put in at any partial stage, as is explained in EP 0 109 942 B1, especially on pp. 4–8. The preferred procedure is to put in the additive before adding the lipids and glycosides.

Furthermore, you can use a base consisting of mucus targeting molecules or passenger antigens that are more or less purified, synthetisized chemically or prepared using a hybrid-DNA technique according to EP 0 109 942 B1 as on pp. 4–8. In this case, it is appropriate to add the lipids before the complex has been isolated and cleaned, as is described in the applicant's European patent EP 0 242 380 B1.

The lipids used are particularly the kind described in the applicant's patent EP 0 109 942 B1 in particular on p. 3 and in EP 0 436 620 B1, p. 7, lines 7–24. Sterols such as cholesterol and phospholipids such as phosphatidylethanolamine and phosphatidylcholine GM1, where particularly used.

The lipids may also include lipid-containing substances that bind to cell-forming components, for instance glycolipids such as the receptor of cholera toxin, the gangliosid GM1, and focused blood group antigen. The cell-binding components can then function as mucus targeting molecules and be tied to the lipid-containing substances by simply mixing with complexes that contain them.

It is also possible to first prepare ISCOM™ particles from a mucus targeting or passenger antigen and then add on the passenger and mucus targeting antigens respectively using current conjugation methods, preferably chemical coupling methods, as is described in the applicant's European patents EP 0 180 564 B1 and EP 0 436 620 B1.

The base could also be matrices that are prepared by solubilizing at least one sterol in a solubilizing agent, adding the glycoside or the saponins and the other lipids, after which the solution agent may be removed if desired, i.e. if it cannot be accepted in the final product. Matrices are usually transferred to a water solution in which the individual parts are not dissolvable. The solubilizing agent can be removed, for example, by gel filtration, ultrafiltration, dialysis or electrofores. The matrices may then be purified from an excess of sterol and saponin by means of, for example, centrifugation through a density gradient or by gel centrifugation.

The solubilizing agent may be any of those mentioned in EP 0 436 629 B1, p. 5, lines 24–45. The other components and the preparation process are also described in this document.

Passenger and mucus targeting molecule can be bound to the matrices using current binding-conjugation methods, see above. It is also feasible to mix adjuvant molecules and/or passenger antigens with an ISCOM™ molecule in which the passenger antigen or the adjuvant molecule has been integrated, or with ISCOM™ and/or matrix complexes to which the passenger antigen or the mucus targeting molecule has been connected. It is also possible to mix both mucus targeting molecule and passenger antigen with an ISCOM™ complex or matrix in a separate entity, in which case the ISCOM™ complex contains a different antigen molecule.

The glycosides used in the preparation may be those described in EP 0 109 942 B1, p. 4, last paragraph. The preferred method is to use saponins such as triterpensaponins, particularly Quil A or defined components of it, particularly those described in the applicant's European patent EP 0 436 620 B1 p. 4, lines 19–46. These may by QHA, QHB, QHC or other compositions of Quil A, such as 703. Glycosides are adjuvants. Or such components described by Kensil, Kersten or Dalsgaard (Kensil, C. R., Patel, U., Lennick, M. and Marciani, D., J. Immunol, 146, 431–437, 1991; Kersten, G. G. A., Spiekstra, A., Beuvery, E. C. and Commelin, D. J. A. BBA1062, 165–171, 1991; or patent WO95/09179 Dalsgaard). It is also possible to incorporate other adjuvants or immune-modulating components than the glycosides in the ISCOMs™ or in the matrices as mentioned in EP 0 436 620 B1.

Examples of such adjuvants are provided in Cox et al., CRS, 1992. The preferred method is to use MDP, MTP and avridin.

If the mucus targeting molecule(s) or the passenger antigen(s) are lacking hydrophobic or amphiphatic groups, they can be added on so that the antigen can bind to the ISCOM™ particle. Examples of such groups are to be found in EP 0 242 380 B1 p. 9 and in EP 0 436 620 B1 p. 6, line 33 to p. 7, line 6, where the connecting methods are described. They may be lipids as in Example 2 below.

The relative amounts of cholesterol, lipids and antigen that can be used are seen in the above-mentioned patents EP 0 109 942 B1, EP 0 180 564 B1, EP 0 242 380 B1 and EP 0 436 620 B1.

Of the bacterial mucus targeting molecules, it is the cholera toxin, its subunits such as B (CTB) and the heat-labile toxin in *E.coli* with its subunits such as B (LTB) that are the most preferable.

Cholera is one of the most dangerous of all diarrhea diseases and is caused by the Vibrio cholera-bacteria 0 group 1. These bacteria colonize in humans in the small intestine where they secrete an exotoxin protein known as the cholera toxin.

Similar diseases are caused by so-called "enterotoxic" coli bacteria (ET) although these symptoms are usually milder and are caused by a heat-labile toxin (LT) that is similar to the cholera toxin (CT). These toxins are so similar that the y bind to the same receptor.

The structures of CT and LT are well defined regarding structure and function. They are oligomer proteins containing a part that binds to the cholera toxin receptor, namely the B-subunit, which in turn contains five subentities that each have an approximate mole weight of 11,600 and have the form of pentamerous rings. The A subunits are proteolytic split polypeptides with a mole weight of approximately 28,000 consisting of two disulfide-bound fragments. The larger A1-fragment contains the toxin-enzyme activity while the smaller A2-fragment attaches the A1-fragment to the B5 ring. CT binds with close affinity to a class of receptors that exist on the surface of the so-called brush-border membrane in the small intestine, and to the plasma membrane in most mammalian cells as well. The receptors are composed of the gagliosid GM1. Moreover, LT binds as well to an unnamed glycoprotein (Holmgran et al., Infect. Immun., 38, 424–433 (1982)). These proteins can also be incorporated in iscom or bound to iscom or matrices, serving as binding molecules to LT.

The gangliosid GM1 and other receptors for mucus targeting molecules of lipid type or hydrophobic may be included in the iscom particles lipid containing region. They may even be a part of the lipid composition in the matrices.

When the receptor is incorporated in the iscom particle or the iscom matrix particle, it can be mixed with a corresponding ligand which binds to the receptor incorporated in the particle. In cases where the carrier or passenger antigen's receptor is a gangliosid, the antigen can be bound to such a receptor through a simple mixing procedure. This procedure is explained in Example 1 below. Similarly, other receptors will bind its antagonist.

The cholera toxin contains the A subunit, which exerts toxin activity, and the B subentity which attach the toxin to the plasma membrane on the cell via a glycolipid (GM1). To reduce the toxicity, usually only the B subunit in the cholera toxin (CTB) is used as a vaccine antigen for producing immune response. The B subunit is not toxic and evokes a relatively weak immune response as compared to CT in local intranasal and parenteral immunization, for instance subcutaneous or intramuscular immunization. In other words, the B subentity has low adjuvant activity. CTB is also available as a recombinant DNA-product. (rCTB) (EP 368 819).

It is difficult to obtain worthwhile physical or economic yields by binding antigens covalently to CTB and LTB, because only a limited number of amino and/or carboxy groups can be activated without seriously diminishing CTB's and LTB's antigen activity or their ability to mucus targeting in the mucosal membranes, and their ability to localize themselves and the enclosed antigens to the lymphatic organs and cells to evoke immune response. Even if a sufficient number of groups are available for chemical conjugating on a carrier molecule, it is well known that it is difficult to obtain worthwhile physical and economic yield from such constructions (Lövgren et al., Immunol. Methods 173, 237–243).

The use of mucus targeting molecules in ISCOMs™ has many advantages. This holds especially true in the preparation of oral, nasal or rectal vaccines against various diseases. Such vaccines can contain a carrier construction with antigen, adjuvant component(s) supplemented with, for example, CTB or LTB in order to localize the construction to the lymphatic organs and cells in the intestinal canal and to other mucous membranes via GALT MALT, NALT (Gut, Mucosal and Nasal-pharyngeal Associated Lymphatic Tissue), such as in the respiratory tracts or directly through local administration.

The ISCOM™ being larger than the mucus targeting molecules there is room for both incorporating chosen passenger antigens and chosen adjuvant components, conjugation or in some other way, such as through hydrophobic interactions or electrostatic binding.

In producing matrices, a common ratio of sterol, another lipid, and glycoside is 0.2–10:0.2–10:1–100, preferably 1:1:5. If using a lipid-containing receptor, it can replace the other lipid completely so that the ratio of sterol, lipid-containing receptor and glycoside will be as above. Another possibility is to use both the lipid-containing receptor and another lipid, preferably phosphatidylcholine or phosphatidylethanolamine plus the receptor, so that the ratio will be sterol; other lipid:receptor:glycoside 0.2–10:0.2–10:0.1–1:5–10, preferably 1:1:0.25:5. The number of receptor molecules depend on the number of molecules one wishes to add on.

In principle, the components can be put in at any ratio whatsoever. It has been shown that the finished product receives the weight ratio between the various components as given above, and that the excess does not enter in. If too much of the other lipid(s) are used, the complex becomes "fatty" and fragile and crumbles easily. Too little of the other lipid leads to the complexes not being formed and annular (ring-shaped) subunits being formed instead. This can be determined through electron microscopy.

It is possible to determine whether the ISCOM™ or matrix has been obtained by examining the product in an electron microscope. Typical matrices or ISCOMs™ have a characterically open, spheric structure consisting of circular subunits, as can be seen in FIG. 3 in EP 0 109 942 B1 and FIG. 3 in this application. The ISCOMs™ have a lower sedimentation constant than corresponding micelles and often a higher sedimentation constant than the corresponding monomeric forms of protein or peptide. Matrices and ISCOMs™ have a sedimentation constant of approximately 12–22 S, in particular 20 S.

The advantage of using lipid-containing receptors for binding the target or mucus targeting antigens is that the matrices can be prepared with glycoside, sterol, possibly another lipid and a lipid-containing receptor, and then simply mixed with the mucus targeting molecule. The process is more effective, less expensive and simpler than if one were to prepare ready-made iscom containing the ingredients above plus the mucus targeting protein antigen or if chemical coupling methods were used to connect the antigen to the ready-made matrix.

When antigen is integrated into ISCOM™ or combined with matrix using chemical coupling methods, the amino or the carboxyl groups that make up the antigen determinants are modified.

Antigen determinants are denatured when the antigen is activated to covalently bind it to the iscom or to attach a hydrophobic tail to facilitate for integration into iscom or when it is coupled by chemical methods to matrix or iscom (when two antigens are used.) This means that the amount of unmodified antigen is greatly reduced compared with a mode of allowing the antigen to bind to a lipid-containing receptor. This can mean, for example, that approximately five times more antigen is needed compared to the mode of using a lipid-containing receptor. When a lipid-containing receptor is used, the process is much less expensive. Parallel to a decrease in the degree of incorporation, there is an increase in the amount of glycosid and the adjuvant content, which partly compensates for the smaller amount of antigen in the attained immune response. At the same time, toxicity may increase due to the increased adjuvant content. In principle, however, the immune response is higher when receptor binding of the antigen is used.

There is another advantage, too, when aspiring to bind a mucus targeting molecule and a passenger antigen to ISCOM™ or matrix. If the ISCOM™ or matrix is made from lipid-containing receptors, there is more space to integrate the passenger antigen into iscom or to bind it to matrix using chemical coupling methods. The usage of a lipid-containing receptor does not influence the binding of the passenger antigen. This makes it easier to obtain optimal ratios. It is easier to regulate the amount of passenger antigen and mucus targeting molecules integrated into ISCOM™ or connected to ISCOM™ or matrix using chemical methods. On the other hand, if iscom is made using a mucus targeting molecule and antigen with the same methods, they compete for the binding and it becomes difficult to wholly regulate the incorporation of both components.

Particularly in regard to the cholera CTB subunit, which has five binding sites subunits, it is possible to bind up to 13 times the weight of the GM1-receptor. This still leaves binding entities in CTB that are able to bind to receptors in the mucous membrane and serve as molecules.

The weight ratio of sterol, other lipid, protein and glycoside is 0.2–10:0.2–10:2–10:1–100, preferably 1:1:1:5–10 in subcutaneous administration. In oral or intranasal administration, the amount of glycoside may be higher in the ratio above, namely 1–200, preferably 5–20.

These are the appropriate amounts both when matrix is first produced and bound to the antigens using chemical coupling methods and later when iscom particles are made.

All of the above-mentioned paten documents as well as the priority document SE 9600647-3 are included as reference.

The amount of ISCOM™, matrix and antigen is chosen to be pharmaceutically effective and can be estimated by the man of art. For humans at least 1 $\mu$g, especially from 1 up to 200 $\mu$g of the antigen may be used, whereby economical aspects set the upper limit. For animals the dose may be at least 0.1 $\mu$g of the antigen depending on the antigen and the size of the individual.

ISCOM™ or ISCOM™ matrix can be prepared in compositions containing a solubilizing agent, e.g. water or sodium chloride. The composition may also contain the detergent used in making the complex as a solubilizing agent, if it is acceptable from the point of view of human or veterinary medical practice. Moreover, the compositions may contain other additives and filler agents acceptable to human or veterinary medical practice.

Such a composition may contain, for example, an ISCOM™ complex and an inert filler such as sodium chloride. It may also consist of a matrix mixed with antigen.

The vaccine may be made available for modes of administration that contain an entity with matrix in a composition containing an inert filler and an entity with the antigen in a composition containing an inert filler. These two compositions are intended to be administered at the same time.
EXP OVA I

EXAMPLE 1
Incorporation of GM1 and rCTB into ISCOMs™

Cholera toxin (CT) is an efficient adjuvant (Holmgren, J., Czercinsky, C., Sun, J-B. and Svennerholm, A-M. in Concepts in Vaccine Development, Ed. S. H. E. Kaufmann, 1996) especially by local immunization. Even the B-subunit (CTB) is filed as an adjuvant, according to literature, because of its target seeking qualities by local immunization, but this activity is thus limited to a guiding function for the antigen to the lymphatic cells of the intestines. If CTB is bound to ISCOM™-matrix or is incorporated into iscom, a formulation is obtained which potenitates the immune response and is efficient by local and parenteral immunization. This effect is interesting in connection with vaccine against cholera and by choice of adjuvant for other antigens especially by local but also by parenteral immunization.

Recombinant cholera toxin, subunit B (rCTB) (EP 0 368 819) is mixed in different preparations with:

MEGA-10 (Bachem P 1000 Decanoyl-n-methylglucamide), 20 weight-% in $H_2O$;

Phosphatidyl choline (PC) (Sigma P-5763), 10 mg/ml diluted in 20 weight-% MEGA-10 in $H_2O$;

Cholesterol (C) (Sigma C8667), 10 mg/ml diluted in 20% MEGA-10 in $H_2O$;

GM1 (Sigma G7641), 10 mg/ml diluted in 20% MEGA-10 in $H_2O$;

Phosphatidylethanolamine (PE) (Sigma P2768), 10 mg/ml diluted in 20% MEGA-10 in $H_2O$;

Quil A (Spikoside, Isotec, Luleå), 100 $\mu$g/ml in $H_2O$;

rCTB, 5 mg/ml in a buffer with 0.05 M TRIS (pH 7.5), 0.2 M NaCl 0.001 M $Na_2$ EDTA, 0.003 M $NaN_3$.

Phosphatidylcholine was mixed with cholesterol supplemented with traceable amounts of radioactive cholesterol ($^3$H-cholesterol, Amersham) in the proportion 1:1 (100 mg of each lipid in 10 ml 20% MEGA-10) and varying amounts of GM1 from 1 mg to 7.5 µg (1 µg, 1.7 µg, 2.5 µg, 5 µg, 7.5 µg) in 1.0 ml PBS (Phosphate buffered physiological NaCl-solution), pH 7.2.

To 1 ml of the six different variations of phosphatidylcholine/cholesterol-GM-1-solution, Quil A was added to a final concentration of 0.2%. The mixture was sonicated in a Sonorex TK 52 2×15 minutes and was left in room temperature (RT) for 1 hour. Then the mixture was dialyzed against PBS, first for 24 hours in RT and then for 24 hours in a cool room (+4° C.). Electron microscopy (EM) verified the existence (presence) of matrix. 100 µg of rCTB was added to the six variations of matrix, which differ with respect to GM1 contents. The mixture was left for 2 hours in RT. The matrix particles with associated rCTB, i.e. ISCOMs™, was purified by ultracentrifugation in a 10–50% sucrose gradient in PBS for 18 hours in a TST 41.14-rotor (Kontron) at 39,000 rpm at 10° C.

The gradient was collected in 16 to 18 fractions. The fractions were analyzed with respect to rCTB using the protein determination method by Bradford (Bradford, Analyt. Biochem., 72, (1976) 248–254) and was determined cholormetrically at 595 nm, and with respect to lipids by detection of $^3$H-cholesterol, as well as EM to examine the presence of possible matrix or iscom structures. FIG. 1 shows lipid (■) and rCTB (□) amounts in the factions at the proportion rCTB:GM1 13:1 (FIG. 11A) and 100:1 respectively (FIG. 1B).

Results

The highest relative amount (weight) of rCTB which was completely incorporated into the GM1 matrix, i.e. to form the rCTB-ISCOM™, was 13-fold higher than the amount of incorporated GM1 (FIG. 1). In three different experiments, we have seen the same ratio. If a high amount of rCTB is added, the surplus of rCTB higher up on the gradient non-associated to the $^3$H-cholesterol, which shows that this rCTB is not incorporated. If a minor amount of rCTB is added, an aggregations will be found because the rCTB has five possible binding sites to GM1 linking the iscoms to form aggregations. Matrix associated to rCTB, i.e. ISCOMs™ are found in the fractions 7 up to 9 (FIG. 1B). In FIG. 3 is shown EM of different ISCOM™ preparations. Similar results are obtained with phosphatidylethanolamine in matrix and ISCOMs™ respectively instead of phospahtidylcholine (results not shown).

Conclusion rCTB can efficiently be bound to matrix containing the glycolipid GM1. The adding of a suitable amount of GM1 at the preparation of matrix implies an efficient method of preparation for rCTB ISCOMs™.

EXAMPLE 2

CTB AND ISCOMs™ AS IMMUNOLOGICAL TARGET DEVICES FOR PASSENGER ANTIGENS (PA)

Background

It is well documented that the B-subunit of cholera toxin (CTB) can actively play a role as "target seeking protein" for "passenger antigen" or antigen which is administered together with the B-subunit locally in the mucus e.g. intranasally or orally (Holmgren, J., Lycke, N., Czerkinksy. Vaccine 11, 1179–84, 1993). The B-subunit can be successfully produced as a recombinant DNA-product (rCTB) and, therefore, it is attractive as a target seeking protein for vaccine antigen administered via mucus membranes.

The purpose of this example is to show that ISCOMs™ in combination with rCTB or without rCTB enhance the immunostimulating effect of incorporated antigen PA (passenger antigen) or co-administer antigen (CA) by intranasal (i.n.) application on mucus. The experiment was carried out to show that ISCOM™ constructions and constructions with iscom matrix has an immunomodulating effect by evoking the type of immune response desired for immune protection. In these experiments, the specific immune responses against OVA, rCTB or a combination thereof were evaluated. The distribution of the immune responses in mucus in the isotypes IgA and IgG and in serum in different IgG-subclasses were studied.

Material

OVALBUMIN fraction V (OVA) (SIGMA A2512, St. Louis, USA)

PHOSPHATIDYLETHANOLAMINE-dioleoyl (PE) 10 mg/ml in 20 weight % MEGA-10 (SIGMA P-0890 St. Louis, USA)

$^{14}$C labelled PE (AMERSHAM, Buckinghamshire, UK)

CHOLESTEROL (C) 10 mg/ml in 20% MEGA (SIGMA C 8667, P0890 St. Louis, USA)

Phosphatidylcholine (PC) (Sigma C8667) 10 mg/ml in 20% MEGA-10 in $H_2O$

MEGA 10 Bachem P1000, Basel, Switzerland Decanoyl-n-methylglucamide (20 weight % in $H_2O$)

SULFO-NHS N-hydroxysulfosuccinimide (NHS) (PIERCE No 24510, Rockford, USA)

EDC 1 Ethyl-3 (-dimethylaminopropylcarbodemide-HCL (PIERCE NO 22980, Rockford, USA)

QUILLAJA SAPONIN in $H_2O$ 100 mg/ml (Spikoside, Advet AB, Luleå, Sweden)

rCTB recombinant B-subunit from cholera toxin was a gift from Jan Holmgren, Department of Immunology, Göteborg, Sweden.

PBS pH 7.2

ISCOM™-matrix was obtained from Advet, Luleå, Sweden.

Animals

NMRI-mice, females 18–20 g, from the National Veterinary Institute, Uppsala, Sweden Methods Preparation of ISCOMs™

OVA was supplied with a lipid tail-phosphatidylethanol (PE)—dioleoyl according to manufacturer's description, Pierce (Rockford, Ill., USA) modified by us (Karina L övgren-Bengtsson). In brief: 1 mg OVA, 1 mg PE, 1 mg NHS, 20 mg EDC were incubated for 2 hours at 37° under agitation in a total volume of 775 µl $H_2O$.

1 mg C, 5 mg Quillaja was added to the above-mentioned solution. To facilitate the binding of CTB, 40 µg GM1 per 1 mg OVA was added to the preparation. The final concentration of MEGA-10 reached 2% in a total volume of 1.1 ml. The solution was incubated for 2 hours in RT under agitation, then dialyzed against PBS in RT for 48 hours. The morphology of the iscom was confirmed by electron microscopy. rCTB was added to the preparation with out without GM1. rCTB was incorporated in iscoms as described in Example 1 by incorporation of GM1 (see Example 1). In other preparations, the GM1 was omitted to avoid binding of the rCTB. ISCOM™ particles containing OVA or rCTB or both, were purified by ultracentrifugation in a 10–50% sucrose gradient in PBS for 18 hours in a TST 41.14-rotor (Kontron) at 39,000 rpm in 10° C. The gradient was collected in 16 to 18 fractions. The fractions were analyzed with respect to rCTB by the method for protein determination according to Bradford (Bradford, Analyt. Biochem. 72, 1976, 248–254) and were defined cholormetrically at 595 nm, and with respect to lipids by detection of $^3$H-cholesterol, as well as by electron microscopy to examine the existence of possible matrix- or iscom structures.

Characterization of the Different ISCOM™ Components

FIG. 4A shows free rCTB (□) measured by protein determination, analyzed in a 10–50% sucrose gradient centrifugation, i.e. rCTB non-incorporated into iscom sediments slowly and is recovered high up in the gradient, i.e. fractions 12–14.

FIG. 4B shows the lipid radioactivity (CPM) of cholesterol which follows the ISCOM™ by ultracentrifugation in a sucrose gradient (■) and lipidated protein OVA measured according to Bradford (Ref. see text) (□) iscom with OVA are detected in fractions 6–8. The gradient is a 20–50% sucrose gradient centrifuged for 18 hours in a TST 41.14 rotor at 39,000 rpm. Some non-integrated protein fractions 11, 12 and 13. Bradford was measured as absorbance at 595 nm.

FIG. 4C shows incorporation of rCTB in iscoms with GM1. Incorporation of rCTB in ISCOMs™ was measured by protein determination (Bradford) (□). Sedimentation of ISCOMs™ is shown by radioactively labelled cholesterol (CPM) (■) following the iscom in the gradient. Both proteins i.e. rCTB, cholesterol, and ISCOM™ structures, the latter verified by electron microscopy, are found in fractions 6–9.

By producing OVA-ISCOMs™ with GM1 lipid, the rCTB can be incorporated by being added to the OVA-ISCOMs™ as shown in FIG. 4D. Incorporation of both lipidated OVA and rCTB is demonstrated by protein determination according to Bradford (□). Sedimentation of ISCOMs™ are shown by radioactivity in labelled cholesterol (CPM)(■) found in fractions 4–6 and the ISCOM™ structures were determined by EM. FIG. 4E shows that if rCTB is added to OVA-ISCOMs™ which are devoid of GM1-lipids, the rCTB is not incorporated into ISCOM™ proven by the fact that the protein, i.e. rCTB, is found on the top of the gradient i.e. the fractions 11–13. Iscom incorporated OVA is layered in fractions 5–8.

Immunization Experiments

NMRI-mice 20 g from the Animal house of the National Veterinary Institute, Uppsala, were used. The following groups, listed below, have been immunized intranasally (i.n.) with 10 μg of each preparation or subcutaneously (s.c.) with 2 μg twice, six weeks apart.

Groups
1. i.n. 10 μg OVA without Quillaja (QA)
2. i.n. 10 μg OVA-ISCOM™
3. i.n. 10 μg OVA-ISCOM™ and 10 μg free rCTB
4. i.n. 10 μg of OVA and rCTB in the same ISCOM™
5. s.c. 2 μg OVA-ISCOM™
6. i.n. OVA in free form and rCTB in free form 10 μg each.
7. i.n. OVA in free form plus matrix (10 μg)
8. i.n. PBS i.e. control group without antigen The mice were anaesthetized by inhalation of Metafane inn a beaker. For i.n. application, 20 μl of each preparation was given. When immunizing s.c. the dose was given in a volume of 200 μl/mouse in PBS.

Two weeks after the first immunization, serum was tested against OVA and rCTB. After 4 weeks, the mice were given a booster dose and blood samples were taken after additional two weeks. Before the lungs were extracted, the blood vessels were rinsed with 20 ml PBS-0.1% heparin through the right ventricle of the heart and out in the lungs and out through the rest of the blood circulation. The animals were apparently totally drained from blood. Lungs, upper respiratory tracts, genital tract and intestines were directed, dried with a paper towel and put into tubes with PBS-heparin, previously weighed. The organs were weighed and washed with PBS, they were then dried and put into Eppendrof tubes and stored at −20° C.

Before testing of the antibody responses, the organs were taken from the freezer and 2% spikoside in PBS was added 1:1, the lungs were cut in small pieces and the Eppendorf tubes were stored in a refrigerator overnight. Next day, the pieces of organs were centrifuged in an Eppendorf centrifuge for 15 minutes at 13,000 rpm. The supernatant was analyzed for IgA and IgG against OVA and rCTB respectively. Serum was tested against OVA and rCTB in ELISA and the antibody responses in IgA, IgG subclasses IgG1 and IgG2a total IgG were analyzed.

By Intranasal Administration, the ISCOM™ Constructs Evoke Higher Immune Responses than rCTB-formulations Without ISCOMs™ or ISCOM™-Matrix The Serum Antibody Response Against OVA was Followed After One and Two i.n. and s.c. Immunizations (see FIG. 5).

The rCTB-OVA-formulation does not evoke a serum antibody response against OVA, not after one or even two immunizations. FIG. 5A and Table 1 show serum antibody response against OVA analyzed with ELISA after one intranasal (i.n.) immunization of mice. No antibody response could be measured against OVA without adjuvant or against OVA adjuvanted with rCTB. All mice that were immunized with OVA-ISCOM™ formulation and OVA supplemented with ISCOM™-matrix responded by a rise in the antibodies that could be clearly measured.

TABLE I

The serum antibody response ($\log^{10}$ titres) to OVA two weeks after the second intranasal immunization of mice analyzed in ELISA with regard to the total antibody response and the responses in the subclasses IgG1 and IgG2a intranasal immunizations.

| Group | IgG | IgG1 | IgG2a |
|---|---|---|---|
| 1 ova | 2.09 ± 0.68 | 2.30 ± 0.94 | 1.48 |
| 2 ova-iscom | 4.03 ± 0.65 | 4.17 ± .079 | 2.40 ± 1.04 |
| 3 ova-iscom + rCTB | 3.71 ± 0.90 | 4.00 ± 0.99 | 2.72 ± 1.06 |
| 4 ova/rCTB-iscom | 3.77 ± 0.61 | 4.03 ± 0.72 | 2.25 ± 0.96 |
| 5 ova-iscom S.C. | 4.59 ± 0.36 | 4.60 ± 0.30 | 4.17 ± 0.57 |
| 6 ova + rCTB | 1.55 ± 0.16 | 1.51 ± 0.08 | <1.48 |
| 7 ova-iscom-matrix | 4.37 ± 0.11 | 4.81 ± 0.07 | <1.48 |
| 8 negative control | <1.48 | <1.48 | <1.48 |

FIG. 5B shows that two weeks after the second immunization all the mice that had been immunized with ISCOM™ or matrix formulations responded with high serum antibody titres against OVA. Mice that had been immunized with OVA supplemented with rCTB mixed as separate entities and however serum antibody titres than mice that were only immunized with OVA. This implies that rCTB induces tolerance against OVA having as a result that the mice do not respond with serum antibodies against OVA.

FIG. 5C shows ELISA values at increasing dilution of serum from mice after two immunizations. As shown in this FIGURE as well as in FIG. 5B, the ISCOM™ formulations with OVA breaks the tolerance that rCTB evokes for serum antibody response against OVA as "passenger antigen" or co-administered antigen.

Table 1 shows serum antibody response ($\log^{10}$ titres) against OVA two weeks after the 2nd i.n. immunization of mice analyzed in ELISA with respect to the total IgG response and the response in IgG1 and IgG2a subclasses. It is especially interesting that the ISCOMs™ highly upregulate the IgG2a-response compared to OVA plus iscom matrix. Furthermore, OVA-iscoms and OVA/rCTB ISCOMs™ and OVA-ISCOMs™ plus free rCTB induce a higher IG1-response compared to the IgG2a-response than OVA ISCOMs™ injected s.c. This can be measured as a quota IgG1/IgG2a. OVA without additive of adjuvant evoked a low antibody response which could only be shown in the IgG1 subclass. I.n. application of OVA-ISCOMs™ with free rCTB or iscoms containing both rCTB and OVA evoked unexpectedly strong serum antibody response localized to both IgG1 and IgG2a-subclasses. The immunomodulating effect is proven by the production of IgG2a. This is an indication of the induction of an IFN-γ response (Coffmann, R. L., Seymour, B. W. P., Lebman, D. A. et al., Immunol. Rev. 102, 5–28, 1988). OVA-rCTB evoked a tolerance-like state with respect to the serum antibody response. However, it was unexpected that this state of tolerance was effectively abrogated by the ISCOM™ formulations and by the ISCOM™-matrix.

ISCOM™ Formulations Evoke a Stronger Antibody Response in Mucous Membranes of Mice Against Passenger Antigen than rCTB-formulations (FIG. 6).

IgA Antibody Response in Lung Secretion

All ISCOM™ formulations with OVA or with OVA-ISCOM™ matrix administered i.n. evoked significantly higher IgA titres in lung secretions than free OVA supplemented with rCTB and than OVA-ISCOMs™ administered s.c. or than OVA alone in free form administered i.n. In FIG. 6A, IgA antibody response was analyzed in lung (after two i.n.) immunizations of mice. The comparison shows that ISCOM™ formulations evoke significant IgA antibody responses after i.n. administration as opposed to the rCTB-OVA formulation in the low doses (10 µg) used.

FIG. 6B shows a comparison between the different groups with respect to IgA antibody responses in the upper respiratory tract OVA-ISCOMs™ and OVA supplemented with matrix evoke significantly higher IgA-titres than OVA-rCTB formulations.

In extract from genital tract, OVA-ISCOMs™ complemented with rCTB evoked significantly higher IgA anti-OVA ($10^2 \pm 0.38$) than OVA adjuvanted with rCTB ($10^{1.4} \pm 0.25$) or than control mice ($10^{1.2}$). Even rCTB incorporated in OVA-ISCOMs™ evoked significantly higher IgA titres ($10^{1.7}$) in genital extract than control mice ($10^{1.2}$). The latter indicate the background for ELISA (FIG. 6C).

IgG Antibody Response Against OVA in Mucous Membranes

Generally, ISCOMs™ and matrix formulations administered i.n. or s.c. which contained OVA evoked significantly higher IgG antibody titres in extract from mucous membranes of the lungs and upper respiratory tracts than OVA plus rCTB and non-immunized control mice (FIGS. 7A and B).

rCTB seems to induce a powerful tolerance against IgG immune response against OVA in lung extracts which is more pronounced than that against IgG antibody response. this tolerance is clearly abrogated by ISCOMs™ and ISCOM™ formulations.

Also in secretion of the genital tract OVA-ISCOMs™, OVA-rCTB-ISCOMs™ and ISCOM™-matrix formulations with OVA induced significant and very high IgG antibody responses to OVA compared to that induced by a rCTB OVA formulation. In intestinal secretion iscoms with OVA induced higher IgG antibody titres than OVA supplemented with free rCTB or OVA supplemented with ISCOM™-matrix. The results are shown in FIGS. 7C and 7D.

Conclusion

Comparison between ISCOM™ and rCTB

ISCOMs™ are unexpectedly and considerably more efficient following mucosal administration as an adjuvant and "target seeker" for "passenger antigen" and SA, here represented by OVA than a formulation of OVA and rCTB.

This is valid both for the secretory antibody response encompassing the IgA response locally in secretion of the respiratory tract, such as in the lung as well as in the mucous membranes farther away from the site of administration such as in the genital tract and in intestines.

Also, the IgG antibody responses in secretion from mucous organs such as lungs, upper respiratory tracts, intestines and genital tract are considerably enhanced following mucosal administration of OVA as a model antigen in ISCOMs™ or together with ISCOM™ matrix compared to the enhancement brought about OVA administered together with rCTB.

It is also noteworthy that following the mucosal administration of passenger antigen in ISCOMs™ or co-administered with ISCOM™-matrix, the serum antibody response was considerably more enhanced that what rCTB could bring about.

A corresponding effect as to the enhancement of antibody response in secretion may be obtained if the A-subunit of the cholera toxin is present with its B-subunit, i.e. the whole cholera toxin. However, whole cholera toxin is toxic, pathogenic and not acceptable as an adjuvant (Holmgren, J., Czercinsky, C., Sun, J-B. and Svenerholm, A-M. in Concepts in Vaccine Development, Ed. S. H. E. Kaufmann, 1996). Similarly, the whole toxin LT and its equivalent to CTB i.e. LTB suffer the same problems as LT and CTB.

The rCTB downregulated the IgG-antibody response in mucous secretion of the co-administered antigen. Unexpectedly and very distinctly, the downregulating or tolerance inducing effect of rCTB on the passenger antigen was effectively abrogated by ISCOMs™ and ISCOM™-matrix formulations.

The immunomodulating effect of ISCOM™, ISCOM™/target seeking molecule or ISCOM™-matrix formulations is demonstrated by the upregulated serum antibody response against IgG2a also following mucosal administration which is an indicator of participation of the IFN-γ immune response, i.e. TH1 response.

Comparison of Matrix and rCTB

Matrix plus antigen (OVA) administered together on the mucous membrane is more efficient than rCTB plus antigen administered together on the mucous membrane i.n. as for IgA antibody response in secretion from lungs and genital tract. Also the IgG antibody response in secretion from mucous organs such as lungs, respiratory tract and genital tract is considerably enhanced compared to what OVA-rCTB formulations can bring about.

Also the specific serum antibody response induced by OVA with matrix as a mucous membrane adjuvant was considerably higher than that induced by a formulation of OVA supplemented with rCTB. It was unexpected that matrix could have such a strong adjuvant effect locally in mucous membranes. It is noteworthy that the matrix is very simple to use as an adjuvant by simply being added to the vaccine antigen as opposed to aluminum hydroxide which requires an adsorption under the right conditions, or opposed to oil adjuvants which require a technical preparation in the form of emulsions which are a complicated procedure in an industrial vaccine production.

It is especially interesting that the ISCOM™ or ISCOM™-matrix can be used to induce a powerful immune response by mucosal administration. The CTB or LTB can be used to down-regulate this immune response. These combinations can be used to induce immune response and when desired and to down-regulated this antibody response when desired. The possibility to up- and down-regulate an antibody response in the female genital tract which is specific for sperm antigen is of interest in a contraceptive vaccine. The induced antisperm antibody needs to be abrogated against sperms.

Comparison between ISCOM™ and ISCOM™-matrix

ISCOM™ and matrix can be similar as to morphology, e.g. studied in EM, the composition as to triterpenoids, lipids or incorporated adjuvant molecules. However, the ISCOMs™ contain an in-built antigen opposed to the matrix which exerts its adjuvant activity on co-administered antigens which are not integrated.

In this example, comparisons between ISCOM™-matrix and ISCOM™ as mucosal adjuvant formulation for administration of OVA were carried out. The effects are locally evaluated in secretions extracted from lungs, upper respiratory tracts, genital tracts and intestines. Generally, it can be stated that ISCOMs™ in certain instances are more effective mucous membrane adjuvants than matrix. ISCOMs™, e.g., induce a higher IgG2a antibody response in serum which can be advantageous for protection against certain virus diseases.

In other cases, the matrix-OVA formulations induce the same level of antibody response as OVA-ISCOM™ formulations. The IgG-response in mucus of the intestines was considerably higher after i.n. immunization with iscom formulations than with OVA-matrix.

The simple adding of the matrix to the antigen preparation is a great advantage.

The Serum Antibody Response Against rCTB

The results are presented in Table 2 after two i.n. immunizations. The ISCOM™ preparations induced high serum antibody responses (group 3: $10^{4.9}$±0.51; group 4: $10^{5.1}$±0.54 encompassing high IgG2a responses. rCTB evoked considerably lower antibody titres ($10^{3.3}$±0.4). All rCTB preparations induced significantly higher antibody titres than non-immunized control mice.

TABLE II

A comparison between serums antibody responses to rCTB ($log^{10}$ titres) after the second intranasal immunization in mice with regard to IgG isotype and IgG1 and IgG2a subclasses.

| Group | IgG | IgG1 | IgG2a |
|---|---|---|---|
| 3 ova-iscom + rCTB | 4.90 ± 0.51 | 4.54 ± 0.23 | 3.77 ± 0.77 |
| 4 ova/rCTB-iscom | 5.11 ± 0.54 | 4.74 ± 0.72 | 4.21 ± 0.80 |
| 6 ova + rCTB | 3.30 ± 0.40 | 3.19 ± 0.32 | 1.70 + 0.18 |
| 8 negative control | <1.48 | <1.48 | <1.48 |

IgA Antibody Response Against CTB in Secretion from Different Organs

OVA/rCTB-ISCOMs™ or free rCTB supplemented with OVA-ISCOMs™ or which in this case as an adjuvant in the form of ISCOM™-matrix for rCTB, induced, after two i.n. immunizations, considerably higher IgA antibody responses than rCTB without added adjuvant formulations in all tested mucus, i.e. from lung, upper respiratory tract, intestines and genital tract (FIGS. 8A and B).

An interesting feature is that rCTB did not induce IgA antibody responses to itself in mucus of the intestines.

IgG Antibody Response Against rCTB Mucus from Different Organs

High IgG antibody responses were detected against rCTB in secretions from lungs upper respiratory tracts, genital tract and intestines with rCTB-formulations in ISCOM™ or with ISCOM™-matrix. The IgG antibody responses in these mucosal secretions from mice immunized with rCTB without ISCOMs™ or ISCOM™-matrix formulations was lower than for iscoms or ISCOM™-matrix formulations but the levels were significantly higher than for those from non-immunized controls (FIGS. 8C and D).

Conclusion

The results show that ISCOM™ formulations unexpectedly efficiently enhance the antibody response against rCTB after i.n. immunizations both locally in secretions from the respiratory tract and in secretions from distant organs i.e. ub sections from the intestine and genital tracts.

Even the serum antibody response against rCTB was strongly enhanced by the ISCOM™ construction or the ISCOM™-matrix as a separately added adjuvant. The immune modulatory effect of the iscom and the ISCOM™-matrix is demonstrated by the fact that the antibody response against rCTB was induced in the IgG2a subclass which indicates that an IFN-γ production is induced which is an indication of a TH1 type of response.

A surprising example of immune modulation by ISCOMs™ and ISCOM™-matrix is demonstrated by the result of rCTB, which by itself does not convert the antibody response in the intestines to encompass an IgA-response, as opposed to the IgA responses in other secretions. However, CTB presented by ISCOM™ or co-administered with ISCOM™-matrix converted the antibody response to encompass IgA specific for CTB.

EXAMPLE 3

The Kinetics of the Development of Specific Antibody Response in Serum and Lung Secretion After i.n. Immunization with ISCOMs™ Carrying Influenzavirus Antigens In this example, we demonstrate the kinetics of the development of the specific antibody response in serum and lung secretion after i.n. administration of influenza virus antigen, i.e. the envelope proteins from the PB8 isolate which are incorporated into ISCOM™.

Preparation of Influenza-ISCOMs™

Preparation of the Envelope Protein from Influenza Virus

A purified preparation of the H1N1-influenza virus isolate PR8 (A/PR/8/34) with a concentration of 2.6 mg/ml was used. The detergent MEGA-10 was added at a final concentration of 2 weight % the solution was incubated at 37° C. for 15 minutes and thereafter for 60 minutes at RT. In order to separate solubilized envelope proteins from virus debris, the above-mentioned solution (1 ml) of 0.6 ml 10% sucrose in PBS containing 2 weight-% MEGA-10 over a 2.8 ml 30 weight-% sucrose in PBS, and centrifuged in a TST 55.5 Kontron-rotor at 40,000 rpm for 30 minutes. Free envelope proteins were collected in a top layer of 1.5 ml.

The amount of protein was determined to 0.855 ug. the hemagglutinin activity (HA) of the solubilized envelope proteins (570 μg/ml) was determined to 1:4096 with chicken erythrocytes.

Preparation of ISCOMs™

To an amount of 570 μl envelope protein in one ml 0.5 mg cholesterol (C) was added and 2.5 mg Quil A (Spikoside, Advet, Luleȧ, Sverige) The solution was incubated for 2 hours in RT and thereafter dialyzed for 48 hours in a cool room.

Characterization of the Prepared Iscoms

PR8-ISCOM™ (FIG. 2B) was analyzed by ultracentrifugation in a 10–50% sucrose gradient. Sample volumes exceeding 1.5 ml were divided and distributed on two identical gradients. The samples were centrifuged in a TST 41.14-Kontron-rotor at 39,000 rpm for 18 hours. In all preparations, there were proteins as a top-layer in fractions 5, 6, 7 and 8 with a maximum value in fraction 6. This is well in line with what is expected of an ISCOM™ particle. Radioactive $C^{14}$ cholesterol was detected in the same fractions. The protein level was determined according to Bradford.

Further characterization was done by EM (FIG. 3). The ISCOMs™ were also examined with respect to their capacity of hemagglutination. PR8-iscoms agglutinated red blood cells from hens.

Immunization Experiments in Mice in Order To Study the Development of the Immune During 48 days After Two i.n. Immunizations Seven groups of five mice in each were immunized i.n. with 7 μg PR8-iscoms at an interval of three weeks and the antibody responses were followed in serum and in lung secretions with ELISA as demonstrated in FIG. 9.

Antibody Response in Serum

FIG. 9A shows that the total antibody response rose to a reciprocal ELISA-titre of approximately 1000 after one immunization. One week after the booster injection, a 40-fold rise of the total antibody titres was obtained. On day 50, i.e. 30 days after the second i.n. immunization the titres were still at the same elevated antibody level.

FIG. 9B shows that high antibody titres were observed i sera of the IgG-subclasses IgG2, IgG2a and in IgG2b. FIG. 9C shows that IgA serum response against PR8 comparatively low in serum.

Antibody Response in Secretions of the Lungs

FIG. 9D shows that after one immunization low antibody titres of IgA type can be measured with ELISA by absorbance at 40 nm and in dilution 1/90. After a second immunization, a distinct booster effect an be observed with a clear rise of the IgA-antibody titres against PR8.

Conclusion

A low dose of PR8-ISCOMs™ induce, after only one i.n. immunization, antibody response in serum as well as in lung secretions. After two i.n. immunizations potent rises in both serum and lung secretions are achieved. The antibody responses are unexpectedly high after i.n. immunization with low doses of antigen in ISCOMs™ compared to other formulations described in the literature, which, therefore, require several immunizations as well as higher doses.

This implies that it is feasible to formulate a practical immunization program based on i.n. immunization with ISCOMs™ of the right composition.

EXAMPLE 4

ISCOMs™ with Target Seeking Molecules from Influenza Virus and Passenger Antigen (OVA)
Methods
Preparation of ISCOMs™ as Carrier Particles for Local Immunization Via Mucous Membranes Ovalbumin (OVA) is a protein which in a low dose does not spontaneously induce immune response when administered via mucous membranes. Furthermore, OVA is a protein which is not spontaneously incorporated into ISCOMs™. In this experiment, a lipid tail is therefore coupled to the OVA. Lipidated OVA and envelope protein from influenza virus were incorporated together with ISCOMs™. These ISCOMs™ containing both viral envelope protein (targeting protein) and OVA (passenger antigen) are used for i.n. immunization of mice.

Step 1: Lipidation of OVA According to Example 2
Step 2: Formulation of Envelope Protein from Influenza Virus (see page 34)
Step 3: Formulation of ISCOMs™ with Envelope Proteins PR8 and Ovalbumin (OVA)

1 mg of cholesterol (C), 330 μg PR8 envelope protein from step 2 and 5 mg Quil A (Spikoside, Advet, Luleå, Sverige) were added to the solution of lipidated OVA. The total volume of the solution amounted to 2.7 ml and it was incubated first for 2 hours at RT and then dialyzed against PBS over night in RT and thereafter for 48 hours in cool storage (+4° C).

In control experiments ISCOMs™ with only PR8 and ISCOMs™ with only lipidated OVA were prepared.
Characterization of PR8-ISCOMs™

OVA-ISCOMs™ (FIGS. 2A; 3A), PR8-ISCOMs™ (FIGS. 2B; 3B) and OVA-PR8-ISCOMs™ (FIG. 2C; 3C) were characterized by ultra-centrifugation in a 10–50% sucrose gradient. Sample volumes exceeding 1.5 ml were divided and applied on two identical gradients. The samples were centrifuged for 18 hours in a TST 41.14-Kontron-rotor at 39,000 rpm. In all preparations the protein was detected as a peak in the fractions 5, 6 and 7, with a maximum value in fraction 6. The sedimentation and morphology of the particle is well in line with the expectations of an ISCOM™. Radioactive cholesterol and PE were detected and peaked in the same fractions. the protein level was determined according to Bradford. FIG. 2 shows the protein level and the radioactivity of cholesterol or PE as a function of fractions for the prepared iscom particles.

Immunization Experiments in Mice

Five groups of five mice (NMRI) were immunized in accordance with the following schedule:

| Group | Immunizing substance | Mode of administration |
|---|---|---|
| A | OVA-ISCOM ™ | 5 μg antigen i.n. |
| B | OVA/PR8-ISCOM ™ | 5 μg antigen i.n. |
| C | OVA/PR8-ISCOM ™ | 10 μg antigen i.n. |
| D | PR8-ISCOM ™ | 5 μg antigen s.c. |
| E | OVA/PR8-ISCOM ™ | 5 μg antigen s.c. |

The dose indicates the total amount of antigen composed approximately of equal parts of OVA and PR8-antigen respectively. The mice were anaesthetized with Methophane (Pitman Moore) and the doses of antigen stated in the schedule above were administered i.n. twice four weeks apart in a volume of 20 μl i.n. or in 200 μl for the s.c. route. Two weeks after the first and second immunizations the antibody titres in serum were analyzed with ELISA (Voller, A., Bartlett, A., Bidwell, D. E. Scand. J. Immunol. 8, 123–129, 1978). A third immunization was carried out day 56 in accordance with the schedule above. Two weeks later (day 70), the mice were anaesthetized and the blood vessels of the lungs were rinsed with PBS/heparin (0.1%) via the right ventricle. The lungs and the upper respiratory tract were dissected and extracted for a few hours with saponin/PBS-solution (0.2%) and the material was stored in a freezer, as described in Example 2, the antibody titres against OVA and PR8 respectively were determined with ELISA.

Serum Antibody Response Against OVA and PR8 after Immunization with Different Iscom Formulations FIG. 10A shows that OVA-PR8-iscoms induce a high serum antibody response against OVA after two immunization i.n. and even a higher after three immunizations compared to OVA-iscoms without envelope protein from influenza virus. As expected, 10 μg of OVA-PR8 iscoms i.n. induced higher antibody response than 5 μg.

PR8 proteins function as target seeking molecules in the mucous membrane where they are administered for the "passenger antigen" OVA. It is a striking and unexpected feature that the OVA-ISCOM™ did not have an apparent effect on the induction of antibody response, in view of the information found in literature (Mowat). The reason for this discrepancy is, no doubt, that conventionally unrealistically high doses are used, i.e. from a 100 μg up to several hundred micrograms of OVA, to be compared with 5 μg up to 10 μg which are used in the formulations described above. In a later experiment 10 μg of OVA-iscoms were administered i.n. and that induced high antibody responses (see page 35). The low doses required with the "target seeking" iscoms described above makes it practically possible to use them for immunizations.

FIG. 10B shows serum-antibody response against PR8. All ISCOM™ formulations containing PR8 induced antibody response after i.n. immunization and the response was enhanced considerably after the second immunization.

Antibody Response in Secretion Extracted from Lungs

FIG. 10C shows the IgA-antibody response in secretion extracted from lungs after three immunizations as described above. Both 5 μg and 10 μg of the PR8-ISCOMs™ induced a dose related, clear-cut IgA antibody responses after i.n. immunizations, compared to the OVA-ISCOMs™ without PR8-proteins as target seeking molecules.

OVA-PR8-ISCOMs™, injected s.c., did not induce antibody response against OVA in lung secretion.

FIG. 10D demonstrates that all ISCOM™ formulations containing PR8-antigen induce high IgA-antibody responses in lung secretion against PR8.

Conclusion

The experiment demonstrates that certain antigens in a low dose, such as OVA, require a formulation guiding the antigen to the lymphatic system when it is administered on a mucous membrane, here exemplified by an intranasal administration, in order to induce an optimal antibody response in secretion and serum.

The ISCOM™ with PR8 as target seeking or guiding molecule meets this requirement.

It was unexpected that the PR8-OVA-ISCOMs™ were so much more efficient than the OVA-ISCOM™ without target seeking protein, especially in view of the accessible literature (Mowat) and later experiments. This can be explained by the low dose of 5 μg OVA which has been used at the described immunizations.

Extension of the Experiment

This experiment using influenza virus proteins as a mucus targeting molecule for OVA was extended to encompass more mice to achieve 1. better statistical basis 2. to include the defined Quillaja components 703 being used in clinical trials. In this experiment the volume was further reduced from 45 to 40 μl used in the previous experiments to 20 μl which would better mimic a realistic volume dose considering the size of the mouse. The ISCOMs™ and ISCOM™-matrix formulations were prepared as described above.

In a first experiment three types of formulations were compared namely OVA-ISCOM™ (A), OVA/PR8-ISCOM™ (B) and free OVA complemented with ISCOM™-matrix in separate entities (C). Further in this layout we also compare the response of mice to i.n. immunization with the mentioned formulation either containing the cruder Quillaja (QA) or the defined 703 Quillaja product.

The immunization schedule carried out by two administrations six weeks apart as described below:

|  |  | Total antigen dose | QA/703 dose |
| --- | --- | --- | --- |
| Group 1 | OVA-ISCOM ™ QA i.n. | 8 μg | 65 μg |
| Group 2 | OVA-ISCOM ™ 703 i.n. | 8 μg | 65 μg |
| Group 3 | OVA/PR8-ISCOM ™QA i.n. | 16 μg | 75 μg |
| Group 4 | OVA/PR8-ISCOMs ™ 703 i.n. | 16 μg | 65 μg |

-continued

|  |  | Total antigen dose | QA/703 dose |
| --- | --- | --- | --- |
| Group 7 | free OVA-matrix QA i.n. | 10 μg | 50 μg |
| Group 9 | free OVA-matrix 703 i.n. | 10 μg | 50 μg |
| 10 | free OVA non-adjuvanted i.n. | 10 μg | — |
| Controls 11 |  | irrelevant antigen | 65 μg |

Results

Serum antibody response to the passenger antigen OVA. After the first and second immunization the antibody responses were in general higher in mice receiving matrix-formulations than mice receiving ISCOM™ formulations (A, B and C). The total antibody response after the second immunization (in FIG. 10F the results are summarized) was highest for formulations with OVA as a separate entity mixed with matrix (C). The formulations containing the defined Quillaja components i.e. 703 responded with slightly higher IgG titres to OVA than the more crude QA (2 vs 1; 4 vs 3; 9 vs 7). The antibody response in the IgG2a subclass was also higher than 703 formulations.

The IgG2a response was highest in serum from mice immunized s.c. with OVA plus ISCOMT™-matrix group. Of particular interest with regard to human use is that the 3 Quillaja formulation with defined Quillaja components 703 is as efficient if not a better inducer of serum antibody response than the more crude spikeside (QA) based formulations.

The second experiment the serum antibody response to OVA measured by ELISA after i.n. immunizations was compared with that of mice immunized by the subcutaneous (s.c.) route. The immunization schedule was carried out with two administrations six weeks apart and is presented below:

|  |  | Antigen dose | QA/703 dose |
| --- | --- | --- | --- |
| Group 3 | OVA/PR8-ISCOM ™ QA i.n. | 16 μg | 75 μg |
| Group 4 | OVA/PR8-ISCOM ™ 703 i.n. | 16 μg | 65 μg |
| Group 5 | OVA/PR8-ISCOM ™ 703 s.c. | 5 μg | 21 μg |
| Group 6 | OVA + matrix QA s.c. | 20 μg | 10 μg |
| Group 8 | OVA + matrix 703 s.c. | 20 μg | 10 μg |

Results

Serum Antibody Responses to OVA

Surprisingly the analyses of serum antibody responses carried out in ELISA after two immunizations showed that the i.n. immunization evoked antibody responses of similar magnitudes (FIG. 10g) as those induced by s.c. mode of administration. The highest response ($10^{4.3}$) was induced by free OVA adjuvanted with ISCOM™-matrix immunized s.c. to be compared with OVA/PRB-iscoms either with QA or 703 Quillaja-components ($10^{3.9}$).

IgA Responses in Secretions to OVA

The IgA responses to OVA was measured in secretions from lung (FIG. 10H) and from the genital tract (FIG. 10I). The immunization schedules for the different groups are listed in pages 23 and 24.

Lung: (FIG. 10H) The highest IgA response to OVA was obtained with OVA/PR8 ISCOMs™ either with 703 (4) or with QA (3), free OVA supplemented with 703-matrix (9).

Induction of anti-OVA IgA Responses in the Remote Organ the Genital Tract

In FIG. 10I it is shown that the highest IgA response to OVA was induced by OVA/PR8-ISCOMs™ 703 (4) prepared with 703 Quillaja components ($10^{3.3+0.53}$). This response was significantly higher than those induced by i.n. administration of OVA mixed and complemented with matrix in separate entities (7,9). This IgA response is of similar level as that induced in lung secretion. A surprisingly high IgA antibody response was induced by OVA-ISCOM™ (703) although lower than that induced by OVA/PR8-ISCOM™ (703) ($10^{2.9\ 0.40}$ vs $10^{3.3\ 0.53}$)

The Response to Influenza (PR8) Virus Antigen in Serum and Secretions

The responses mentioned in the title agree in general terms with those in this and previous examples. However, it is noteworthy that after two i.n. immunizations of OVA/PR8 ISCOMs™ containing 703 induce the highest serum IgG2a response. Comparative to IgG1 the IgG2a titres in serum increased with time. the serum antibody response tested was from the 3rd bleeding showing that the serum antibody response is comparable with that induced by the s.c. administration.

Conclusion

The influenza virus envelope protein incorporated into iscoms are of particular interest to guide the immune response measured by specific IgA antibody in this case to OVA to remote mucosal sites exemplified by here the genital tract. the defined components 703 of the origin of Quillaja saponaria molina are at least as efficient if not better than the crude Quil A or spikoside being used in previous experiments by us and others. There have been no reason to expect that until proven by experimental work. It is unexpected that ISCOM™ matrix formulations should be as efficient or even more efficient for induction of serum antibody response following i.n. administration of antigen than ISCOMs™. In contrast and in particular ISCOMs™ with mucus targeting molecules (PR8-proteins) was found to be more efficient than other formulations tested in inducing specific secretory IgA responses particularly in a remote organ. Although the high IgA response in lung secretion is unexpectedly high it is even more unexpected to find the high IgA response in the remote mucosal of the genital tract. It was also unexpected that i.n. administration of influenza virus ISCOM™ with 703 should be more efficient than the more crude Quil A ISCOM™ to modulate and IgG2a response measured in serum.

EXAMPLE 5

Herpes simplex 2 (HSV-2) causes infection in genital in a large proportion, up to 10%, of the human population and may cause severe lesions and suffering. HSV-2 is a virus with an envelope containing several envelope proteins. Two of these, the glycoprotein B (gB2) and glycoprotein D (gD2), are considered to be antigens which, if they induce the right type of immune response, being most important for induction of protection against disease and infection under optimal conditions. Since infection with HSV-2 occurs via the genital tract, it is desirable to evoke immune response against HSV-2 in the mucous membrane of the genital tract. In the following experiments we have prepared different formulations of gB2 and examined the immune response in serum and secretion from respiratory tracts, genital tract and intestines. The envelope protein from PR8, as in Example 2, has been used as target seeking molecule and the envelope protein gB2 as passenger antigen.

Preparation of Different gB2-Formulations gB2 was obtained as a recombinant product from Chiron, CA. USA.

ISCOM™-matrix, i.e. ISCOMs™ without antigen, was obtained from Advet, Luleå, Sweden.

gB2 and gd2 respectively, were lipidated and incorporated into iscoms in the same way as described in Example 2.

Six groups of 8 mice (NMRI, females 18–20 g from the National Veterinary Institute (SVA) were immunized in accordance with the following schedule:

| Group | Immunogen | Dose per antigen |
|---|---|---|
| 1 | gB2-ISCOM ™ | 10 μg |
| 2 | gB2/PR8-ISCOM ™ | 10 μg |
| 5 | gB2 + ISCOM ™-matrix | 10 μg |
| 7 | gB2 | 10 μg |
| 9 | Control | 10 μg mice immunized with irrelevant antigen |

The mice were immunized i.n. twice (week 0, 9) and from the lungs, secretions were extracted 2 weeks after booster (day 77) from four mice per group. Lungs, upper respiratory tracts, intestines and genital tract from the remaining mice were extracted to obtain the organ secretion on day 113 and the secretion were analyzed for secretory IgA. The extracts from these organs were recovered as described in Example 2. The antibody responses were tested in ELISA as described in Example 2. The antibody responses in organs were tested in ELISA as described in Example 2. Antibody responses in organs were tested on individual samples from day 77. Samples from day 113 were tested as a group sample from each organ and group respectively.

Results

IgA-antibody Response, against qB2 in Lung Secretions

Two weeks after booster, gB2 in free form (group 7) did not induce an antibody responses in ELISA (FIG. 11A). The highest IgA ($10^{4.8}$) titres were obtained two weeks after i.n. booster (day 77) with mice in group 2, i.e. mice immunized i.n. with gB2/PR8-ISCOM™ i.e. with PR8 envelope proteins as target seeking molecules gB2-ISCOMs™ without a target seeking molecule ($10^{2.4}$)as well as gB2 mixed with ISCOM™-matrix ($10^{3.7}$) also induce relatively high antibody titres in the lung secretion although with 10- and 100-fold respectively lower titres.

On day 113, the antibody response in lung secretion from the remaining mice was measured. The antibody titres had decreased considerably but the same pattern in the antibody response was observed as on day 77.

Secretory IqA-response in Other Mucous Membranes than the Administration Site

In FIG. 11B the IgA-response after two immunizations against gG2 in different secretions (pooled groups) was demonstrated, i.e. in the upper respiratory tract, the genital tract and lungs. Relatively high IgA-responses were obtained against gB2 in genital tract after immunization with gB2-ISCOMs™, gB2/PR8-ISCOMs™ and gB2 mixed with ISCOM™-matrix. In the upper respiratory tract the Iga-response after immunization with gB2 supplemented with ISCOM™-matrix was lower than that after immunization with gB2-ISCOMs™ and gB2/PR8 ISCOMs™.

Antibody Response against PR8

Against the PR8 antigen included in the gB2/PR8-ISCOM™ formulation high levels of antibody were observed both in secretion and serum. Mice in the control group did not have detectable IgG or IgA antibody responses in serum or in lung secretion (data not shown).

Serum Antibody Response to gB2

The total IgG serum antibody response to gB2 two weeks after the second i.n. immunization (day 77) (not shown). The highest total serum antibody responses measured in ELISA day 77 was induced by gB2/PR8-iscom and gB2 complemented with iscom-matrix in separate entities. GB2 alone (7) also induced by i.n. administration clear-cut specific serum antibody titres although a 10-fold lower titre or more compared to iscom matrix and iscom formulations. By day 113 post vaccination the total serum titres had increased or remained at the same level except for the preparation with GB-2 alone the serum titres of which had decreased considerably.

The IgG1 serum antibody response was highest for the gB2/PR8 construction with a titre of $10^{6.5}$ compared with $10^{5.2}$ for the ISCOMs™-matrix gB2 formulation and $10^{5.3}$ for gB2 iscom. The formulation with gB2 alone induced an almost 100-fold lower serum titre.

By day 113 the IgG1 titres induced by the ISCOM™ or ISCOM™ matrix formulation had increased or remained above $10^6$ except for gB2 alone which titre decreased a 10-fold (data not shown).

The IgG2 serum antibody response was highest for the gB2-matrix ($10^{5.0}$) and gB-2/ISCOM™ $10^{4.8}$ by day 77 and approximately a 10-fold lower for gB2-iscoms and gB2 alone (FIG. 11C).

By day 113 the IgG2 serum antibody titres had increased for the ISCOM™ and ISCOM™ matrix formulations a 10-fold or more while the serum IgG2 antibody titres for GB-2 alone had decreased considerably.

Conclusion

Serum Antibody Response

The gB2 protein by its own induces serum antibody responses in both IgG1 and IgG2a subclasses, which were highest day 77. Five weeks after the second i.n. immunization (day 113) the IgG1 and IgG2a antibody titres had decreased considerably. In contrast, mice immunized with gB2-iscom and gB2/PR8-ISCOM™ formulations and ISCOM™-matrix formulations increased a 10-fold or more the total as well as subclass IgG1 and IgG2a serum antibody titres. These results clearly indicate that the ISCOM™ and ISCOM™-matrix formulations following mucosal administration induce significant prolongation of the immune response compared to the non-adjuvanted gB2.

The gB2/PR8-ISCOMs™ and gB2/ISCOM™-matrix formulations are more efficient with regard to induction of IgG2a response than the other tested formulations.

The gB2 alone appears to have an inborn capacity for immunomodulation with capacity to induce both IgG1 and IgG2a antibody responses. The latter is considered to require an interferon-γ-production. These results are in contrast to hose of gD2 in Example 6 which show that gD2 is poorly immunogenic by itself by i.n. route and does not have the capacity to modulate as IgG2a response. Our results indicate that gB2 may be useful in modulation of immune responses perhaps even for bystander proteins.

gB2 has a property of self-aggregating and aggregate and associate with Quillaja components (not shown), which partly explain the difference between gB2 and gD2, the later being very hydrophilic and having no tendency for aggregation or spontaneously by associating with Quillaja or Quillaja components.

EXAMPLE 6

This example shows that influenza virus antigen (PR8) incorporated into ISCOM™ acts as a target seeker to lymphoid systems in several mucous membranes, i.e. lungs, upper respiratory tract and genital tracts. The passenger antigen consists of gD2 from Herpes simplex 2 (HSV-2) causing disease in the genital tracts and a vaccine against HSV-2 is therefor desired.

gD2 is lipidated with the same method as OVA in Example 2. The ISCOMs™ were prepared in the same way as in Example 2 and 5. Matrix was obtained from Advet, Luleå, Sweden.

| Group | Immunogen | Dose of antigen |
| --- | --- | --- |
| 3 | gD2-ISCOM ™ | 10 µg |
| 4 | gD2/PR8-ISCOM ™ | 10 µg |
| 6 | gD2 + ISCOM ™-matrix | 10 µg |
| 8 | gD2 | 10 µg |
| 10 | Control | |

The mice were immunized in accordance with the same schedule described in Example 5 for gB2. The antibody response was tested in ELISA which is described in Example 2. The antibody response in organs were tested in individual samples on day 77. The samples from 113 were tested as a group sample form each organ and each group respectively.

Results

Secretory IqA-response in Lung Secretions after i.n. Immunization with Different gD2 Formulations FIG. 12A shows that the highest IgA-response in lung secretions was obtained in mice in groups 3, 4 and 6, i.e. mice that have been immunized i.n. with gD2-ISCOM™, gD2/PR8-ISCOM™ and gD2 mixed with ISCOM™-matrix respectively.

Secretory IqA-response in Mucous Membranes Far from the Site of Administration

FIG. 12B shows that the secretions of the genital tract induce gD2-iscom with a target seeking molecule (gD2/PR8-ISCOMs™) efficient IgA-response after two i.n. immunizations as opposed to other formulations with ISCOMs™ or ISCOM™-matrix.

Antibody Response against PR8

High antibody responses against PR8, part gD2/PR8-ISCOM™ formulations were observed both in secretion and in serum.

Serum Antibody Response to gD2

The serum antibody response to gD2 two weeks after the second i.n. immunization (day 77) is shown in FIG. 12C. gD2 is different from gB2 Example 5 in the sense gB2 aggregates and is comparatively immunogenic by itself without added adjuvants also shown in Example 5. This property also indicate and "inborn' immunomodulating capacity. The gB2 is in contrast to gD2 efficiently associated with ISCOM™ and ISCOM™-matrix to form aggregates even with a low ratio Quillaja/gB2. In contrast, gD2 is hydrophilic, monomeric and poorly immunogenic without complementation with adjuvant.

The highest total serum antibody response measured in ELISA was day 77 induced by gD2/PR8-ISCOM™ by gD2-ISCOMs™.

Most striking is that gD2 by itself (8) (FIG. 12C) in contrast to gB2 alone did not induce a measurable serum antibody response by i.n. administration. The IgG1 serum antibody response was highest for the gD2-ISCOM™ (3) and gD2/PR8-ISCOM™ (4) being a 10-fold and significantly higher than that for gD2/ISCOM™-matrix formulation (FIG. 12C). By day 77, the IgG2a serum antibody titres were considerably or a 300-fold higher for gD2/PR8-

ISCOMs™ than for gD2/-ISCOMs™ than for gD2-iscoms or a 500-fold higher than for the gD2/ISCOM™-matrix formulation.

By day 113 post first immunization, the total serum antibody response remained at about the same level as for day 77 for gD2-ISCOM™ and gD2/PR8-ISCOMs™ and the gD2 matrix formulations had also reached the levels of the iscom ($10^{4.8}$). At day 113, the IgG1 levels were similar for the ISCOM™ and ISCOM™ matrix formulations. But the IgG2a response to gD2 was a 10-fold higher in serum of mice immunized i.n. with gD2/PR8 ISCOM™ formulation i.e. $10^{4.1}$ than for gD2-ISCOMs™ without targeting protein and gD2 complemented with ISCOM™-matrix.

Conclusion

The gD2 protein by its own has, in contrast to gB2 in Example 5, a poor capacity to induce and modulate towards an immune response encompassing the capacity to produce specific IgG2a response. The latter is considered to reflect the participation of a Th1 type of response with an interferon-γ-production. The gD2/PR-ISCOM™ i.e. an ISCOM™ with a mucus guiding or targeting molecule showed a potent capacity to induce serum antibody response by i.n. route a very strong and clear-cut capacity to induce (modulate) to an IgG2a serum antibody response considered an important type of immune response for protection against herpes virus infections.

Most importantly, this example shows that the combination in an ISCOM™ with a passenger antigen (gD2), by its own immunologically rather inactive (inert), with immunologically active protein molecules (PR8-molecules) acting as molecules actively targeting the immune system after mucosal mode of administration and activating the immune system is converting the passenger antigen to a protent mucosal antigen in this case a highly immunogenic gD2-molecule.

EXAMPLE 7

Mycoplasma mycoides subspecies mycoides (MmmSC) is the causative organism of Contagious Bovine Pleuropneumonia (CBPP) which is responsible for great economic losses in cattle livestock. It is spreading in many African countries and in some countries in Asia as well as in the south of Europe i.e. in Portugal and Spain. The extended latency period during which infected cattle show no symptoms, makes it difficult to eradicate, and effective control measures against the disease is of paramount interest. Since the beginning of the nineteenth century, vaccination efforts have been carried out encompassing a variety of attenuated vaccine strains and inactivated vaccines (Walker, J., Ann. Rep. Dept. Agric. Kenya, p. 240–243, Nairobi, 1929; Curasson, G. Bull. Acad. Vet. Fr. 5, 179–184, 1932; Hudson, J.r., Australia Vet. J. 41, 43–49, 1965).

Still, an efficient vaccine is lacking inducing long-lasting protectgnito natural infection taking place via the respiratory tract. In the present example we analyze the immune response after i.n. administration of ISCOMs™ containing the *M. mycoides* antigens released from the microorganism by detergent solubilization.

Materials and Methods
Chemicals and Solutions
PBS as in Example 2
Saponin (Sigma No S-1252) or QA (Advet AB, Stockholm, Sweden).
See Example 2.

The detergent octylglucaside (OG) was purchased from Boehringer Mannheim, Germany. It was used as a 10% stock solution in water.

The detergent MEGA-10 was obtained from Bachem, Bubendort, Switzerland.

Quil A (Spikoside), was from Advet AB (Stockholm, Sweden) (Example 2).

The lipids cholesterol and 1-3-Phosphatidyl choline from egg yolk (both grade 99%–100%), Thyroglobulin, Bovine serum albumin (BSA), the substrate DAB, Biotinylated lectins; Con A, WGA, SBA, UEA, and Streptavidin conjugated with HRP were from Sigman (St. Louis, Mo. USA).

Rabbit anti-mouse immunoglobulins labeled with HRP were from Dakopatts (Copenhagen, Denmark).

TMB reagent, $H_2O_2$ and coating buffer tablets were purchased from SVANOVA Biotech (Uppsala, Sweden).

Tween-20 was from Merck (Darmstadt, Germany).

Mycoplasma

MmmSC strains Afade and Tl/44 were supplied by Pathotrop laboratory, CIRAD-EMVT, Montpellier, France.

Formation of ISCOMs™

Whole MmmSC Cell ISCOMs™ were prepared as described for PR8. Briefly, to a mycoplasma sample of approximately 5 mg in a volume 5 ml the detergent MEGA-10 or OG was added to a final concentration of 2% and left 2 hours at room temperature. The solubilized material (5 ml) was layered on top of 10% sucrose in PBS in a volume of 2 ml containing 0.5% MEGA-10 or 0.5% OG with a layer of 30% sucrose in PBS underneath. The solubilized proteins were separated from insoluble material by centrifugation at 40,000 rpm for 1 hour at 20° C. in a TST 41.14 rotor. The top fractions consisting of the sample volume and the 10% sucrose layer were collected, and cholesterol, phosphatidyl-choline and Quil A were added and mixed in a proportion w/w of 10:2:1:20 and extensively dialyzed against PBS overnight at room temperature and for further 48 hours in cold room. The formed ISCOMs™ were further purified from unincorporated proteins by sedimentation through a double layer of 10% and 20% sucrose at 39,000 rpm for 19 hours at 10° C. in a TST 41.14 rotor. The sedimentated ISCOMs™ were suspended i PBS and kept at −70° C. until use.

I.n. Immunization of Mice

I.n. administration of MmmSC of strain *Afade iscoms* were carried out in mice by installation of antigens into the nostrils of animals under anaesthesia (Methophane). 12 Balb/c female mice 8 weeks cold were divided into 4 groups each of 3 animals. The mice in group 1, 2 and 3 received 3, 10 and 20 μg respectively of ISCOM™ vaccine i.n. twice 7 weeks apart. Group 4 served as non-immunized control animals. Animals were bled at 2, 4 and 7 weeks after the initial dose and 2 weeks later after the booster dose another bleeding was taken.

Preparation of lung extracts was done as described in Example 2.

ELISA for IgA in Blood and in Lung Extract

ELISA plates were coated with 100 μl of MmmSC cells of strain Afade at a concentration of 0.4 μg/well in coating buffer (50 mM carbonate buffer pH 9.6) and incubated at +4° C. for overnight or more. All washing (×3) were made with phosphate-buffered saline (150 mM, pH 7.5) containing 0.2% Tween −20 (PBS-T). The wells were blocked with 200 μl of 2% BSA in PBS-T for 1 hour at room temperature under shaking. 100 μl of lung suspension supernatants or serum in blocking buffer were 2-fold diluted and incubated at room temperature for overnight. 100 μl of 1:10.000 dilutions of HPR-Strpt-avidin conjugate in blocking buffer were added and incubated for 1 hour at room temperature. The enzyme reaction was visualized by addition of 200 μl substrate buffer (TMB, $H_2O_2$) for 15–20 minutes at room temperature after which the reaction was stopped by 50 μl of 2 M H$_2$SO$_4$ and the absorbance was measured at 450 nm with a Titertek Multiscan spectrophotometer. Lung suspension and serum from negative control animals were used as background and for calculating the cut-off.

Western Blots

Western Blots were done according to Towbin, H., Staehlein, T. and Gordin, J., Proc. Natl. Acad. Sci. USA 4350–4354, 1979. using nitrocellulose paper from Schleicher and Schull, Germany. Isocm and whole MmsmSC antigens were resolved in a 12% SDS-Gel.

Results

Total serum antibody responses were measured by ELISA. A steady rise of antibody was obtained until week 4. After the animals were boosted a 3- to 5-fold increase of serum antibody levels were recorded after 2 weeks. Antibody responses increased with increasing doses, reading end point titres of about $10^6$ (FIG. 13A).

IgA responses in serum (FIG. 13B) and lung secretion (FIG. 13C) extracts were measured by ELISA. Secretory IgA levels in dilutions up to 1:8000 were detected. About similar IgA titres were observed in serum. The IgA titres increased with increasing doses.

In WB lung secretion from mice with i.n. immunized with ISCOMs™ detected about 10 polypeptide bands ISCOMs™ and more than 20 bands were detected by serum of the same mice. Serum from s.c. immunized mice detected some different proteins (FIG. 13D) than serum from mice immunized by the i.n. route. The lung extract (A) detected about 10 bands which all except two bands were detected by serum from i.n. immunized mice (see arrow). It is likely that antigens detected by the i.n. route are glycolipids indicated by the fluffy not discrete appearance which is typical to carbohydrate structures. This means that the i.n. immunization opens an additional scenario for immunization against carbohydrates for immunization with antigens which are not immunogenic by other modes of administrations.

Conclusion

The results show that the mycoplasma antigens act both as target seeking molecules and as passenger antigens since about ten antigens as disclosed by Western blot (WB) induce IgA responses. Of particular interest and unforeseen is that the repertoire of antigens detected in WB were different using serum from mice immunized i.n. from that using serum from mice immunized i.n. from that using serum from mice immunized s.c. This means that i.n. route can be used to induce immune response to antigens which a parenteral route would not do. Many of the antigens detected as bands in WB by serum from mice immunized i.n. were not discrete as those detected by serum from mice immunized by the s.c. route. This phenomenon strongly suggest that carbohydrate structures are detected by the i.n. route and that he i.n. route should be used as an alternative to inducing immune response to antigen or antigenic determinants not recognized by the parenteral (s.c.) mode of immunization e.g. carbohydrate structures. Of utmost importance is the induction of immune response against polysaccharides on various bacteria like Pneumococus pneumonia, Haemophilus influenzae and Streptococcus pneumonia.

EXAMPLE 8

Protective Mucosal Immunity Induced in Lambs by Oral Administration of Inactivated Rotavirus Adjuvanted with ISCOM™-Matrix Introduction Rotaviruses are recognized as the major cause of severe diarrheal disease in children younger than 5 years of age in both developed and developing countries, resulting in some 870,000 deaths and several million cases of severe diarrhea in this age group annually. They are of similar significance as a cause of neonatal diarrhea in many domesticated animal species. With the exception of a study describing the primary mucosal immune response in rabbits, there has been little detailed characterization of this response.

In this example, we examine the hypothesis that a mucosal immune response as well as a systemic response can be induced following oral immunization with inactivated bovine rotavirus and ISCOM™-matrix which would result in a protective immune response to subsequent live virulent virus challenge. It should also be emphasized that the lambs in this experiment (6 days old) are very young and that they are in an age when they are less immunocompetent than adults (Ridge, J. P., Fuchs, E. J., Matzinger, P. Science 271, 1723–26, 1966; Billingham, R. E., Brent, L., Medawar, P. B. Nature 172, 603, 1953; Bandeira, A., coutinho, A., Carnaud, C. Jacquemart, F, Forni, L. proc. Natl. Acad. Sci. USA, 86, 272, 1989; Schurmans et al., J. Immunol 145, 2454, 1990) and during a period the maternal antibodies are expected to prevail which makes the successful vaccination even more difficult. For that reason it would be even more interesting to explore whether the combination of an oral mucosal administration with a modern adjuvant system will overcome the problem of neonatal immunization.

Material and Methods

Viruses

The vaccine virus was a bovine rotavirus strain, UK, gown in MA 104 cells. The infectivity titre, before inactivation was $10^{6.8}$ fluorescent focus units (ffu)/ml,and after treatment with a 5% (v/v) of a 0.1 M binary ethylene imine (BEI) solution at 37° C. for 24 hours, no infectivity was detected. Virulent lamb rotavirus strain K923 passages in gnotobiotic lambs was used for challenge. Each lamb received $10^{8.5}$ ffu suspended in 5 mls of sterile PBS.

Experimental design.

Lambs were born and maintained in gnotobiotic isolator units. At 6 days of age, lambs were orally inoculated with a mixture of either PBS and 500 μg of ISCOM™ matrices (Advet, Uppsala, Sweden) (PBS/ISC; n=6), inactivated bovine rotavirus (strain UK) and 500 μg of ISCOM™ matrices (RV/ISC; n=5), or inactivated bovine rotavirus alone (RV; n=3). Lambs were challenged 21 days later with live virulent bovine rotavirus (strain K923) and killed 1–2 weeks after challenge.

Sample Collection and Analysis

Blood for serum and nasal secretions were collected at initial immunization and then at regular intervals to determine the levels of specific and total IgA and IgG antibodies by ELISAs and neutralizing titres by virus neutralization tests. Faecal samples were collected daily after immunization and challenge until rotavirus excretion was no longer detected. Rotavirus excretion was assuaged by detection of double-stranded RNA by sodium dodecyl sulphate-polyacrylamide gel electrophoresis (SDS-PAGE). PBLs were collected at initial immunization and then at weekly intervals to determine the numbers of specific IgA and IgG secretin cells by ELISPOTs and the distribution of lymphocyte subpopulations by FACS analysis. Lambs were killed 1–2 weeks after challenge and lymphocyte populations isolated from Jejunum Peyers patches (JJPs), Ilium Peyers patches (IPPs), Mesenteric lymphnodes (MLNs) and small intestine Intestitiel epethelial lymphocytes and Lamina propria lymphocytes (IEL and LPL). Numbers of specific IgA and IgG producing cells in JPPs, MLNs and LPLs and were determined by ELISPOT. Lymphocyte subpopulations were analyzed by FACS. ELISPOT. Lymphocyte subpopulations were analyzed by FACS. Cytokine expression (γ-IFN, IL-2, and IL-4) in MLNs and JPPs was visualized by RT-PCR and hybridization. The levels of specific and total IgA and IgG antibodies and neutralization titres in intestinal secretions were determined using intestinal mucus.

Lymphocyte Isolation

Peripheral blood lymphocytes were collected an processed as previously (Puri, N. K., MacKay, c. R., Brandon, M. R. Immunology 55, 725–33, 1985) described and resuspended at the appropriate concentration in complete IMDM containing 1 mM glutamine, 100 units/ml penicillin, 0.1 mg/ml streptomycin, 2 µg/ml amphotericin B (Sigma, St. Louis, USA) and processed as previously described. The lymphocytes were finally suspended at the appropriate concentrations in complete IMDM. Pieces of small intestine were collected and processed with minor modifications of previously described methods. Small intestine was cut into 10-cm segments, inverted, washed three times at 37° C. with gentle stirring in HBSS without calcium and magnesium containing 2 mM EDTA to free epithelial cells and intraepithelial lymphocytes. The tissues were washed in RPMI 1640 and placed in RPMI containing 1 mM glutamine, 100 units/ml penicillin, 0.1 mg/ml streptomycin, 2 µg/ml amphotericin B, 5 µg/ml gentamycin, 80 units/ml collagenase XI (Sigma), 0.1 mg/ml deoxyribonuclease type V (Sigma), and 10% FCS at 37° C. to allow the lamina propria lymphocytes to be removed. The IEL and LPL suspensions were passed through sterile glasswool columns, layered onto an equal volume of Lymphoprep® and spun down. Lymphocytes were harvested at the interface and washed twice in HBSS containing 1 mM glutamine 100 unit/ml penicillin, 0.1 mg/ml streptomycin, 2 µg/ml amphotericin B., and 2% FCS before being suspended at the appropriate concentration in complete IMDM.

Assays

Virus neutralizing assays. Virus neutralizing assays for bovine rotavirus strain UK and lamb rotavirus strain K923 were performed in microtitre plates and the endpoints or virus neutralizing titre (VNT) were determined by 60% reduction in fluorescent focus units.

ELISAs. Specific-rotavirus ELISAs utilized microtitre plates, (Nunc, Maxisorb), coated with a rabbit antirotavirus capture serum, lamb RV K923 and uninfected MA 104 extracts as negative antigens binding control, the test and control samples, horseradish peroxidase-conjugated donkey anti-sheep IgG (The Binding Site) or mouse anti-bovin IgA, with the color developed by adding substrate $H_2O_2$ and o-phenylenediamine dihydrochloride to the bound peroxidase. The reaction was stopped with 2 M $H_2SO_4$, and the absorbance measured at 490 nm. The net absorbance was calculated was calculated by subtracting the values in the negative wells from the corresponding K923 wells.

Total isotype ELISAs utilized microtitre plates coated with rabbit anti-sheep Igs (DAKO) or pig antisheep IgA, test samples, diluent, and control samples, horseradish-peroxidase conjugated rabbit anti-sheep IgG (Pierce) or mouse anti-bovin IgA, with the same color development as described above. OD values in the diluent wells were subtracted from the corresponding test wells. For each ELISA a standard was used: a hyperimmune lamb serum for the IgG concentration of 9,600 mg/L for the total IgG ELISA; a batch of IgA, purified from clarified lung fluid of a sheep infected with an bovine retrovirus (Jaagsiekte) (JSRV) for the total IgA ELISA. Each standard was assayed at eight 2-fold dilutions, and the net absorbance as a function of arbitrary antibody units or mg per ml respectively was fitted to a lin-log sigmoid curve. In each case the resulting standard curve had a fit of r>0.95. The resulting parameters were then used to interpolate antibody units or concentration (mg/ml) for each of the test samples, taking into consideration the dilution factor at which each sample was tested. Specific and total ELISA results were combined and expressed in units/mg of IgG or IgA.

ELISPOTs. Isotypes anti-rotavirus ELISPOTs utilized microtitre plates, (Nunc, Maxisorp), coated with a mouse anti rotavirus capture serum, sucrose-purified rotavirus strain UK as antigen at a concentration of 5 µg/ml, the PBL suspension ($5\times10^5$ cells/ml), horseradish perosidase-conjugated rabbit anti-sheep IgG (Pierce) or mouse anti bovine IgA, with the spots made visible by adding substrate $H_2O_2$ and 3-amino-3-ethylcarbazole (AEC) to the bound peroxidase. The reaction was stopped, when spots were visible, by flicking off the substrate. Spots were counted (mean of 6 replicates) and expressed as spot forming cells (SFC)/$10^6$ lymphocytes.

FACS analysis. Lymphocyte subpopulations were determined with a panel of mouse monoclonals specific for bovine CD4 (17D) (MacKay, C. R., Hein, W. R., Brown, M. H., Matzinger, P. eur. J. Immunol. 18, 1681–8, 1988; Maddox, J. F., MacKay, C. R., Brandon, M. R. Immunology 55, 739–48, 1985), CD8 (7C2) Maddox, J. F., MacKay, C. R., Brandon, M. R. Immunology 55, 739–48, 1985), γσTCR (86D), light chain (VPM8) (Puri, N. K., MacKay, C. R., Brandon, M. R. Immunology 55, 725–33, 1985), and CD45R (73B) (MacKay, C. R. Marston, W. L., Dudler, L. J. Exp. Med. Med. 171, 801.17, 1990). A second antibody, fluorescein-labelled rabbit anti-mouse IgG (DAKO), was applied and cells were scanned and counted with a FAScan® (Becton-Dickinson Ltd.).

Results

After Vaccination

The levels of specific IgG antibodies in blood after immunization was higher for the animals vaccinated with RV iscom matrix (FIG. 14A). Significantly higher percentages of CD4+ cells at 21 days after immunization in both Rv-vaccinated groups (FIG. 14B). CD45R+ cells (FIG. 15C) were only recorded in the RV/ISC-matrix vaccinated group in blood most important from the point of view that these cells are memory cells and constitute a basis for a fast response for a subsequent infection with rotavirus. Interestingly, the PBS/ISC-matrix, i.e. no-antigen group showed no increase of CD4+ cells but did show a significant higher percentage of γσ TCR-cells (not shown).

After Challenge Infection

It is expected that after challenge infection animals respond immunologically. However, a solitary immunization orally has not before, with non-live (non-replicating) rotavirus formulation, induced protection to infection or to disease. The protection to disease is dependent on I. The existing immune defence II on the readiness of the immune system to respond fast against the infecting agent in this case RV. This readiness is dependent on memory cells i.e. the CD45R+ cells which were induced by RV ISCOM™-matrix which were detected day 21 after vaccination and before challenge infection (FIG. 14C). The read-out of the readiness against infection is the excretion of the infectious agent in this case the RV. It should be noticed that this experiment is the first of this kind in a ruminant with very complicated alimentary system. Therefore, to reach optimal conditions with regard to dose of adjuvant (ISCOM™-matrix) and antigen etc. a series of experiments is required. However, the very promising prospect for a successful vaccine based on the ISCOM™ and ISCOM™-matrix technology is strongly indicated.

After challenge all lambs excreted rotavirus. Both RV-vaccinated lambs excreted virus for a shorter prior than the controls namely 5–6 days, 6–7 days and 8–9 days respectively, however this was only significant (p=0.027) in the RV-ISC-matrix vaccinated group strongly indicating the potential for developing an effective vaccine (FIG. 14C).

As expected, all lambs had after challenge specific IgA and IgG antibodies in serum, nasal secretions, and gut scrapings and antibody secreting cells in blood and gut associated lymphoid tissues (MLNs and JPPs) after challenge.

Notably, the RV/ISC-matrix vaccinated groups had significantly increased numbers of specific IgA (FIG. 14E) and IgG producing cells in blood indicating a priming effect of the vaccination. The priming effect is dependent on the development of memory cells. The numbers of specific IgG producing cells was also significantly higher compared to the non-adjuvanted RV-vaccinated group. After challenge, no differences were found in specific IgA or IgG producing cells in the GALT between the three groups. The specific IgG response was similar to the specific IgA response.

Neutralizing antibodies against UK and K923 were detected in all groups in serum. After challenge, all lambs had an increase in $CD4^+$ cells and in the PBS/ISCOM™-matrix and in the RV-vaccinated groups the $CD45R^+$ cells increased to a similar level as observed in the RV/ISC-vaccinated group before challenge.

Discussion

It is surprising that a single oral dose of inactivated non-replicating rotavirus adjuvanted with ISCOM™-matrix resulted in a significantly reduced period of virus excretion upon subsequent challenge with live replicating virus. A significantly reduced period of virus excretion was only observed in the RV/ISC-vaccinated group and not in the RV-vaccinated groups, although the small number of lambs in this group limits the statistical analysis. Characteristics of the immune response of primed animals to virus challenge included increased levels of specific IgA and IgG antibodies in nasal and intestinal secretions and, in the RV/ISC-vaccinated group, increased numbers of circulating specific IgA and IgG producing cells.

It is also surprising that RV-adjuvanted with matrix with only one dose would prime an immune response and significantly reduce that the infectious period in view of the results of Mowat (Mowat et al., Immunology 72, 317–322, 1991) showing in mice that several immunizations were required to induce IgA response following oral administration of OVA.

Conclusion

It is unexpected that a clear-cut priming would be achieved by oral administration of one dose of Rotavirus adjuvanted with ISCOM™-matrix or any non-replicating vaccine in view of the young age of the animals i.e. one week when they still are in the neonatal period and not immunocompetent as adults and also in view of the difficulty to induce immune response with one immunization by the oral route. This is particularly difficult in view of the complicated alimentary system of ruminants. It is likely that the rotavirus or parts of the rotavirus in this respect is suitable for use as a mucosal target seeking device suitable to facilitate the immunization with other antigens as well in the ISCOM™ and ISCOM™-matrix formulations. These results implies the possibility to successfully immunize the animals via mucosal immunization during the neonatal period when maternal antibodies are present. The increased number of CD45R+ cells induces by RV/ISCOM™-matrix indicate an increased number of memory cell which can rapidly be recruited by an infection explaining the shortened period for virus excretion following oral challenge and thereby eliminating or decreasing the risk for development of disease.

EXAMPLE 9

Introduction

Respiratory syncytial virus (RSV) is a most important causative agents of viral lower respiratory tract infection in infants and young children world wide. It causes an estimated 91,000 hospitalizations and 4,500 deaths annually in the United States alone. A closely related virus is bovine respiratory syncytial virus which is an important respiratory virus in young calves. Both national and international health organizations view the development of a vaccine to control the virus as a priority in the prevention of morbidity and mortality (Murphy, B. R., Prince, G. A., Walsh, E. E., Kim, H. W., Hemming, V. G., Rodriguez, W. and Chanock, R. M. J. Clin. Microbiol. 24, 197–202, 1986). So far, attempts to develop an RSV vaccine have been unsuccessful and great precautions have to be taken because of the earlier failure with a formalin-inactivated human respiratory syncytial virus (HRSV) vaccine which was evaluated in infants and young children in the 1960s. It not only failed to induce resistance to infection and disease, but also caused an aggravated form of lower respiratory tract disease.

RSV initiates its infection via the respiratory mucosal surface. For this reason a vaccine inducing immune response in the mucus of the respiratory tract is of utmost interest which is most likely to be evoked by i.n. immunization. Mucosal mode of immunization has advantages over parenteral administration by the potential of inducing both local and systemic immune responses, increasing safety and minimizing adverse effects, reducing the need for personnel and equipment for the vaccination and so on.

The present aim was to compare antibody responses with regard to IgM, IgG isotypes, IgG subclasses and secretory IgA responses in lungs and other mucosal surfaces after intranasal and subcutaneous administrations, and to investigate the possibility of developing an RSV ISCOM™ vaccine based on intranasal administration.

Materials and Methods

Chemicals and Reagents

The Non-ionic Detergent n-octyglucosid (1-o-octyl-glucopyranosid, OG) Was Obtained from Boehringer (Mannheim, GmbH, FRG)

Quillaja "Spicoside" was obtained from Iscotec AB (Lule a, Sweden).

Goat anti-mouse IgM, IgG1, IgG2a, IgG2b and IqG3 were obtained from Nordic (Tilburg, The Netherlands).

Biotinylated goat anti-mouse IgA was obtained from Southern Biotechnology Associated, Inc. (Birmingham, USA).

Peroxidase-conjugated rabbit anti-goat immunogloblins and HRP streptavidin were obtained from Dakopatts (Glostrup, Denmark)

Preparation of RSV ISCOM™ and Inactivated RSV

RSV ISCOMs™ were prepared from two different preparations of virus. The virus was propagated in vero cells. After the virus was harvested cell debris was removed by centrifugation. The virus was sedimented to a pellet by ultracentrifugation and further the purified by centrifugation through a 10 to 50% sucrose gradient. The preparation procedure and biochemical characterization of ISCOM™ were carried out as previously described. Briefly, the virus protein concentration: (1.80 mg/ml) was solubilized with OG at a final concentration of 2% (W/V) for 1 hour at 37° C. under constant agitation. The solubilized virus was applied onto a discontinuous sucrose gradient of 2 ml 20% sucrose layer containing 0.5% OG, over a cushion of 50% sucrose. After centrifugation at 40,000 rpm in a Kontron TST-41 rotor for 1 hour at 4° C., the sample volume plus the 20% sucrose layer containing viral proteins were collected, and extra lipids i.e. cholesterol and phosphatidycholine and Quillaja (spicoside, Lulea, Sweden) were added in proportions of 1:0.5:0.5:3.5 (W/W). After extensive dialysis against 0.15M ammonium acetate for 72 hours 4° C., the ISCOMs™ were purified by centrifugation through 10% sucrose at 40,000 rpm in Kontron TST-41 rotor for 18 hours at 10° C. The pellets containing RSV ISCOMs™ were resuspended in 200 µl PBS. Presence of ISCOMs™ were confirmed by electron microscopy and as described in Example 2.

The protein pattern of the ISCOMs™ was determined by electrophoresis and Western blotting. The Quillaja concentration was measured by HPLC. The ratios between Quillaja and protein in these final iscom preparation is 5 mg Quillaja/1 mg iscom.

The inactivated RSV was prepared by adding 0.5% (W/V) of B-propiolactone to the virus solution and the reaction was kept at 4° C. for 7 days to inactivate the viruses.

Mice

Female Balb/C mice, 8–12 weeks of age, were obtained from the National Veterinary Institute, Uppsala, Sweden. The mice were screened for viral, bacterial and mycoplasma infections and kept in accordance with the national guidelines.

Immunizations

Seven groups of mice (A through G), each consisting of seven Balb/C mice were immunized twice 6 weeks apart. Mice in different groups were immunized as follows:

Group A, 5 µg/mouse with ISCOM™ I intranasally (i.n.).
Group B, 1 µg/mouse with ISCOM™ I subcutaneously (s.c.).
Group C, 5 µg/mouse with ISCOM™ II i.n.
Group D, 1 µg/mouse with ISCOM™ II S.C.
Group E, 4 µg(i.n.)+1 µg(s.c.)/mouse with iscom.
Group F, 500 µl/mouse with inactivated RSV s.c. The preparation contains the same amount of the fusion protein as in the ISCOM™ preparations measured by an immunodot assay. Group G, non-immunized control group.

For intranasal immunization, 5 µg ISCOMS were suspended in a volume of 20 µl while the subcutaneous dose was suspended in a volume of 200 µl. I.n. immunizations were carried out under anaesthesia (as described in Example 2).

Blood samples for serological evaluations were taken at the 2nd and the 5th weeks after the first vaccination, as well as the 1st and 3rd weeks after the booster. Lungs for antibody extractions were taken 2 weeks after the booster. Two mice from each group were sacrificed and the lungs were removed. The IgA was extracted as described in Example 2.

Enzyme Immunoassays

Enzyme-linked immunosorbent assays (ELISA) for serum IgM and IgG antibodies against RSV were carried out in microtiter plates (Nunc, Roskilde, Denmark) which were coated with 200 ng purified HRSV per well in 100 ul 50 mM carbonated buffer, pH 9.6, and kept at 4° C. overnight. All washings were carried out with phosphate buffered saline containing 0.2% Tween 20 (PBS-Tween). All incubations were done at room temperature for 60 minutes under constant shaking. The mouse sera were titrated in two-fold dilutions. The enzyme reactions were visualized using tetramethylbenzidine (0.19 mg/ml) and $H_2O_2$ (0.006%) in 0.1M acetate buffer pH 6.0 and the optical density was measured at 450 nm with a Titertek Multiscan Spectrophotometer (Flow Laboratories, Irvine, Scotland). ELISA for mouse IgG1, IgG2a, IgG2b and IgG3 subclass determination were carried out by a similar procedure, using goat anti-mouse IgG subclass and a rabbit anti-goat HRP conjugate. Secretory IgA (sIgA) levels to HRSV in mouse lung extracts were measured by an ELISA with slight modifications. Microplates were coated with purified HRSV, 400 ng per well, 100 ul coating buffer. Two-fold serial diluted lung extracts were added to the wells. After overnight incubation at RT and subsequent washing with PBS-Tween 20, 100 ul biotinylated goat anti-mouse IgA was added to each well.

After 1 hour incubation at RT, HRP conjugated streptavidin was added and incubated for 1 hour at RT, thereafter the plates were washed and substrate was added. The enzymatic reaction was stopped after 15 minutes by adding 50 ul 2M $H_2SO_4$. The optical density was measured at 450 nm.

Titers and Calculations

IgM, IgG and IgA were tested on individual sample. due to the limited amount of serum which could be collected from each mouse, IgG subclasses were run on serum pools. The titers are expressed as reciprocal end point dilutions.

Statistical Analysis

ELISA titers for IgM and IgG are expressed as geometric means of arithmetical values and were compared with respect to the incidence and level of serum antibody by Mann-Whitneys U-test. Confidence limits of 95% for ELISA titers were calculated using Minitab 10 computer software (Minitab Inc., PA, USA)

Results

Serum IgM Response

Significantly ($P<0.01$) higher serum IgM responses were induced in all groups with ISCOM™ immunized mice (groups A, B, C, D and E) compared to that induced by inactivated HRS (group F). The IgM response lasted longer in the ISCOM™ immunized animals especially in the groups immunized intranasally (groups A, C and group E i.n. plus s.c.). When comparing the IgM responses within the ISCOM™ vaccinated groups, significantly ($P<0.01$) higher responses were recorded in animals from groups immunized intranasally (group A, C and group E i.n. plus s.c.) than those immunized subcutaneously (group B and D) (FIG. 15A).

Serum IgG Response

The serum IgG was measured twice after the first vaccination and second vaccinations. The serum IgG response followed IgM response in a classical manner. The ISCOM vaccinated animals (group A, B, C, D and E) developed significantly ($p<0.01$) higher IgG responses than inactivated HRSV vaccinated mice (group F). I.n. vaccination with the ISCOM™ (group A and C) and combined i.n. and s.c. vaccinations (group E) induced significantly ($p<0.01$) or a 100-fold higher IgG responses than subcutaneously ISCOM™ vaccinated groups (groups B and D) (FIG. 15B).

IgG Subclass Responses

The IgG subclasses response was analyzed on pooled sera in ELISA. Similar profile of the IgG subclass responses were induced by i.n. and s.c. immunizations with ISCOMs™ (group A, B, C, D, E) as measured by ELISA. Higher IgG1 and IgG2a responses were detected in the ISCOM™ immunized mice after i.n., s.c. and the combination of i.n. and s.c. vaccinations than IgG2b and IgG3. There is no difference in IgG subclass responses between i.n. and s.c. immunized mice (FIG. 15C). The ratio IgG2a/IgG1 was higher for iscoms immunized mice than for mice immunized with inactivated whole virus indicating a more prominent $T_H1$ type of response.

Lung sIgA Response

Two weeks after the second vaccination, 2 mice from each group were sacrificed, and lung extracts were prepared as described in Material and Methods. Lung secretory IgA ELISA titers indicated a strong sIgA response was induced by i.n. administration of ISCOMs™ (groups A and C) and group E combining i.n. and s.c. administrations. In contrast, s.c. administrations of ISCOMs™ (groups B and D) and inactivated HRSV (group F) induced no measurable local IgA response in the lung secretion compared to the non-vaccinated control group (group G). The highest sIgA response was 1:13000 detected in mice from group E immunized by a combination of i.n. and s.c. administrations, followed by i.n. administration of ISCOM™ I (1:11000) and i.n. administration of ISCOM™ II (1:6000) (FIG. 15D). Most striking is that the highest IgA response in lung secretion n22 weeks after the immunization was induced by the combined i.n. and s.c. mode of immunization.

The Antibody Response in Various Mucosal Organs

IgA response was measured in upper respiratory tract, lung, genital and in alimentary tract. The extraction of the various secretions were carried out as described in Example 2. The highest IgA antibody response to RSV was obtained in secretion from genital tract which was about 7-fold higher than in secretion from upper respiratory tract and lung. In the gut secretion the lowest IgA antibody titres to RSV was found i.e. a reciproc titre of about 100. The detailed results are shown in FIG. 15E.

Conclusion

After i.n. administration, RSV-iscoms induce unexpectedly high serum antibody titres encompassing IgG2a, a subclass considered attractive for protecting against disease caused by RSV (Murphy, B. R., Hall, S. L. et al., Virus Res. 32, 13–36, 1994). One immunization already induced clearcut serum antibody response implicating commercial feasibility.

The high IgA antibodies in secretion from the lung and upper respiratory tract give prospect for an efficient vaccine inducing a first line of defence in the "port" of infection i.e. the respiratory tract.

These studies also suggest that RSV envelope proteins (F and G) are of great interest to test as mucus targeting molecules also for mucosa in remote organs, particularly for induction of antibody response in the genital tract where the highest IgA antibody response was recorded.

BRIEF DESCRIPTION OF THE DRAWINGS

FIG. 5. The serum antibody response to OVA following various OVA/rCTB formulations. The immunization experiments encompassed the following groups:
1. i.n. 10 μg OVA without Quillaja (QA)
2. i.n. 10 μg OVA-ISCOM™
3. i.n. 10 μg OVA-ISCOM™ and 10 μg rCTB mixed as separate entities
4. i.n. 10 μg of each OVA and rCTB in the same iscom (OVA/rCTB)
5. s.c. 2 μg OVA-ISCOM™ (10 ug QA)
6. i.n. OVA and free rCTB mixed as separate entities. The dose 10 μg of each
7. i.n. 10 μg of free OVA supplemented with matrix (10 μg)
8. i.n. control without antigen

FIG. 6. The immunization experiment encompassed the same groups as listed in FIG. 5.

FIG. 7. The IgG antibody response against OVA is mucous membranes. The same groups as shown in FIG. 5 were included in this immunization experiment.

| Group | Immunizing substance | Mode of administration |
|---|---|---|
| A | OVA-ISCOM ™ | 5 µg antigen intranasally i.n. |
| B | OVA/PR8-ISCOM ™ | 5 µg antigen i.n. |
| C | OVA/PR8-ISCOM ™ | 10 µg antigen i.n. |
| D | PR8-ISCOM ™ | 5 µg antigen i.n. |
| E | OVA/PR8-ISCOM ™ | 5 µg antigen s.c. |

Figure 1A:
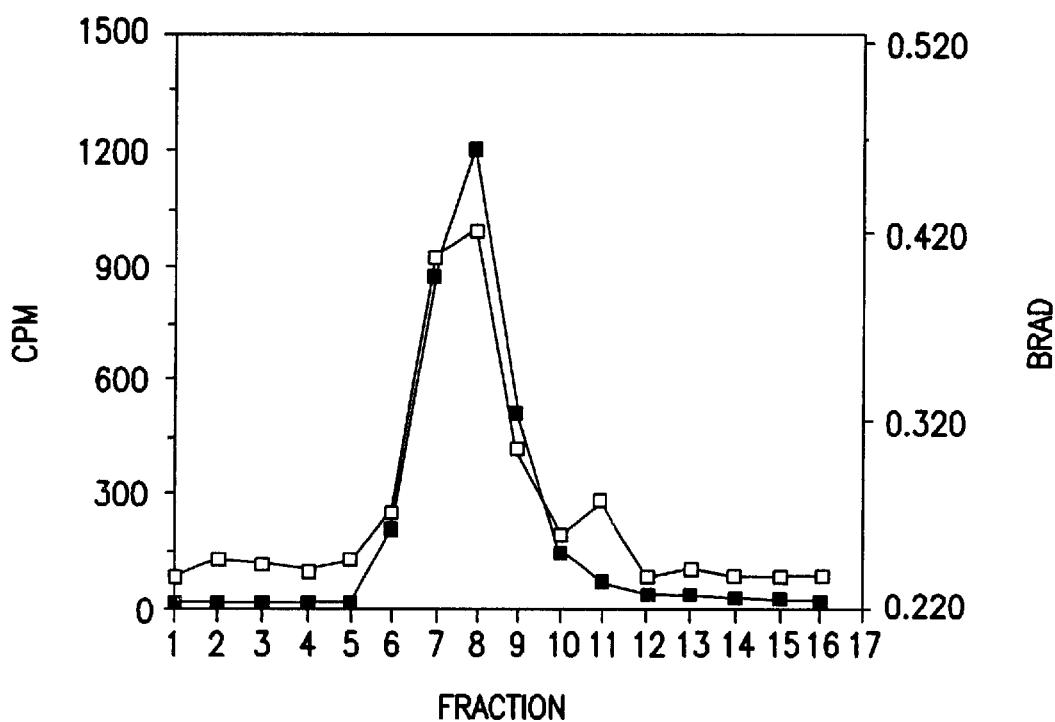
FIG. 1A shows how iscoms sediment with incorporated rCTB in a 10–50% sucrose gradient after an ultracentrifution. The CPM values mark the radioactivity of $^3$H-cholesterol (■) follow the 8iscoms. The protein value (CTB) (□) is measured according to Bradford. ISCOMs™ and rCTB are recovered in fraction 6–9. Thus, most of the CTB are recovered in ISCOM™ fractions.
Figure 1B:
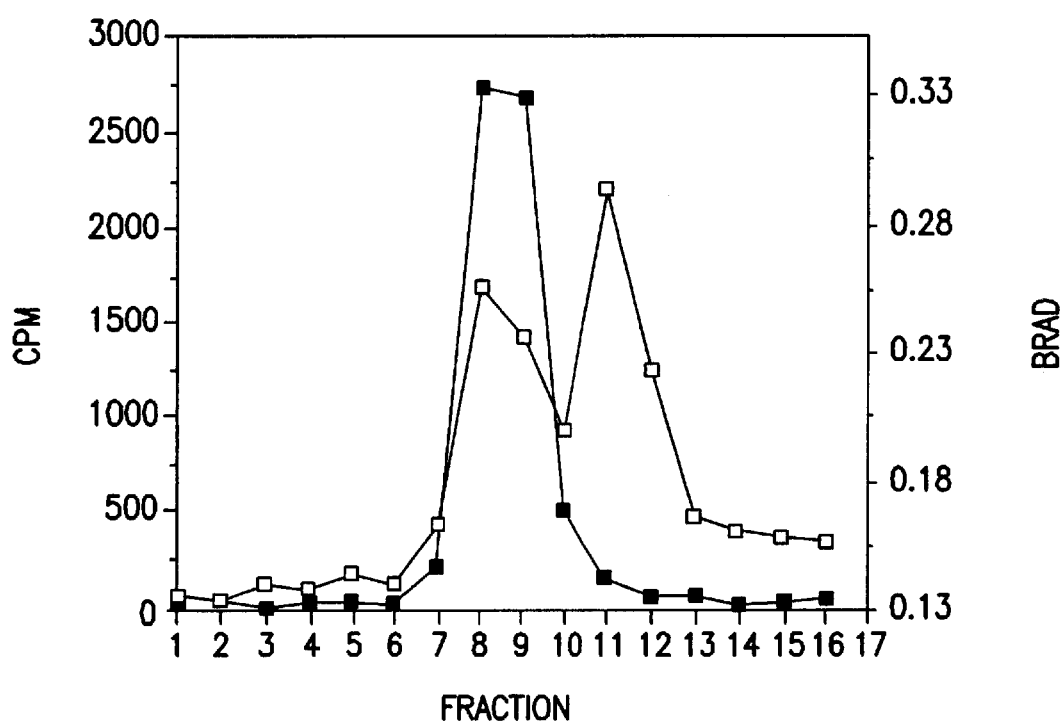
FIG. 1B shows the type of diagram as in FIG. 1A. In this experiment the rCTB concentration was a 100-fold larger than the GM1-concentration. Not-incorporated rCTB is found high up in the gradient i.e. in fraction 10–12.
Figure 2A:
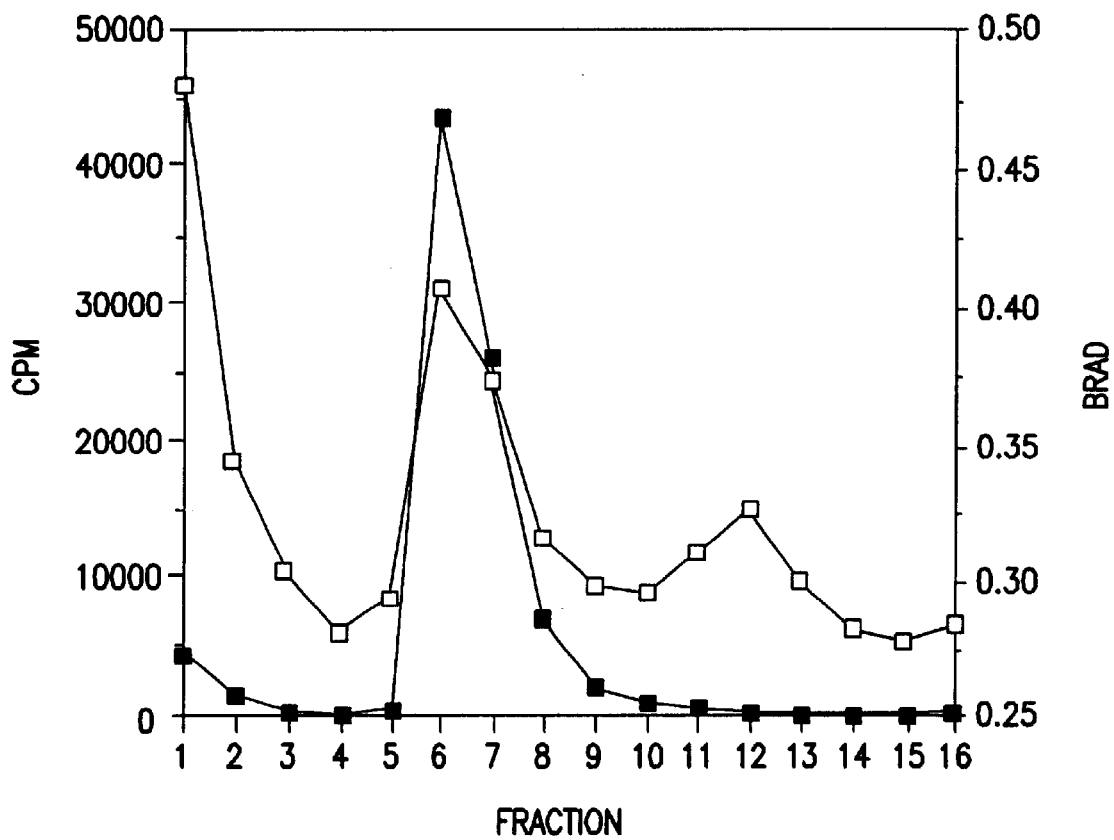
FIG. 2 characterizes the iscoms by ultracentrifugation:
a) ovalbumin (OVA)
b) PR8-ISCOMs™
c) PR8/OVA-ISCOMs™
Figure 2B:
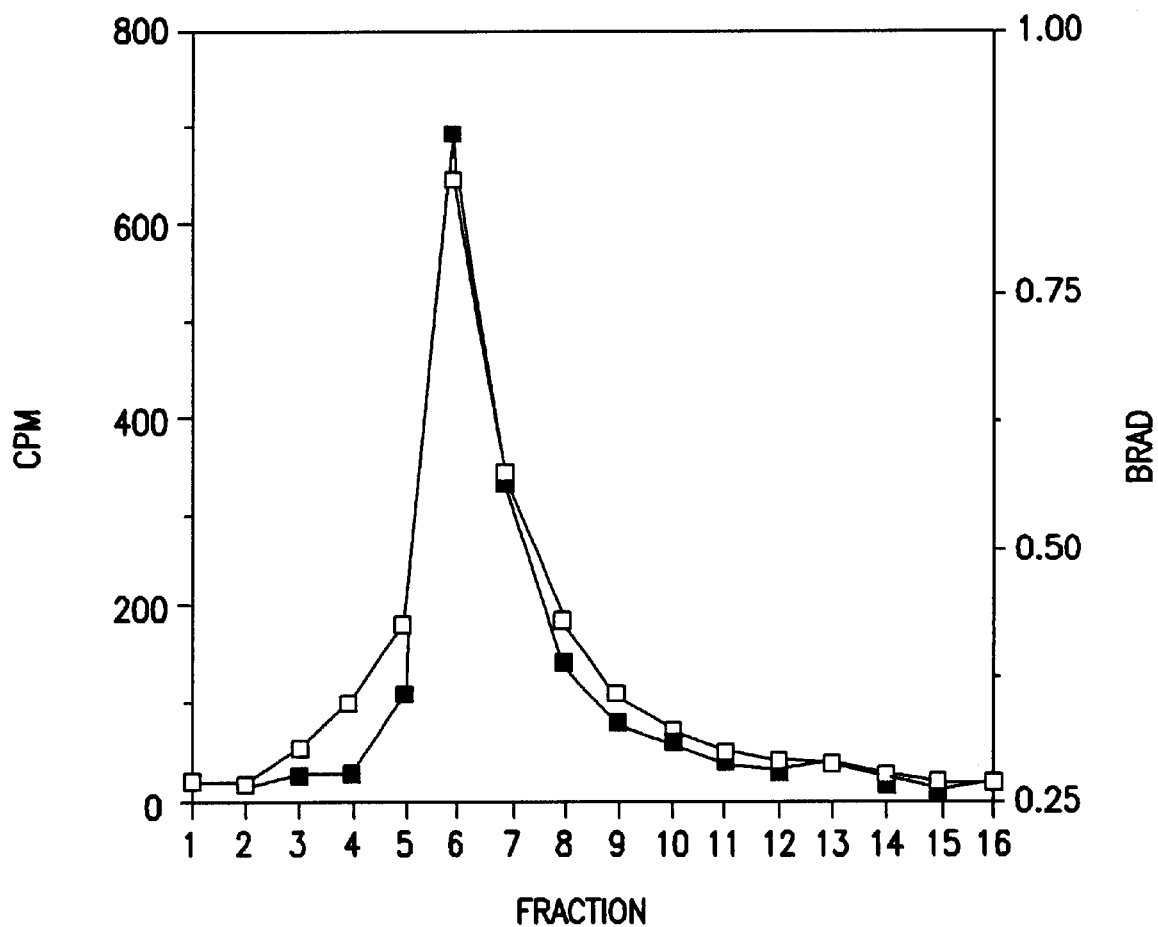
Figure 2C:
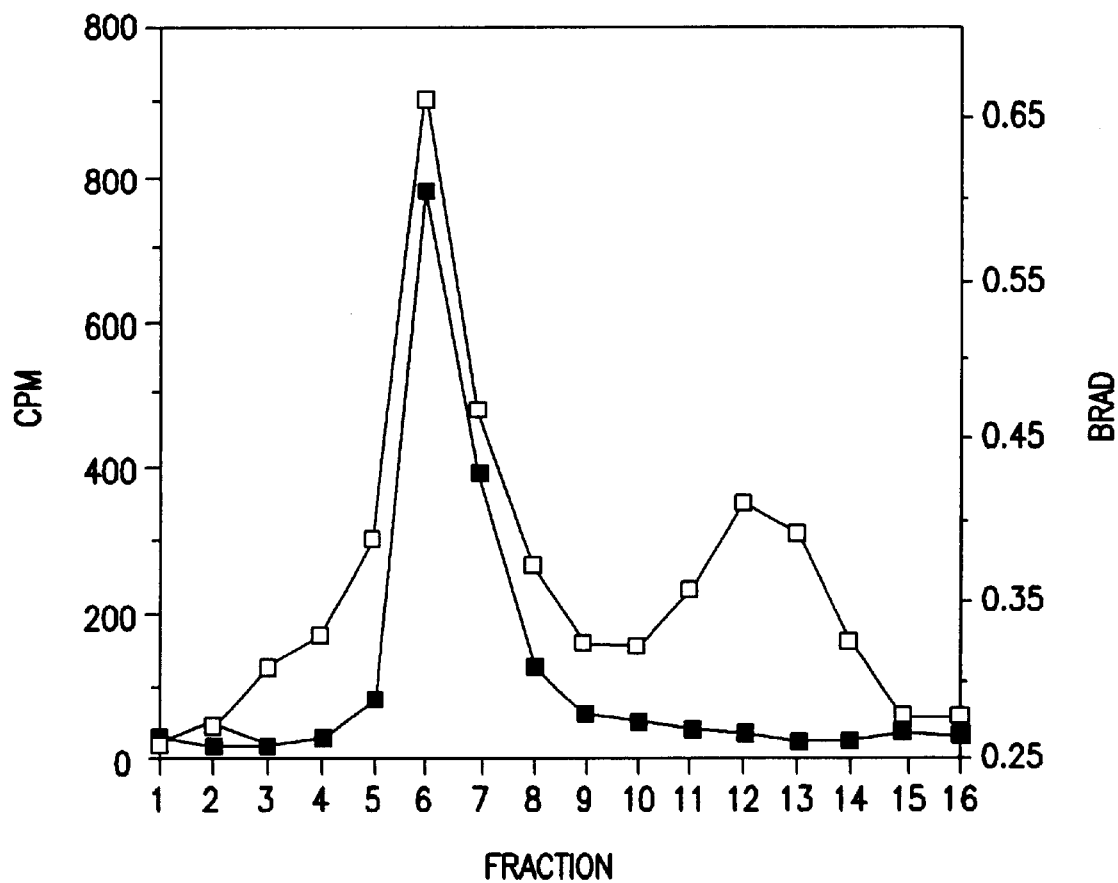
Figure 3A:
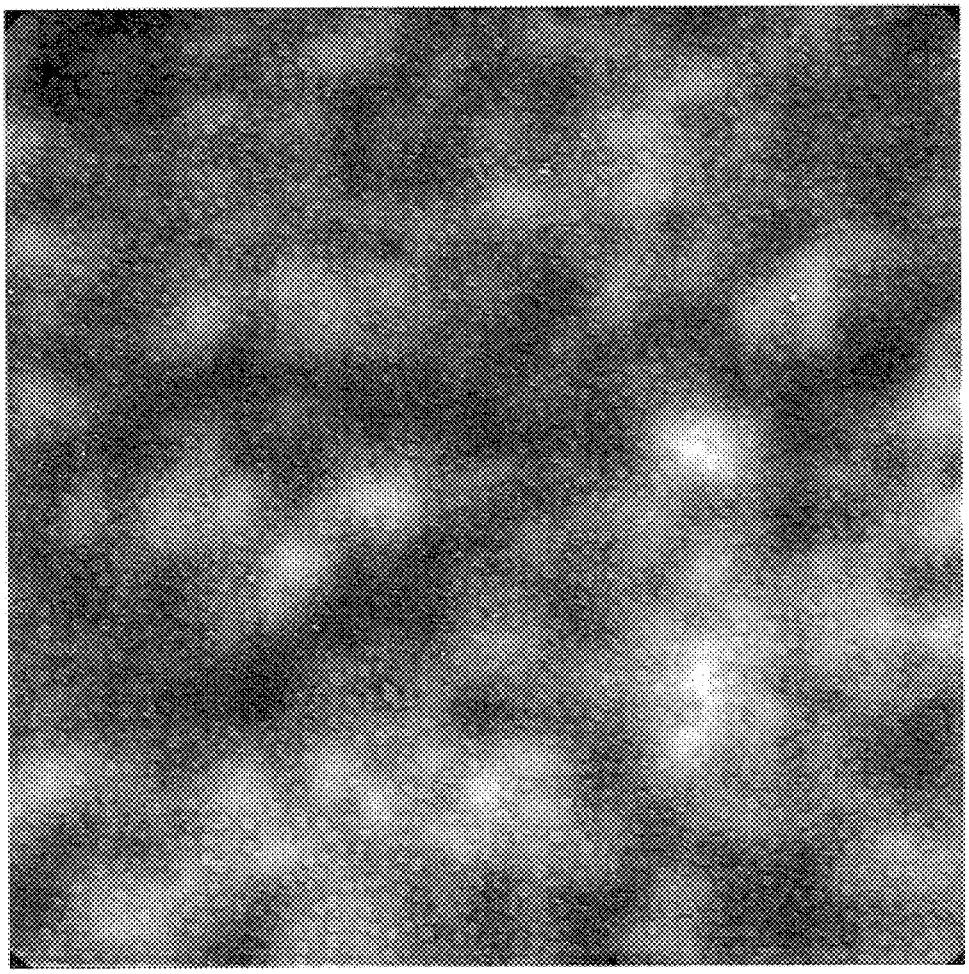
FIG. 3 Electron microscopy of
a. OVA-ISCOMs™
b. PR8-ISCOMs™
c. PR8/OVA-ISCOMs™
Figure 3B:
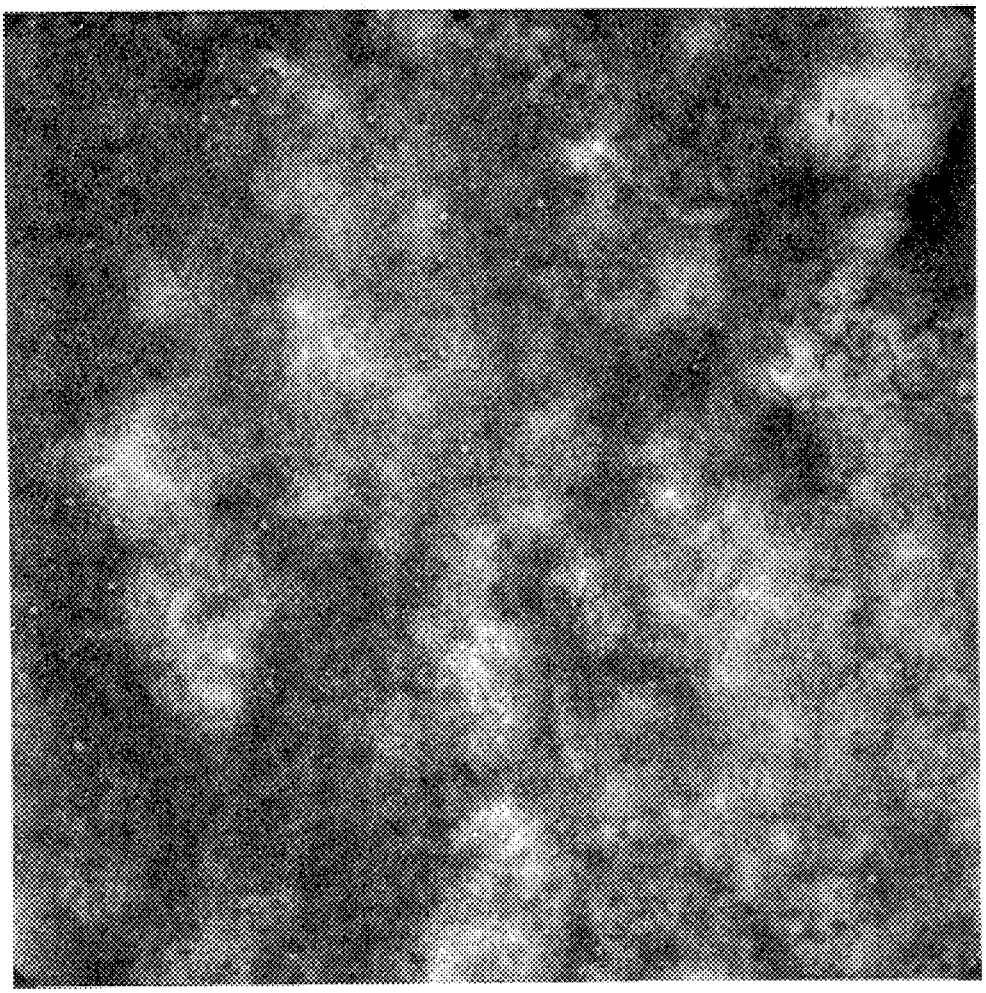
Figure 3C:
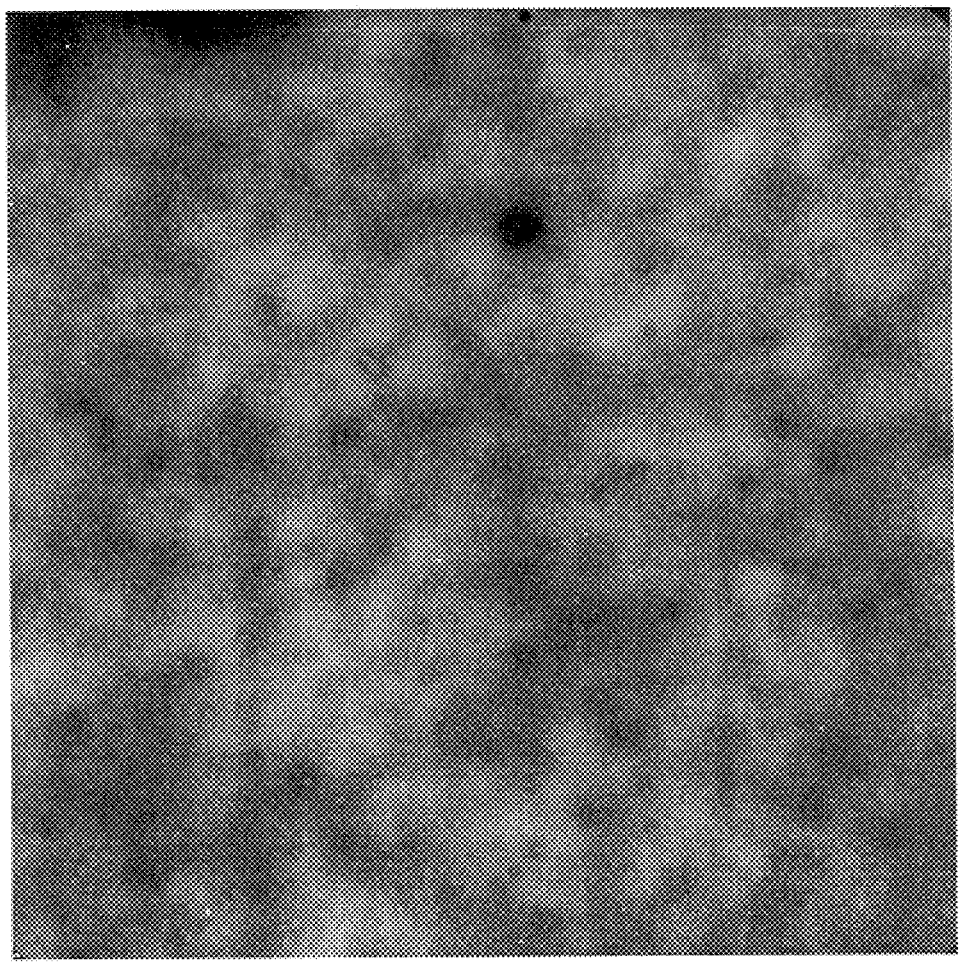
Figure 4A:
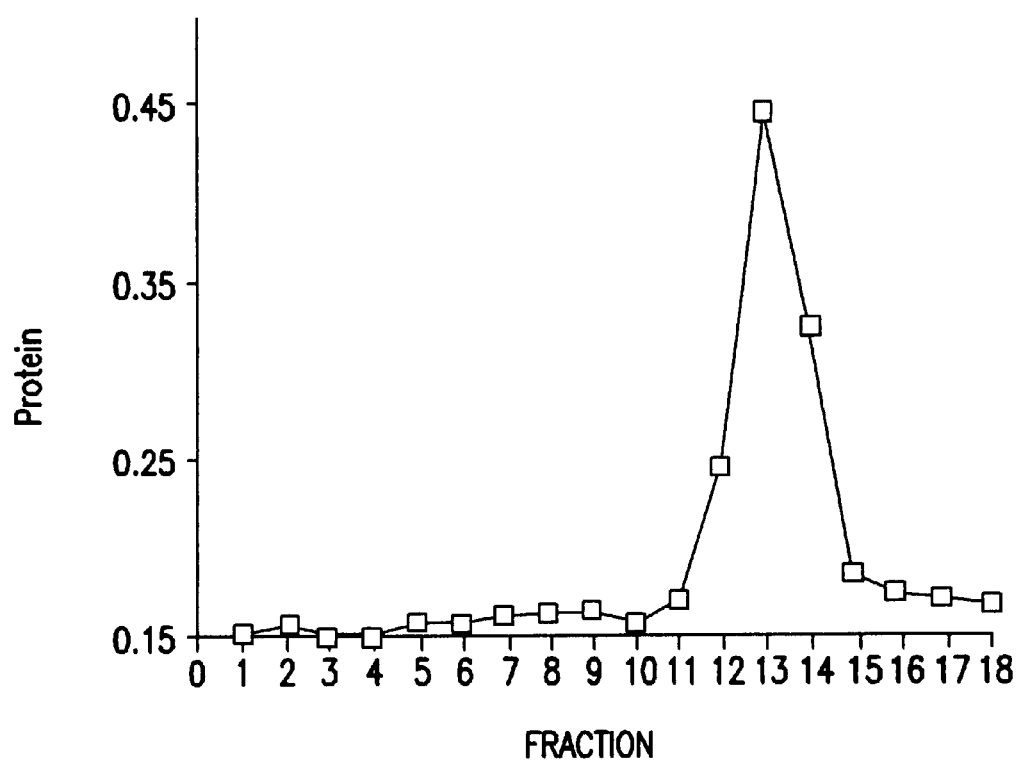
FIG. 4A shows sedimentation of free rCTB (□) measured by protein determination in a 10–50% sucrose gradient centrifugation, i.e. rCTB not incorporated into ISCOM™ sediments slowly and is recovered high up in the gradient i.e. fractions 12 to 14.
Figure 4B:
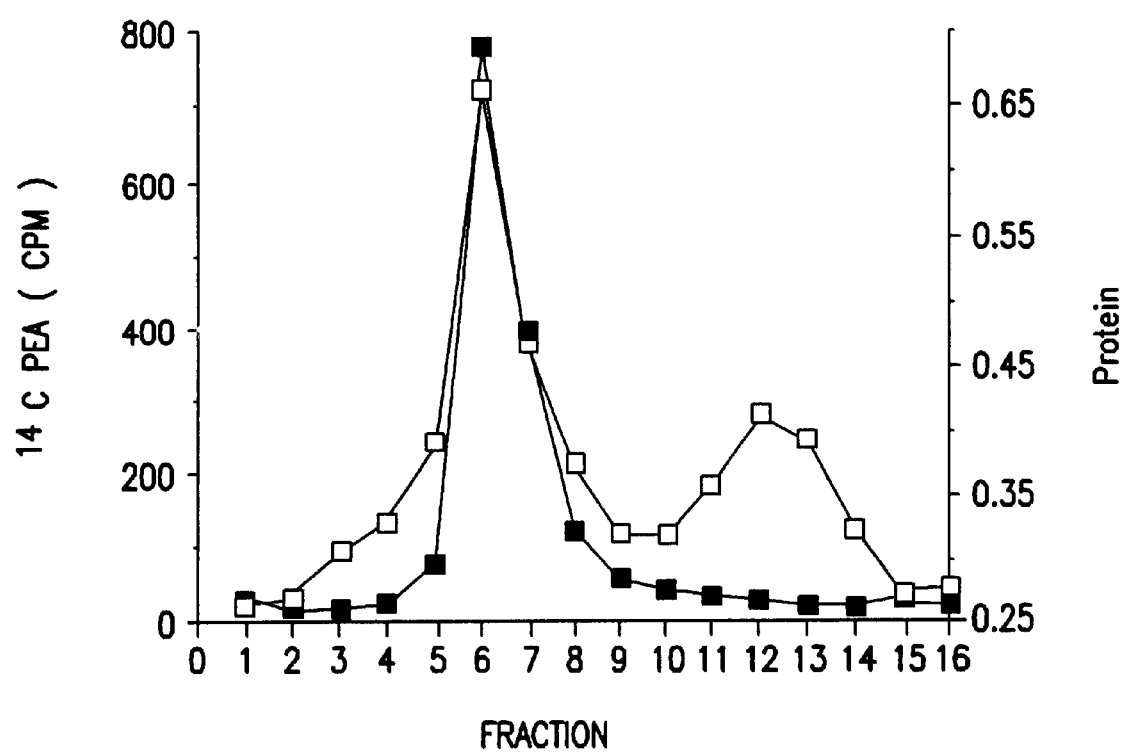
FIG. 4B shows $^{14}$C phosphatidylethanolamine ($^{14}$C PEA) radioactivity (CPM) (■) following the ISCOM™ in the sucrose gradient at the ultracentrifugation. Lipidated protein-OVA are recovered measured by Bradford (Ref. see text) (□) with iscoms with recovered in fractions 6–8. Some note integrated protein is recovered in fractions 11, 12 and 13.
Figure 4C:
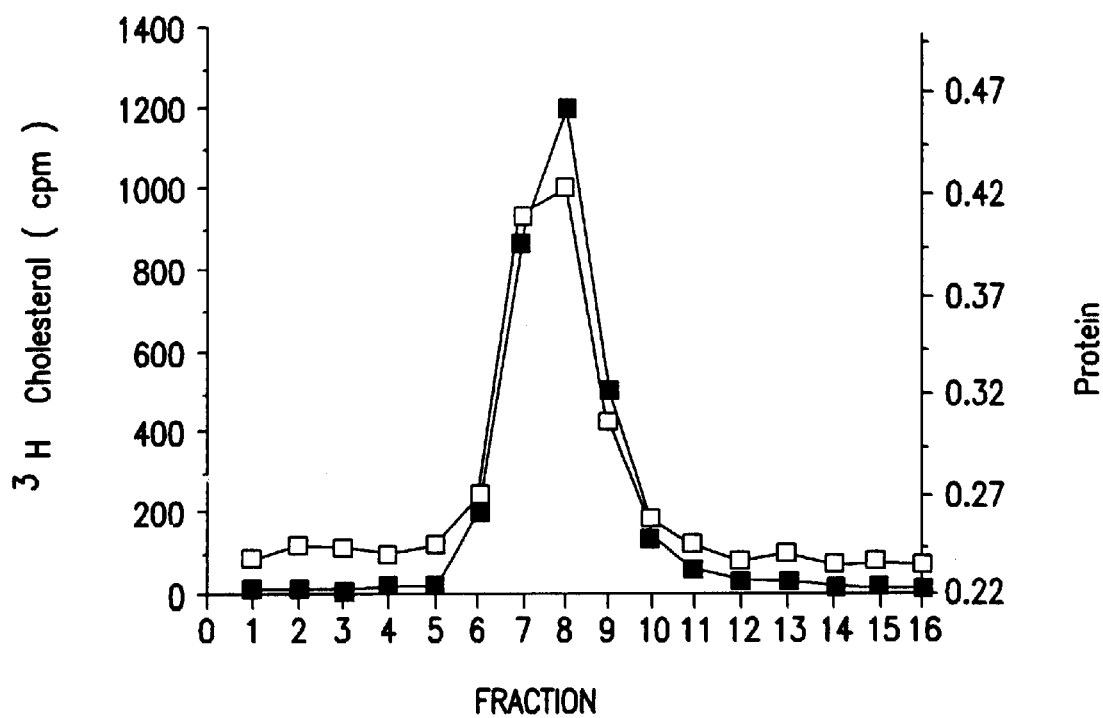
FIG. 4C shows incorporation of rCTB in ISCOMs™ containing GM1. Incorporation of rCTB in ISCOM™ was measured by protein determination (□). Sedimentation of ISCOMs™ is shown by radioactivity $^3$H labelled cholesterol (CPM) (■) following the ISCOM™ in the gradient. Both protein i.e. rCTB and $^3$H cholesterol follow ISCOM™ structures, the latter verified by EM, are recovered in fractions 6 through 9.
Figure 4D:
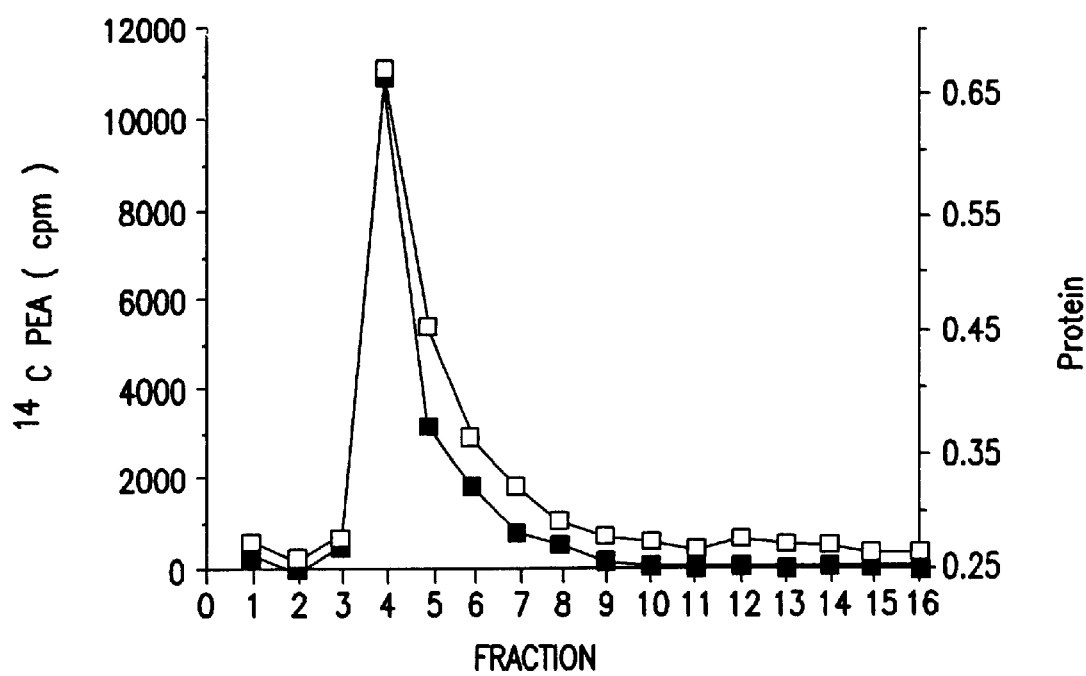
FIG. 4D shows incorporation of lipidated OVA and rCTB determined by protein determination by Bradford (□). Sedimentation of ISCOMs™ is shown by radiolabelled $^{14}$C PEA (■) recovered in fractions 4 through 6, where besides radioactivity also iscom structures were demonstrated by EM.
Figure 4E:
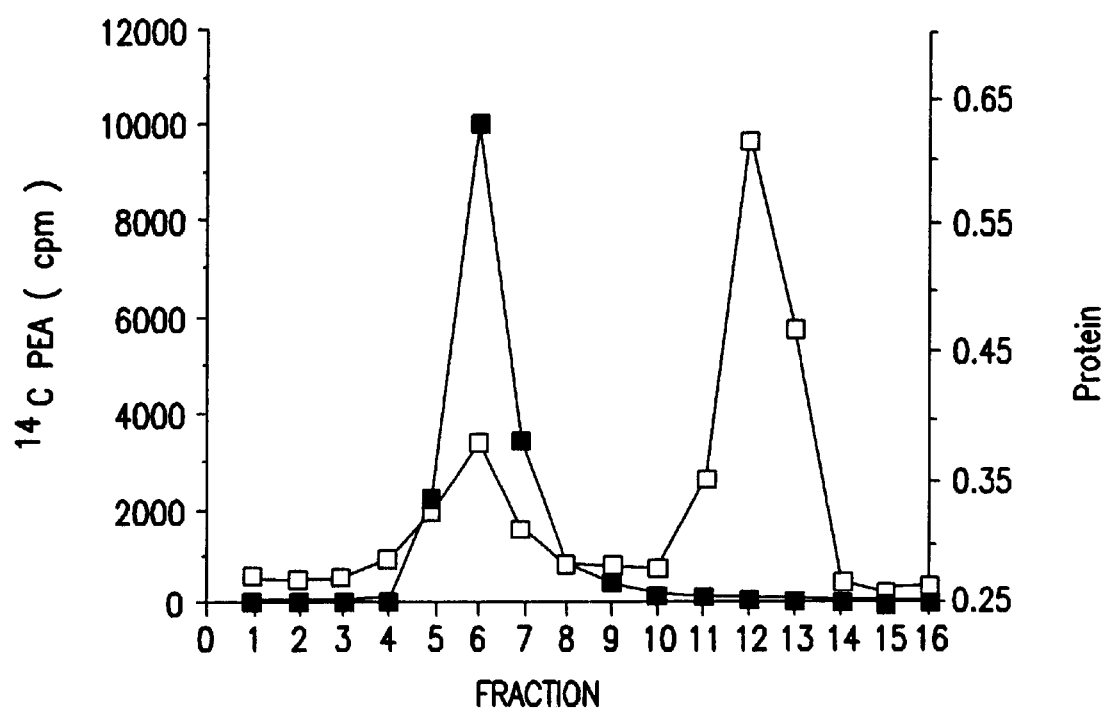
FIG. 4E shows that rCTB added to OVA-ISCOM™, not containing GM1-lipid, are not incorporated into ISCOM™, demonstrated by recovery of the protein i.e. CTB in the top fractions of the gradient i.e. 11 through 13. The lipidated OVA is found in fractions 5 through 8.
Figure 5A:
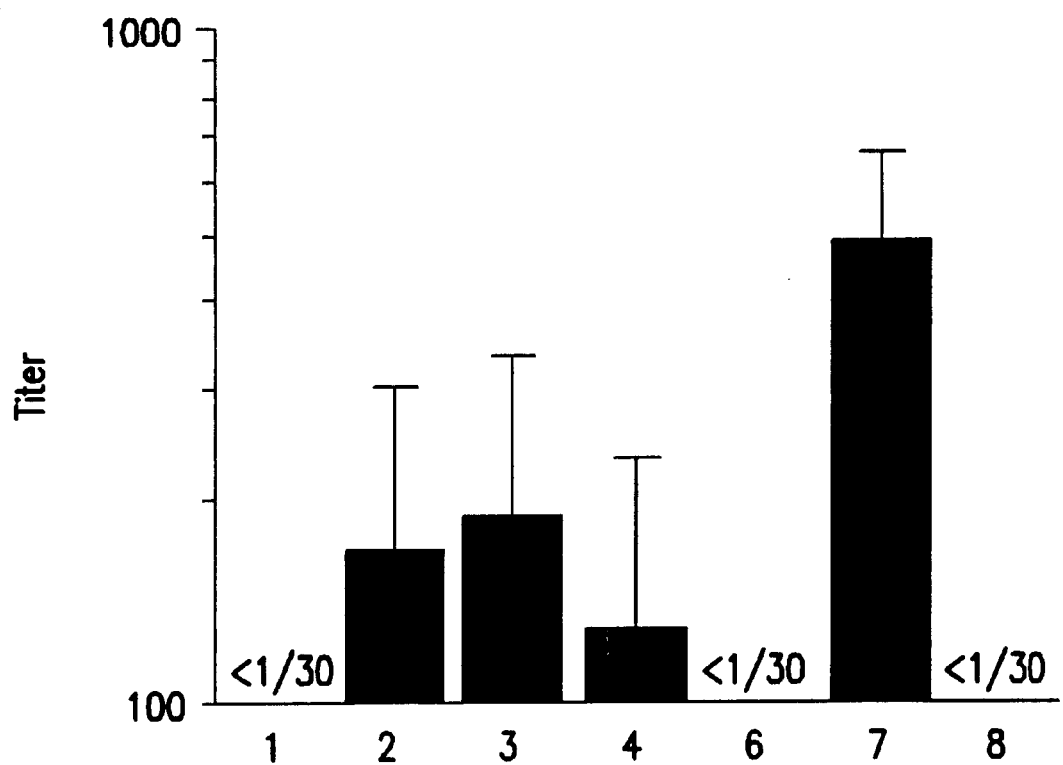
FIG. 5A shows the serum antibody response against OVA analyzed in ELISA (two weeks) after the first intranasal (i.n.) immunization of mice. No antibody response could be measured to OVA without adjuvant or to OVA, which was adjuvanted to rCTB (6).
Figure 5B:
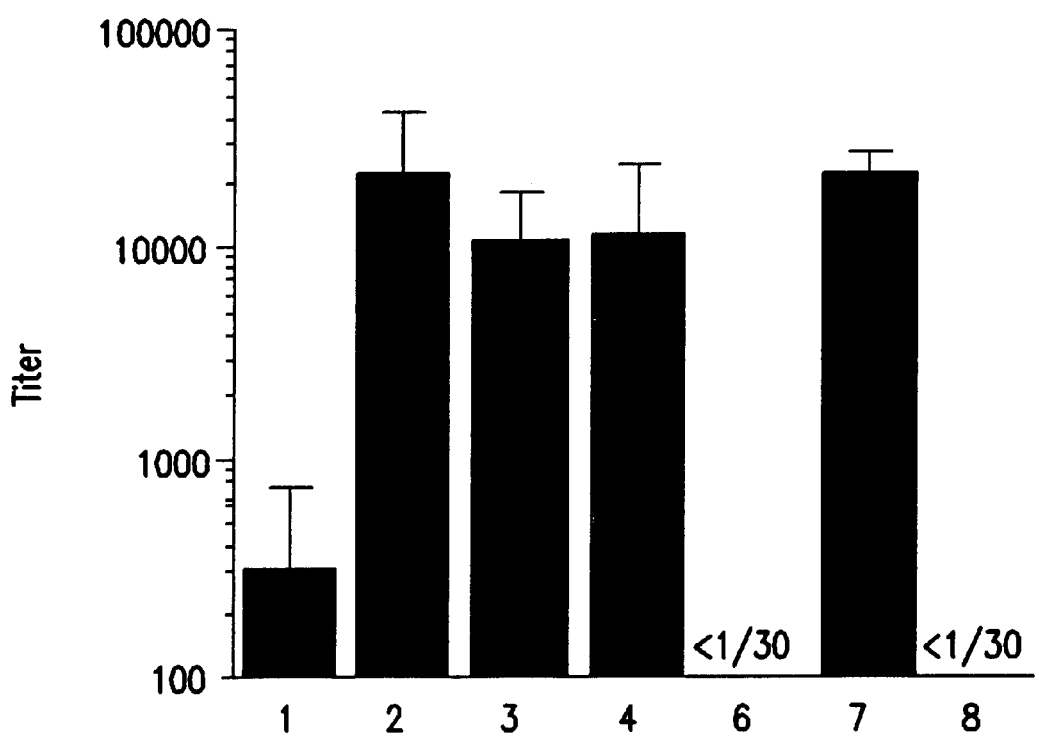
FIG. 5B shows that two weeks after the 2nd immunization all mice which had been immunized with ISCOM™ or matrix formulations responded with high serum antibody titres to OVA. Mice that had been immunized with OVA supplemented with rCTB in separate entities showed lower serum antibody titres than mice immunized with OVA alone.
Figure 5C:
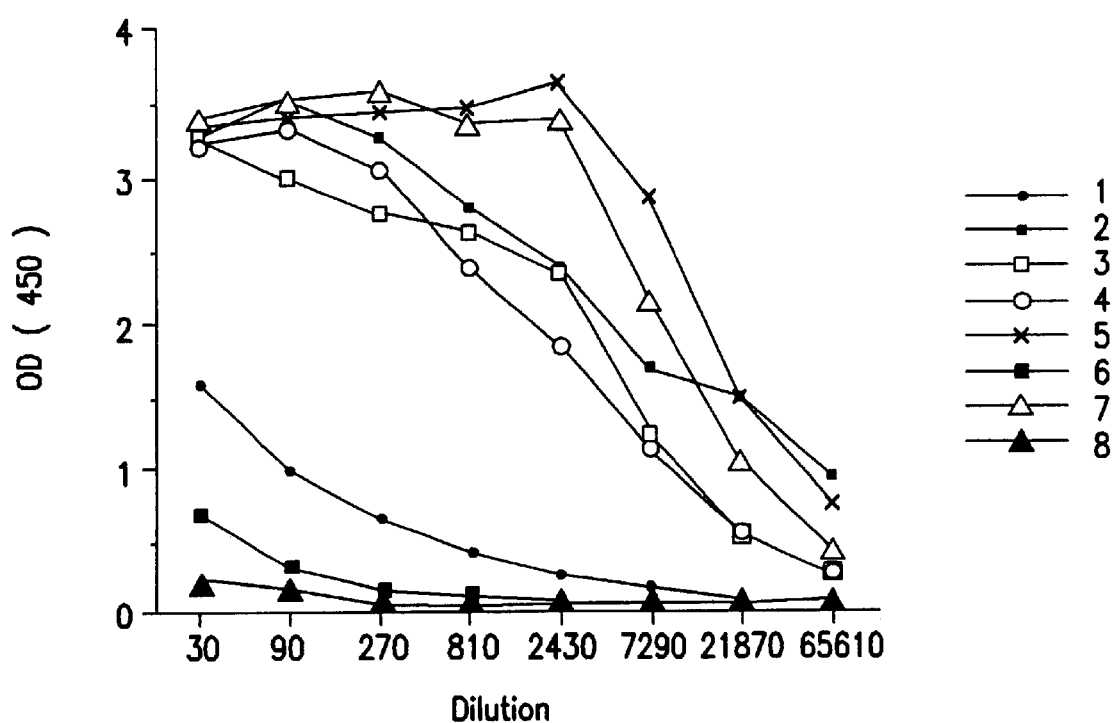
FIG. 5C shows the ELISA reading values in increasing dilutions of sera from mice after two immunizations. As shown in this figure, as well as in FIG. 5B, the ISCOM™ formulations with OVA abrogates the tolerance which rCTB evoked with respect to serum antibody response to OVA as "passenger antigen" (PA) or administered with matrix.
Figure 6A:
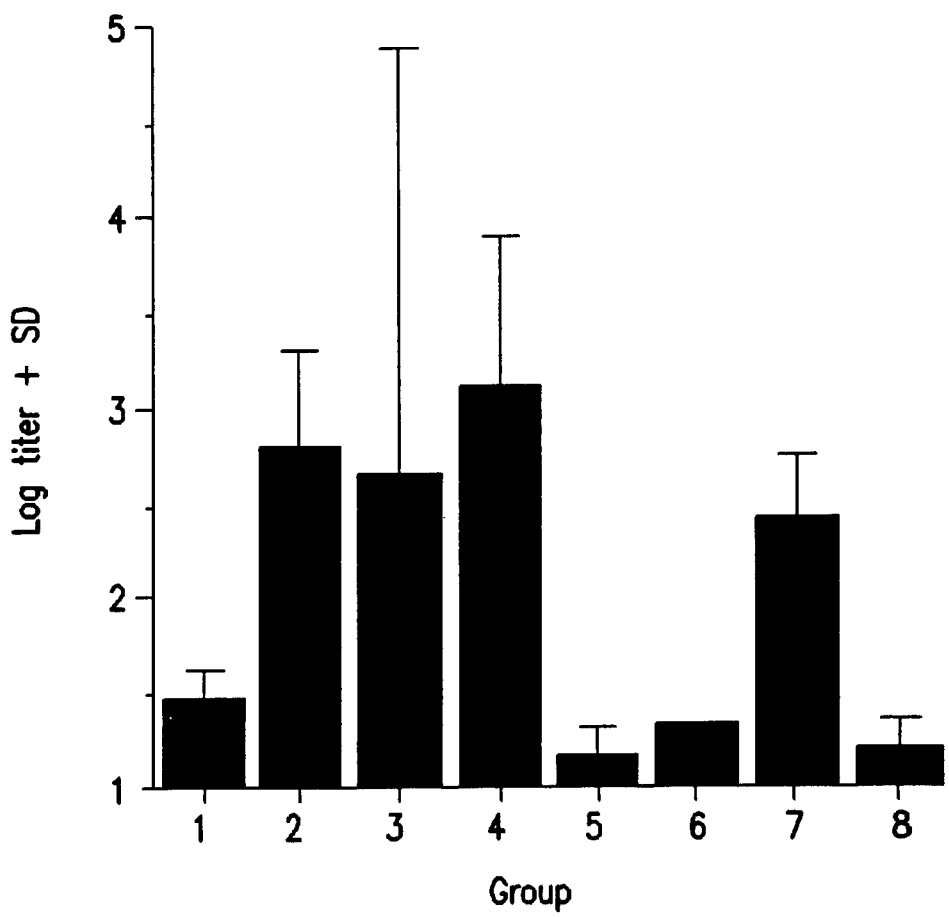
FIG. 6A shows analysis of IgA antibody response to OVA in lung secretion after two (i.n.) immunizations of mice.
Figure 6B:
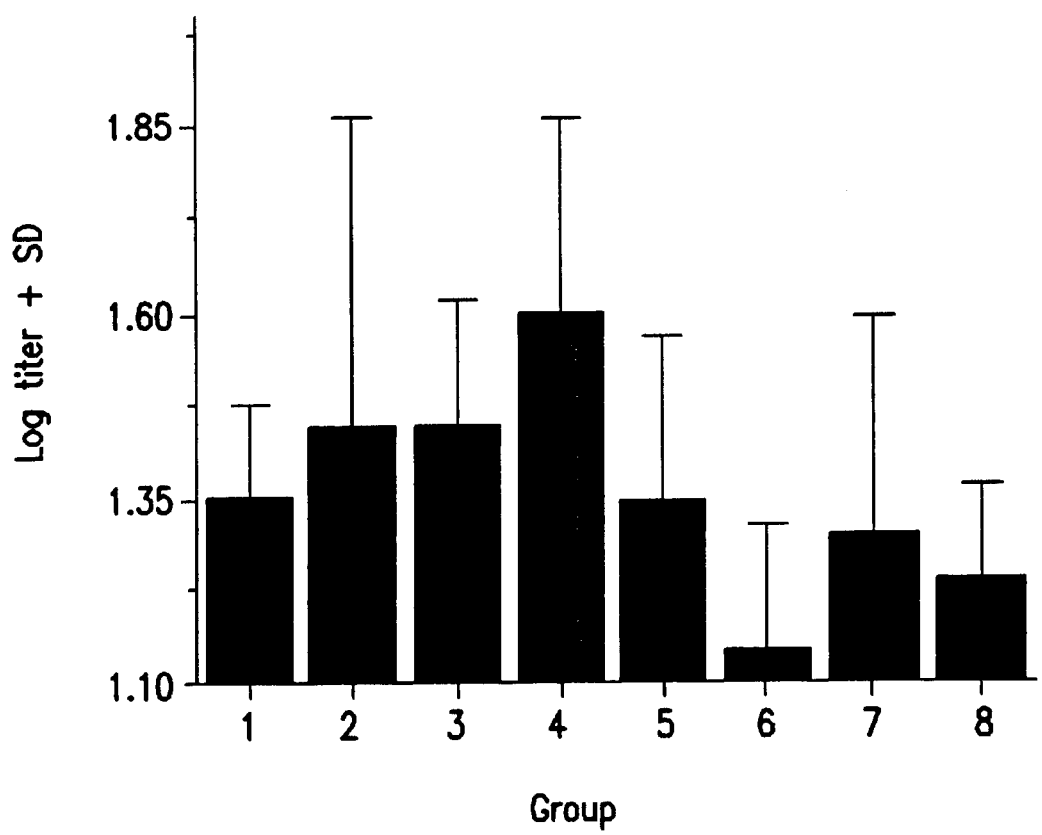
FIG. 6B shows a comparison between the different groups with respect to IgA antibody responses to OVA in the upper respiratory tract secretion. The OVA ISCOM™ and OVA supplemented with matrix evoked after i.n. immunization significantly higher IgA-titres than the OVA-rCTB formulations without adjuvants.
Figure 6C:
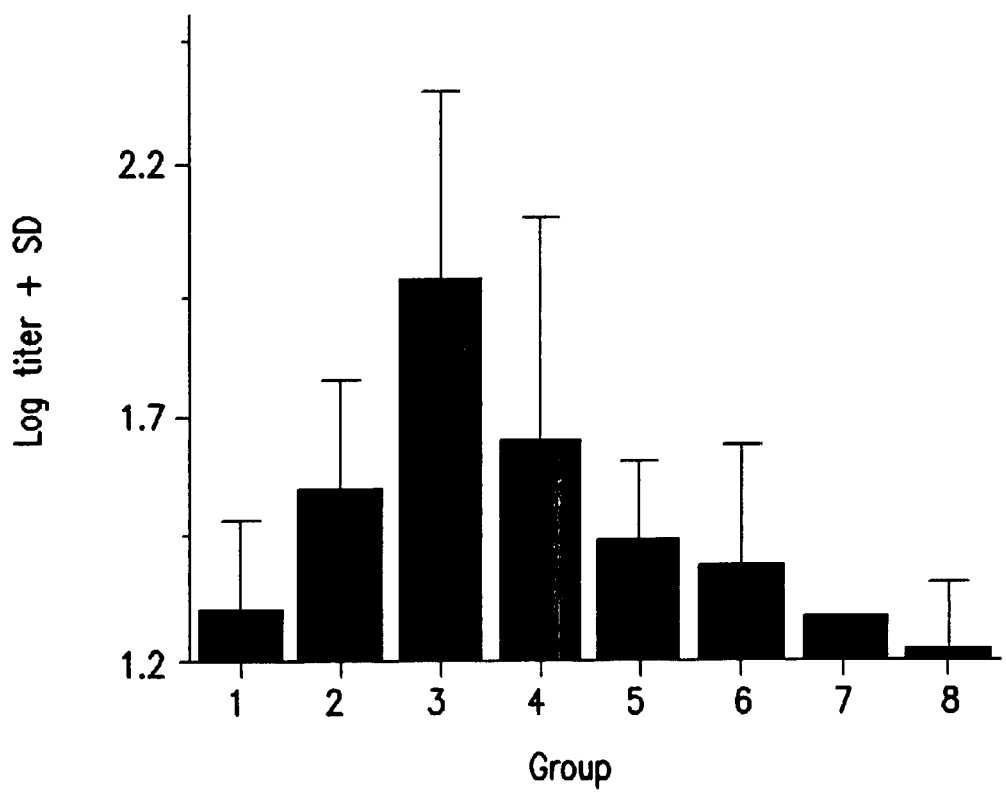
FIG. 6C shows a comparison between IgA antibody responses to OVA induced in the secretion from the genital tract of mice in the different immunization groups.
Figure 7A:
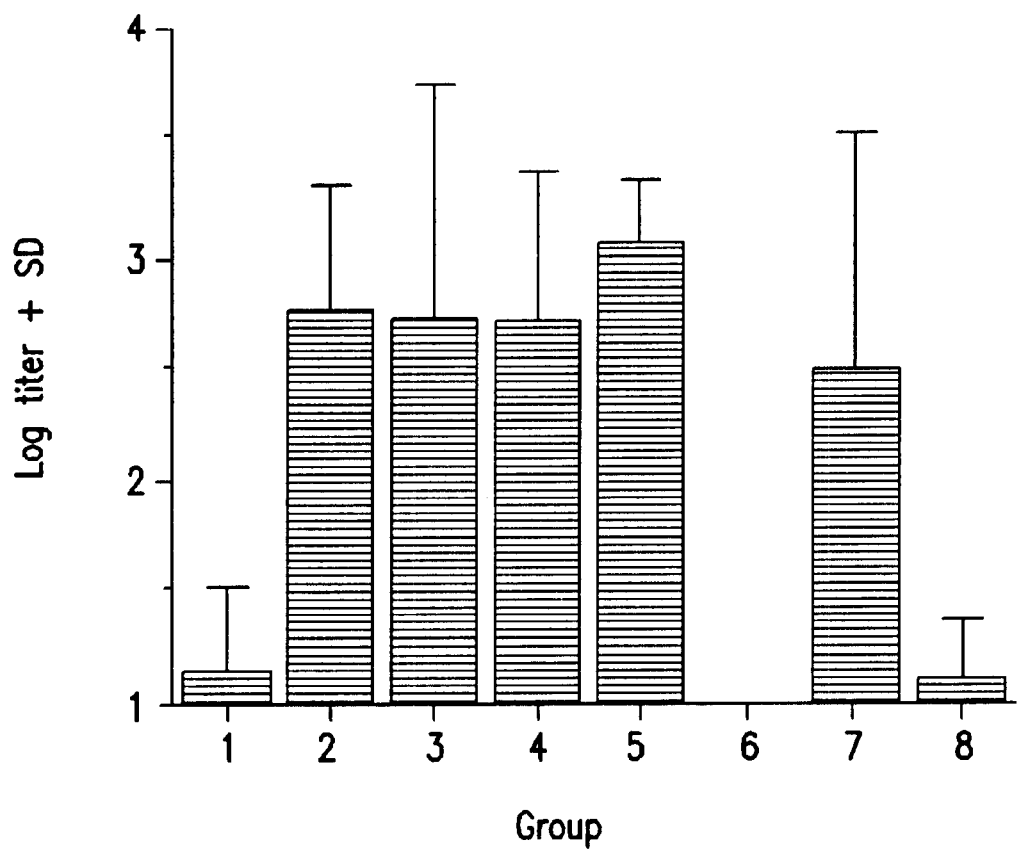
FIG. 7A shows a comparison between IgG antibody responses which were induced in lung secretion of mice in the different immunization groups.
Figure 7B:
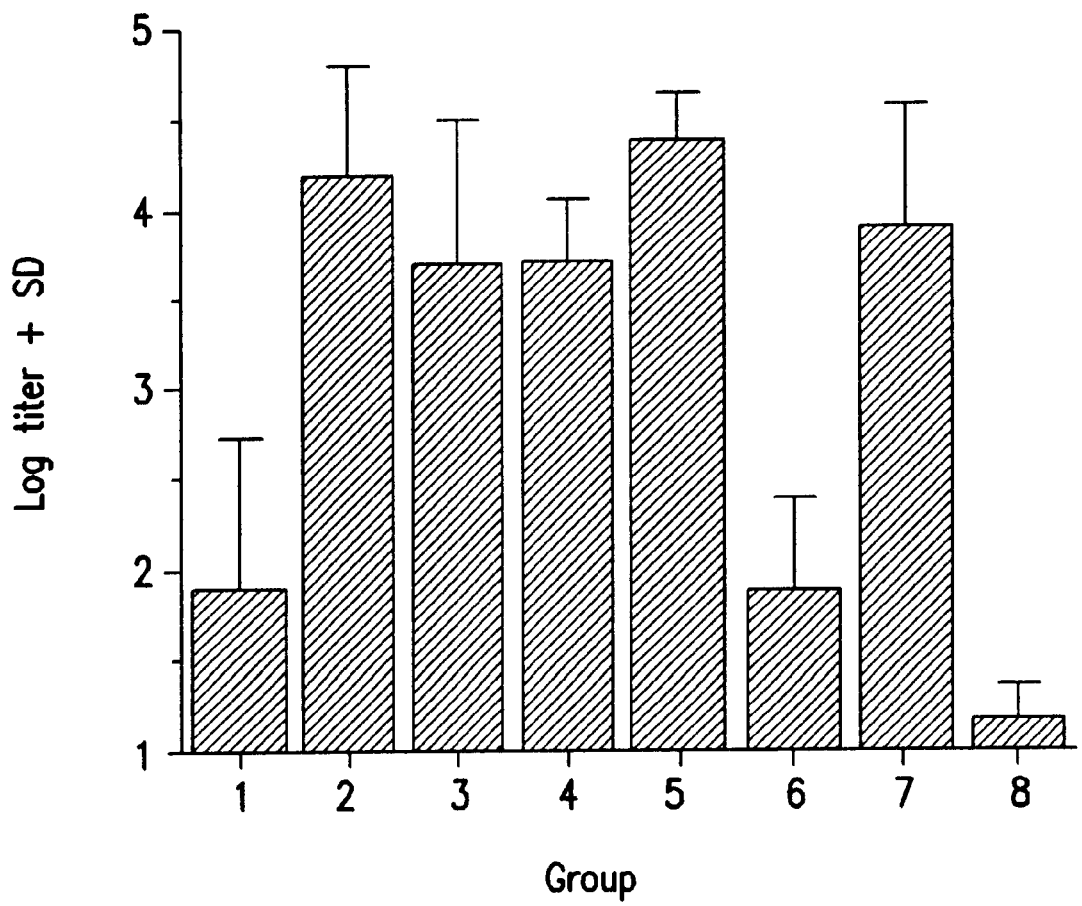
FIGS. 7B, 7C and 7D compare the corresponding IgG antibody responses in the secretions from upper respiratory tract, genital tract and the alimentary tract respectively.
Figure 7C:
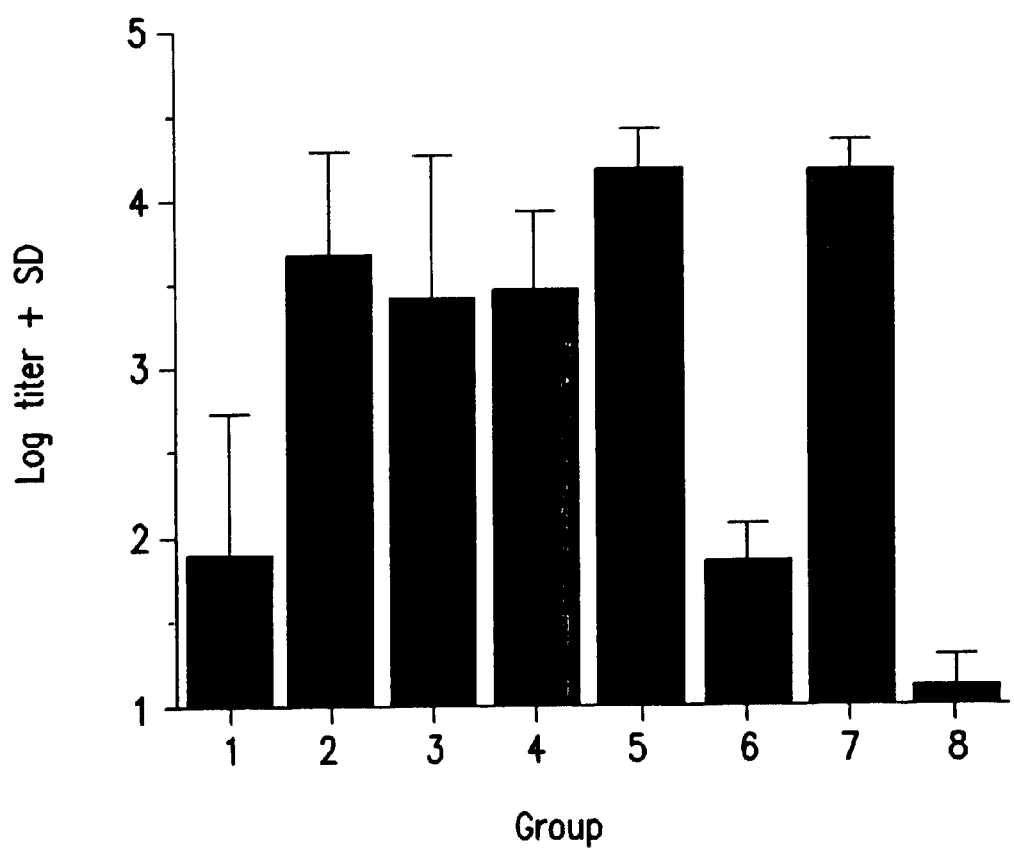
Figure 7D:
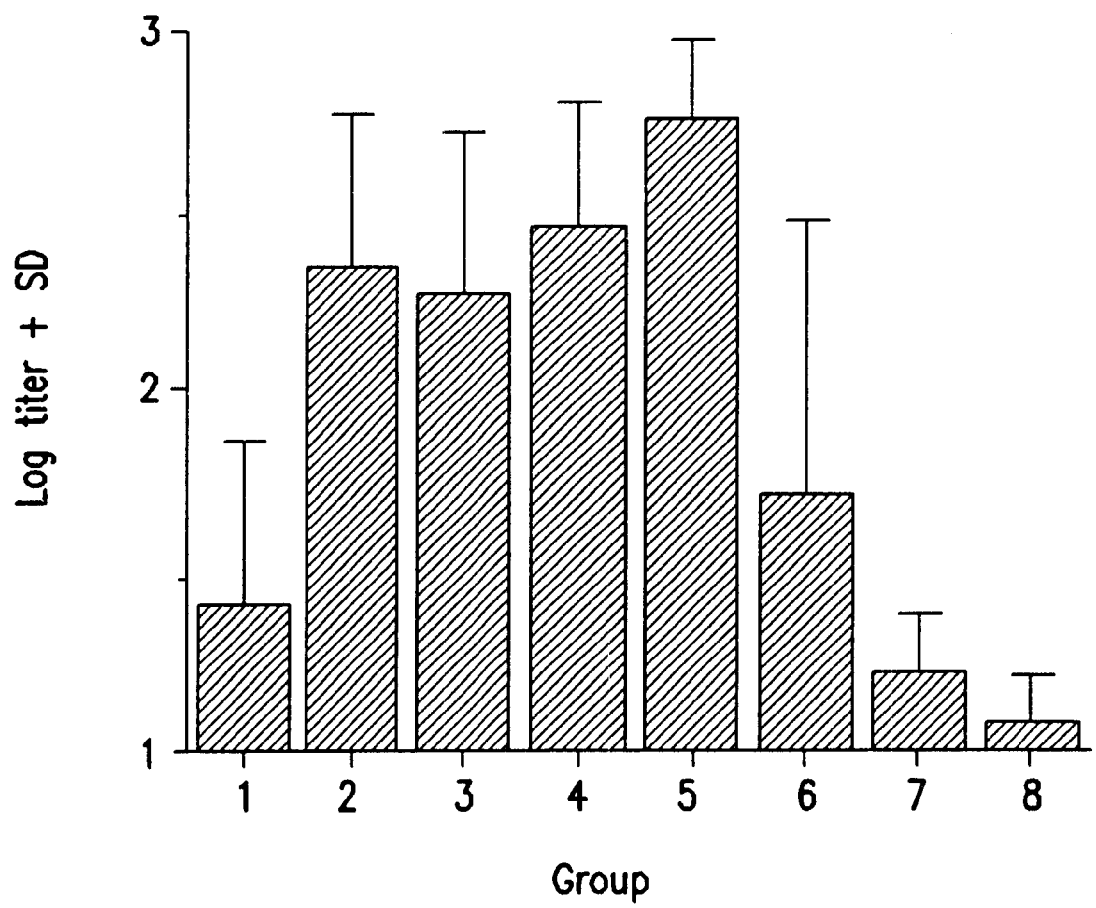
Figure 8A:
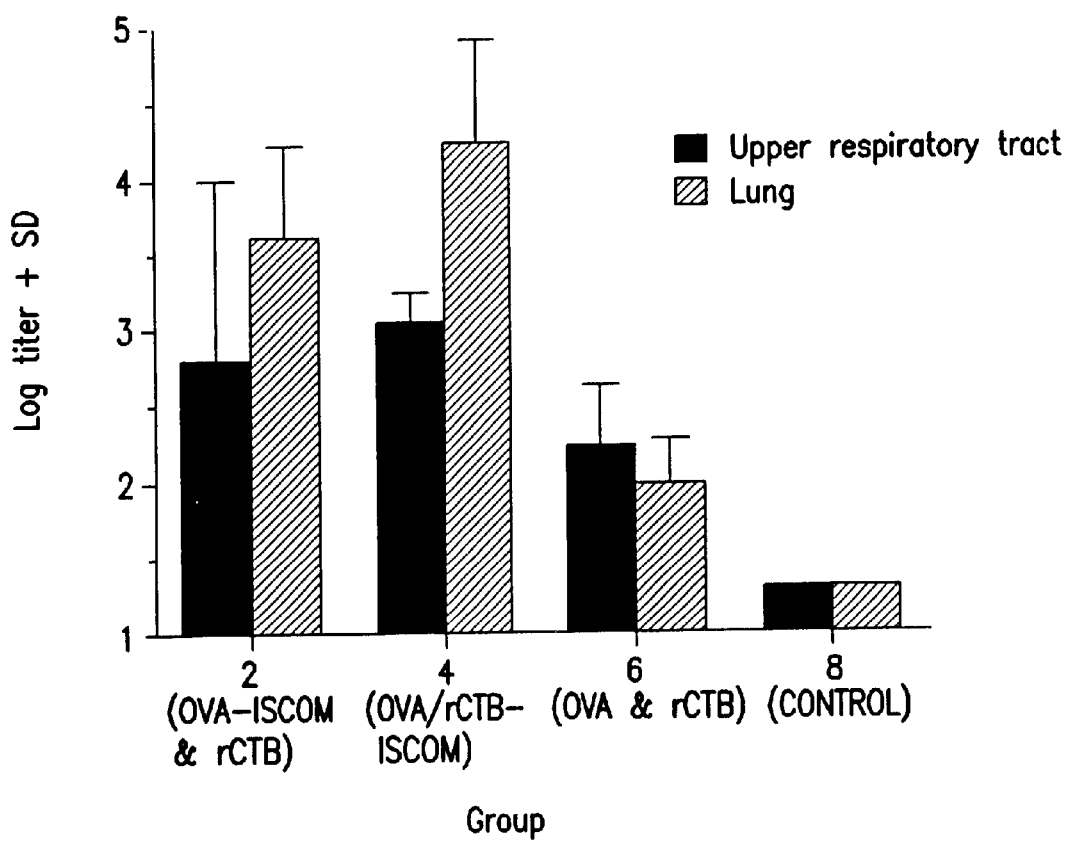
FIGS. 8A and B. Generally, OVA-rCTB in ISCOMs™ or free rCTB supplemented with OVA-ISCOMs™, which in this case served as adjuvant in the form of ISCOM™ matrix for rCTB, induced considerably higher IgA antibody responses to CTB than rCTB without added adjuvant in all tested secretions, i.e. from lung, upper respiratory tract, alimentary tract and genital tract.
Figure 8B:
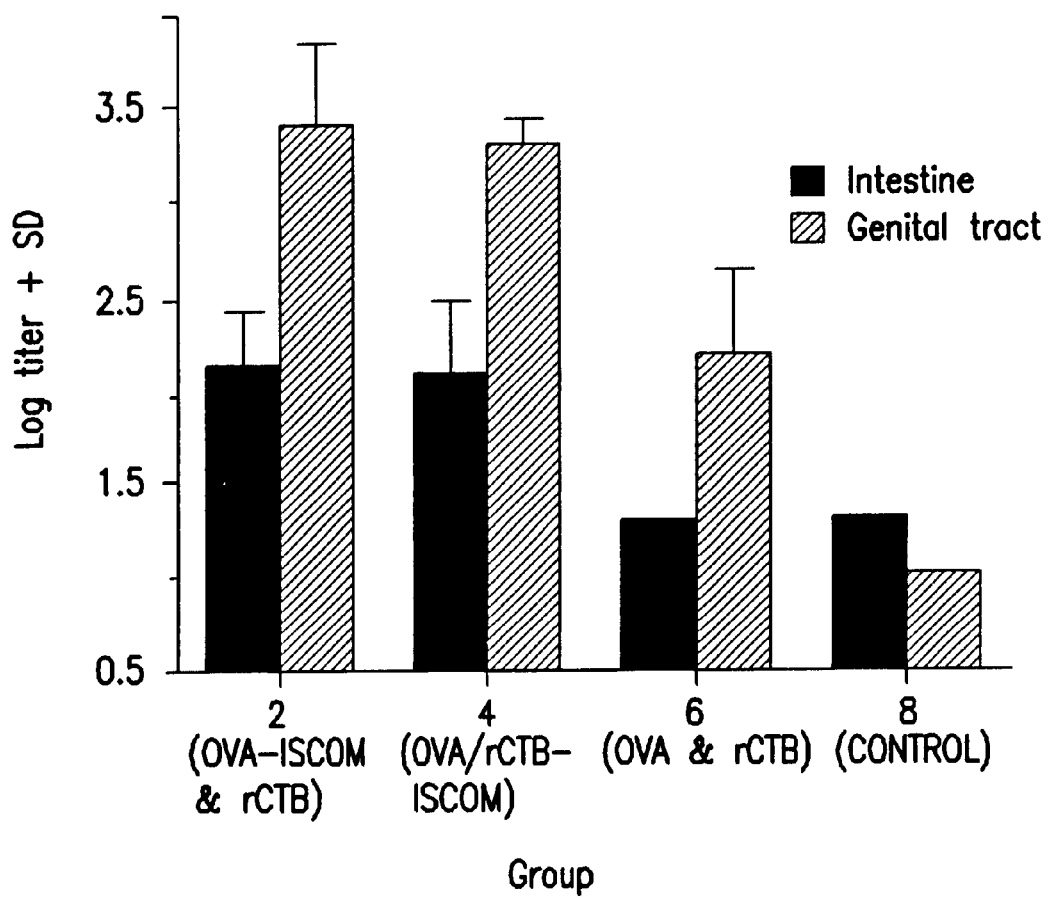
FIG. 8. In the immunization experiments the same groups took part as shown in FIG. 5.
FIGS. 8C and D. High IgG antibody responses were obtained to rCTB in secretions from lungs, upper respiratory tract, genital tract and alimentary tract, with rCTB formulations in ISCOMs™ or in ISCOM™-matrix. The IgG antibody response in these secretions for mice immunized with rCTb without ISCOM™ or ISCOM™-matrix formulations were lower than for rCTB-ISCOM™ and ISCOM™-matrix formulations but significantly higher than for non-immunized controls.
Figure 8C:
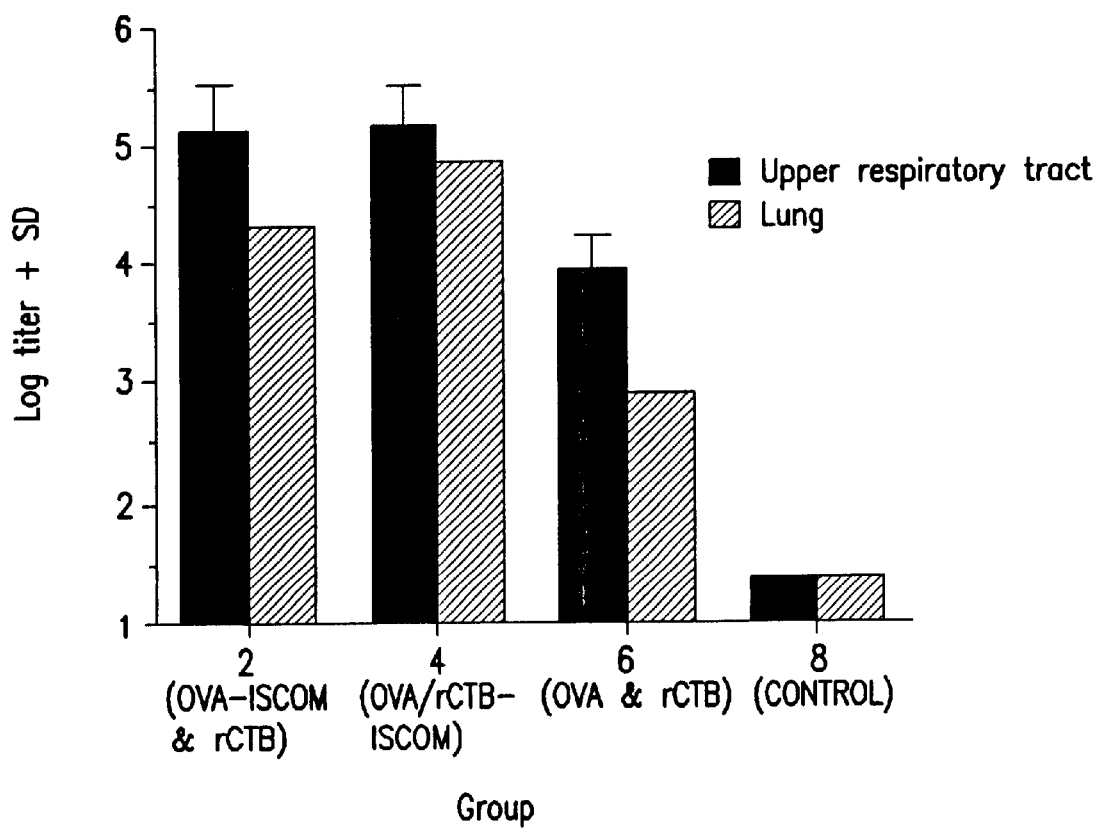
Figure 8D:
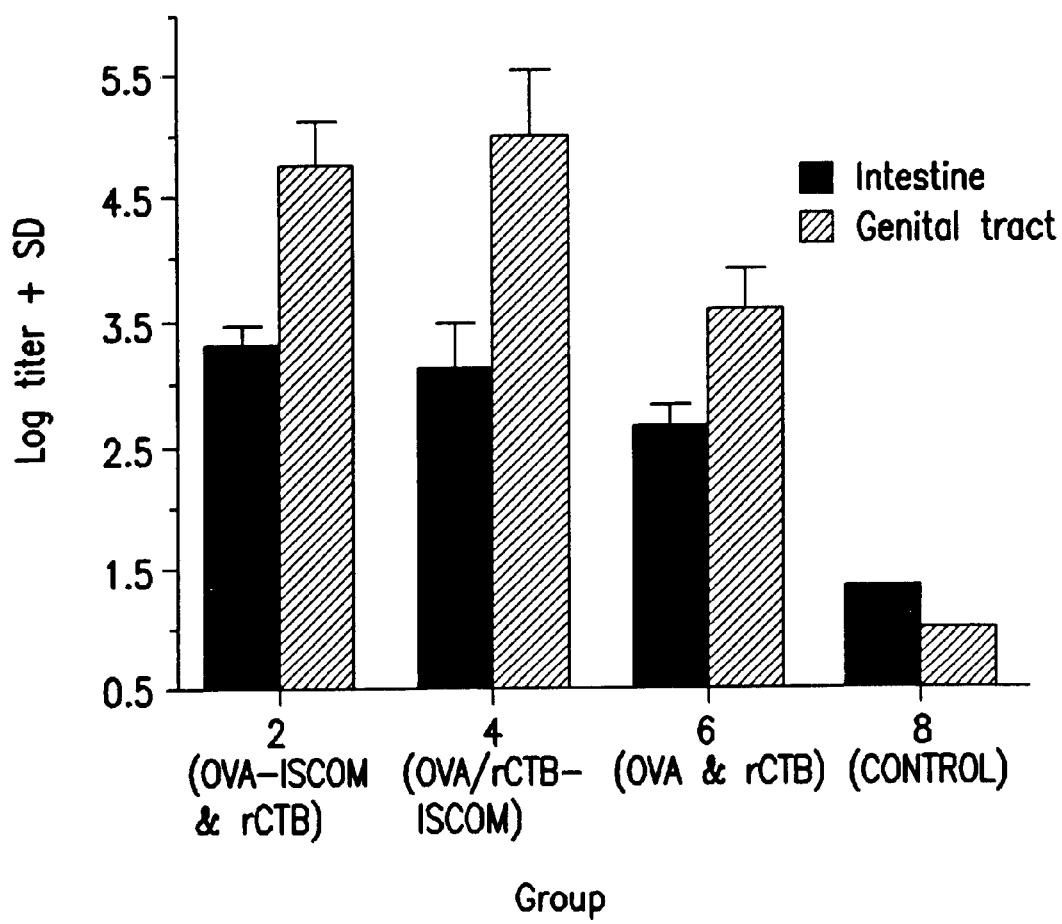
Figure 9A:
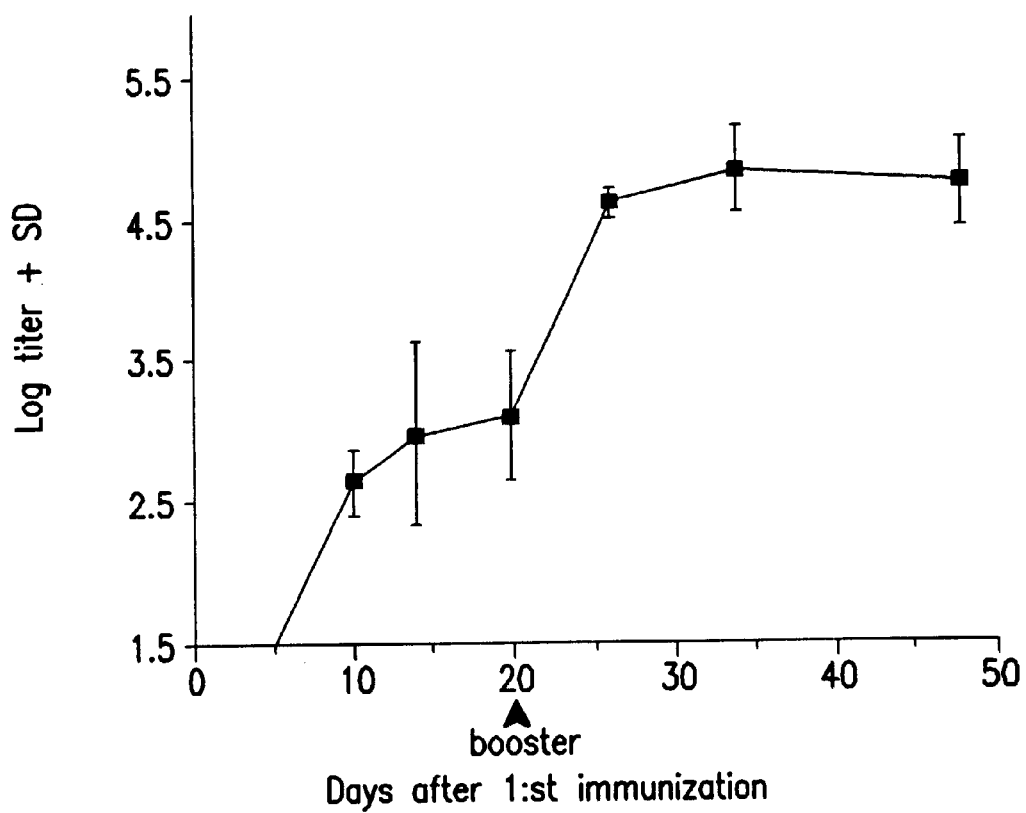
FIG. 9. The development of the serum antibody response (A, B and C) and the response in lung secretion (D) measured in ELISA during an experimental period of 48 days following immunization with influenzavirus ISCOMs™ (7 µg) twice i.n.
   A. shows the development of the total antibody response to influenza virus in serum.
   B. shows the development of antibody response to influenza virus antigen i IgG subclasses IgG1, IgG2a, IgG2b.
   C. shows the development of IgA-serum antibody response to influenzavirus antigen.
   D. shows the development of IgA-antibody response in lung secretion.
Figure 9B:
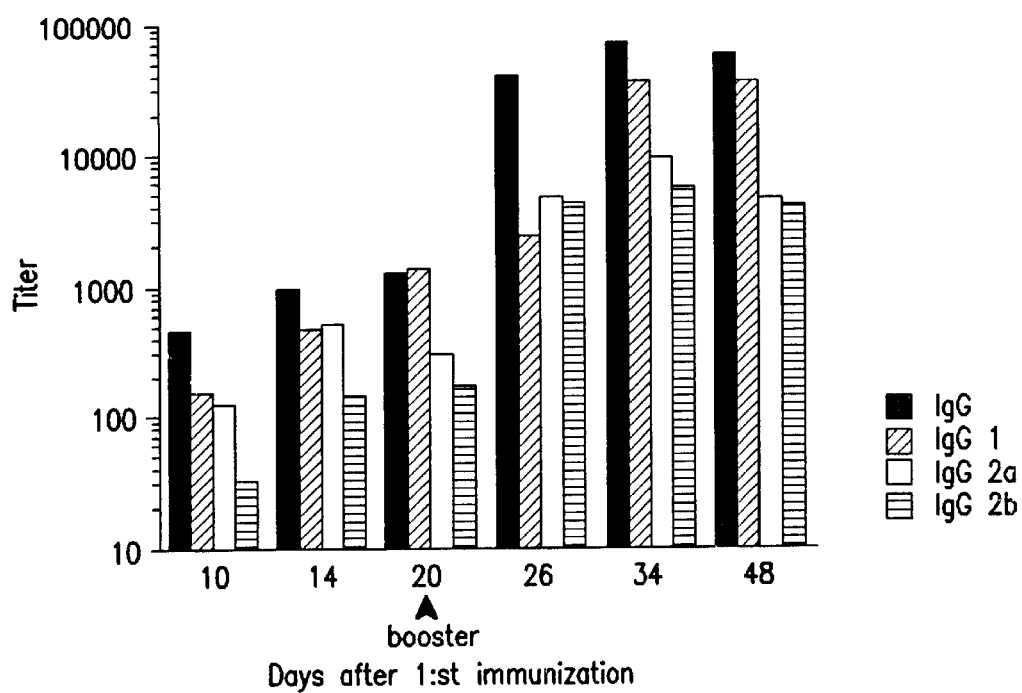
Figure 9C:
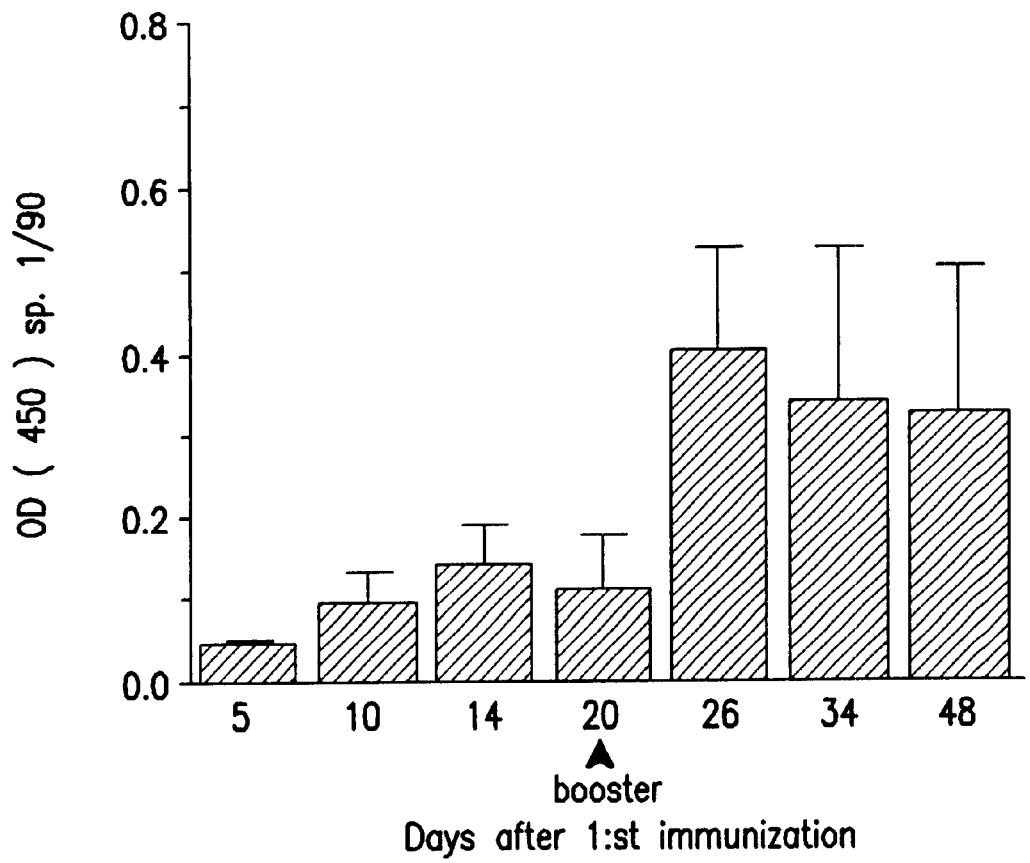
Figure 9D:
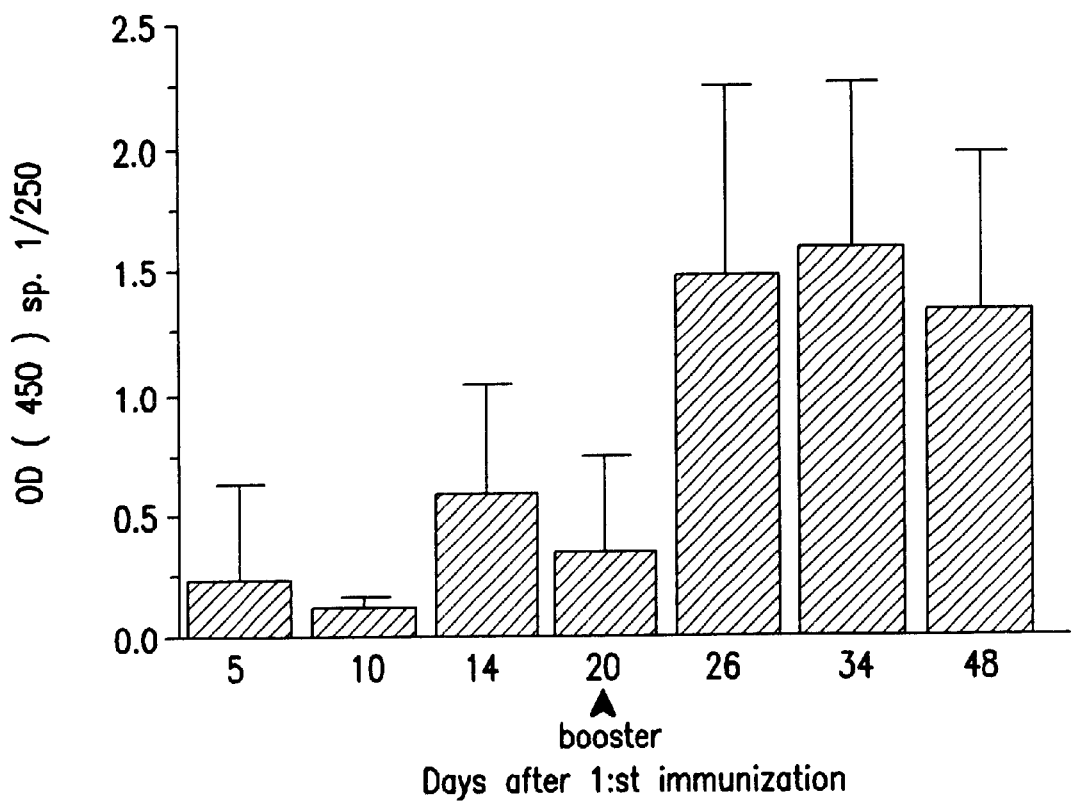
Figure 10A:
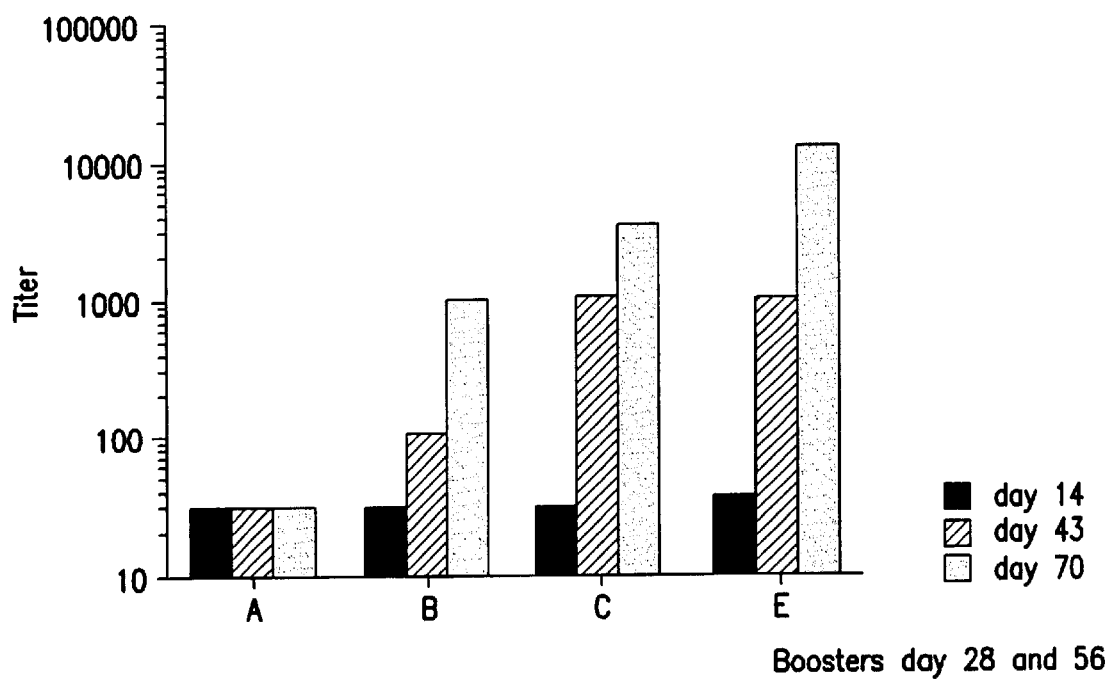
FIG. 10. Five groups of five mice (NMRI) were immunized in accordance with the following schedule.

FIG. 10A shows that OVA/PR8-ISCOM™ induce a high serum antibody response to OVA after two immunizations i.n. and even higher after three immunizations compared to OVA-ISCOMs™ without envelope protein from the influenza virus. As expected, 10 µg OVA\PR8-ISCOMs™ i.n. induced higher antibody responses than 5 µg.

Figure 10B:
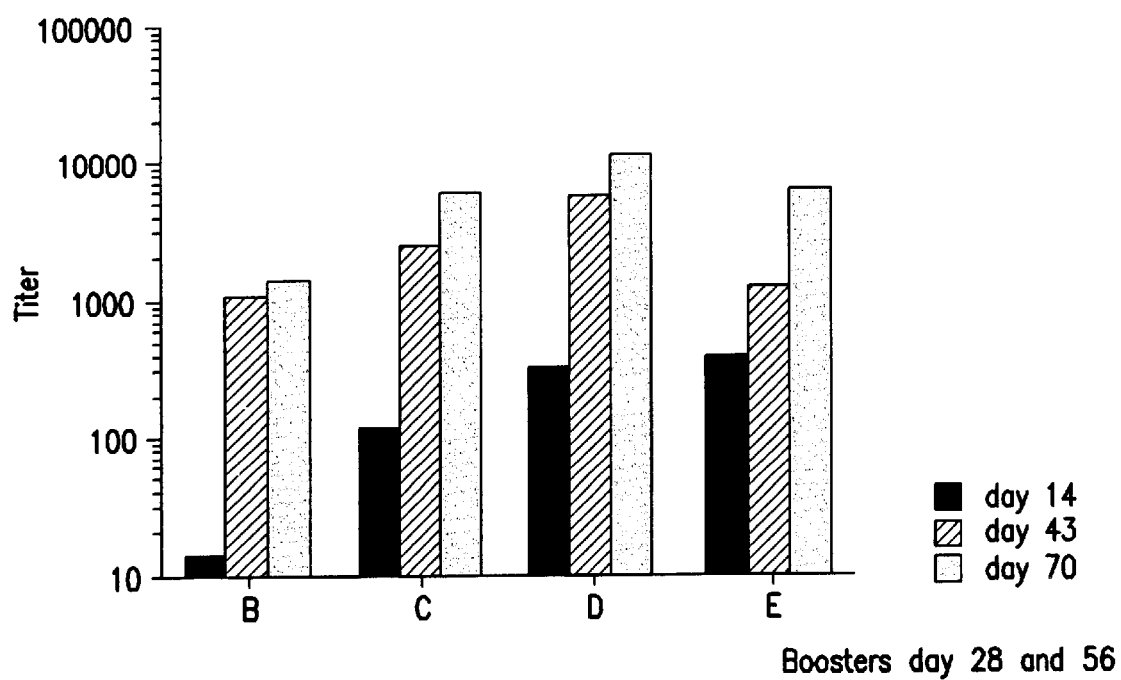

FIG. 10B shows the serum-antibody response to PR8. All ISCOM™ formulations containing PR8 induced antibody response to PR8 after i.n. immunization. This response was increased considerably after the second immunization.

Figure 10C:
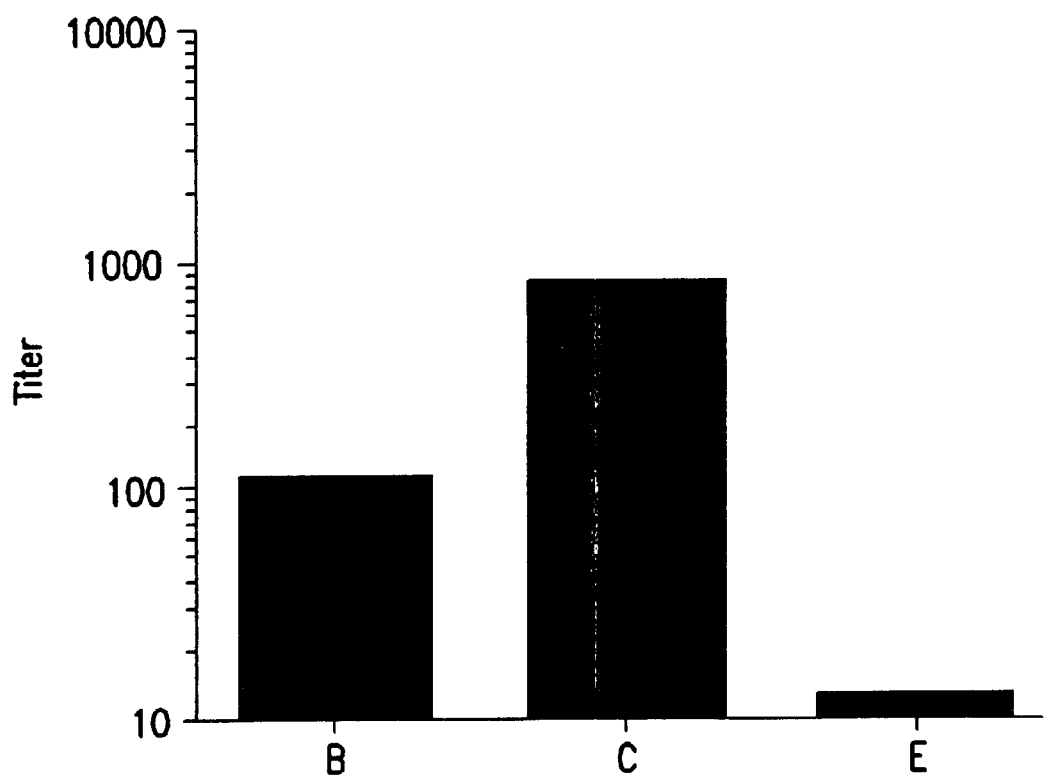

FIG. 10C shows the IgA-antibody response in secretion from lungs after three immunizations as described above. 5 µg and 10 µg of the OVA\PR8-ISCOMs™ induced dose dependent, clear-cut IgA-antibody responses after i.n. immunizations in contrast to OVA-ISCOMs™ administered subcutaneously.

Figure 10D:
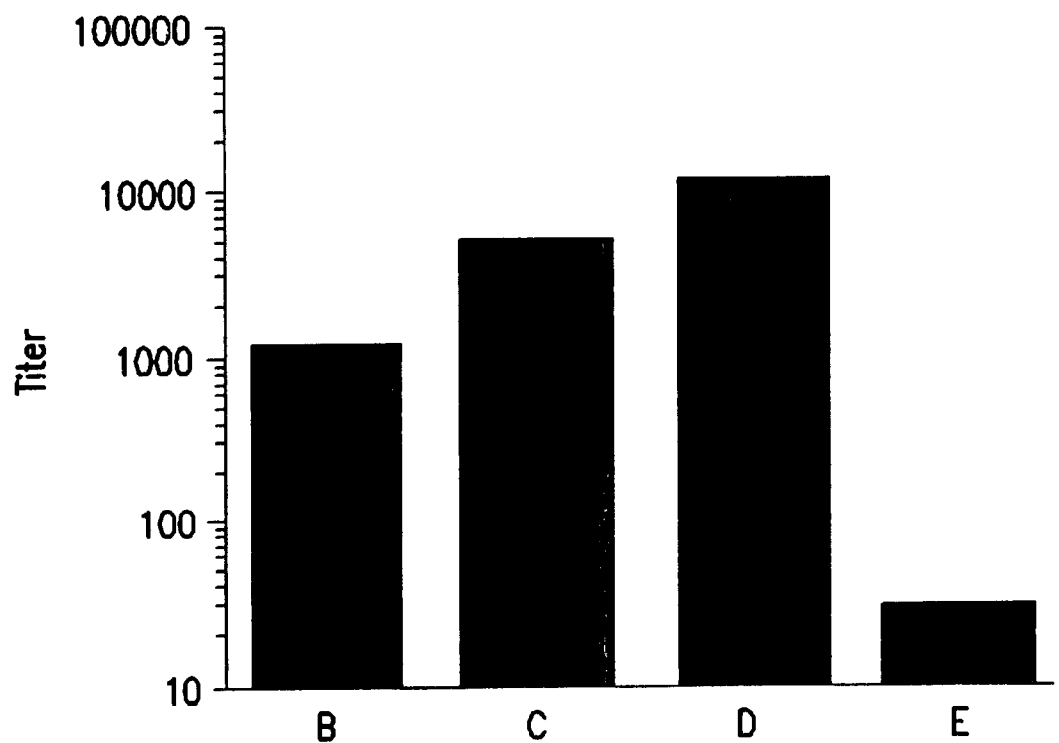

FIG. 10D shows that all ISCOM™ formulations containing PR8-antigen induce high IgA-antibody responses to PR8 in lung secretion.

Figure 10F:
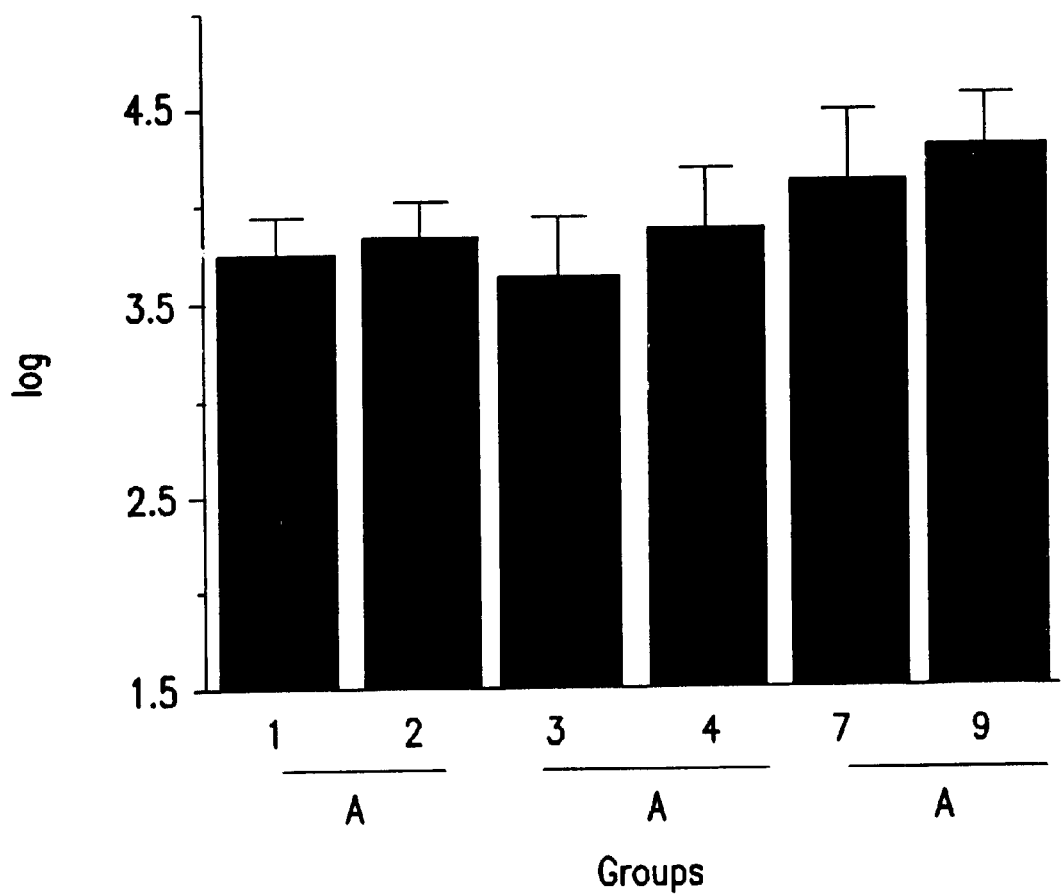

FIG. 10F shows the serum antibody response to OVA induced by formulations of ISCOMs™ containing OVA with and without target seeking molecules or formulations with OVA and ISCOM™-matrix as separate entities after two immunizations as listed on pages 20 and 21 (Example 4). The highest serum antibody titres measured by ELISA was recorded with OVA-ISCOM™ matrix formulations (C).

Figure 10G:
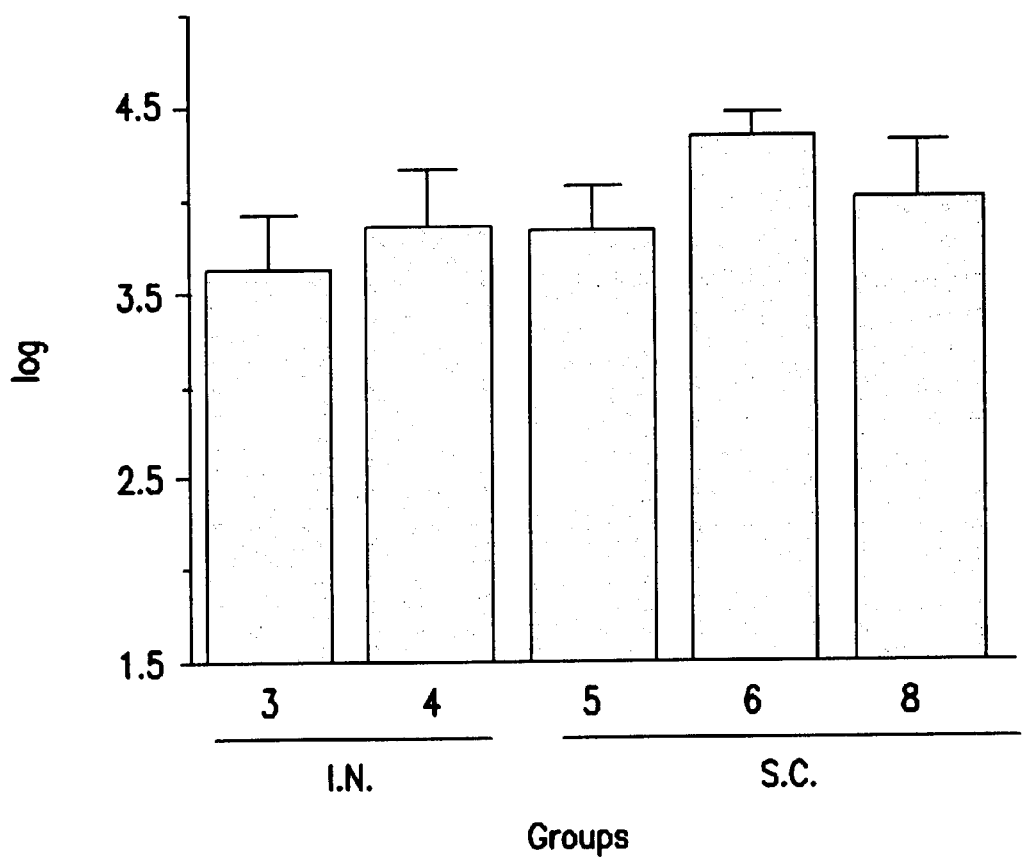

FIG. 10G compares i.n. mode of immunization with the of s.c. mode using OVA/PR8 iscom or OVA-matrix formulations. The i.n. mode of immunization induced serum antibodies of similar magnitude or only slightly less than that induced by s.c. immunization.

Figure 10H:
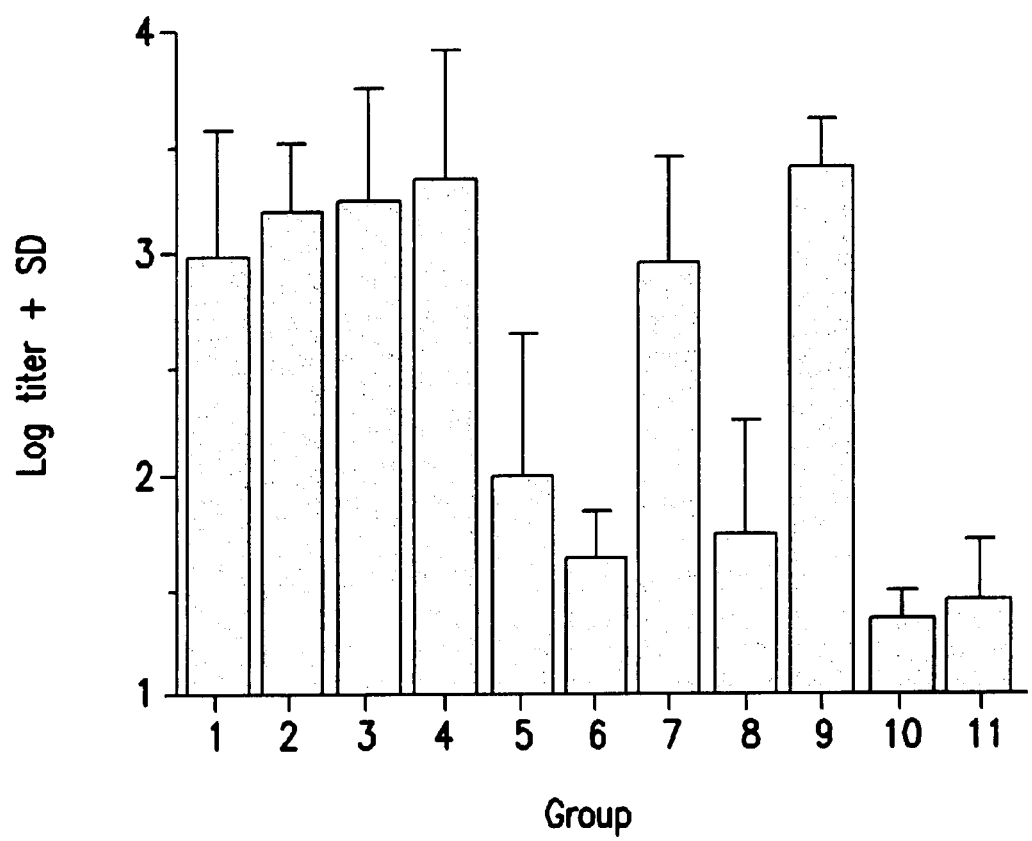

FIG. 10H shows the IgA antibody responses to OVA in lung secretions induced by formulations of ISCOMs™ with and without target seeking molecules (PR8) or by OVA mixed with ISCOM™-matrix as separate entities after two immunizations as listed on pages 39 and 40 (Example 4).

Figure 10I:
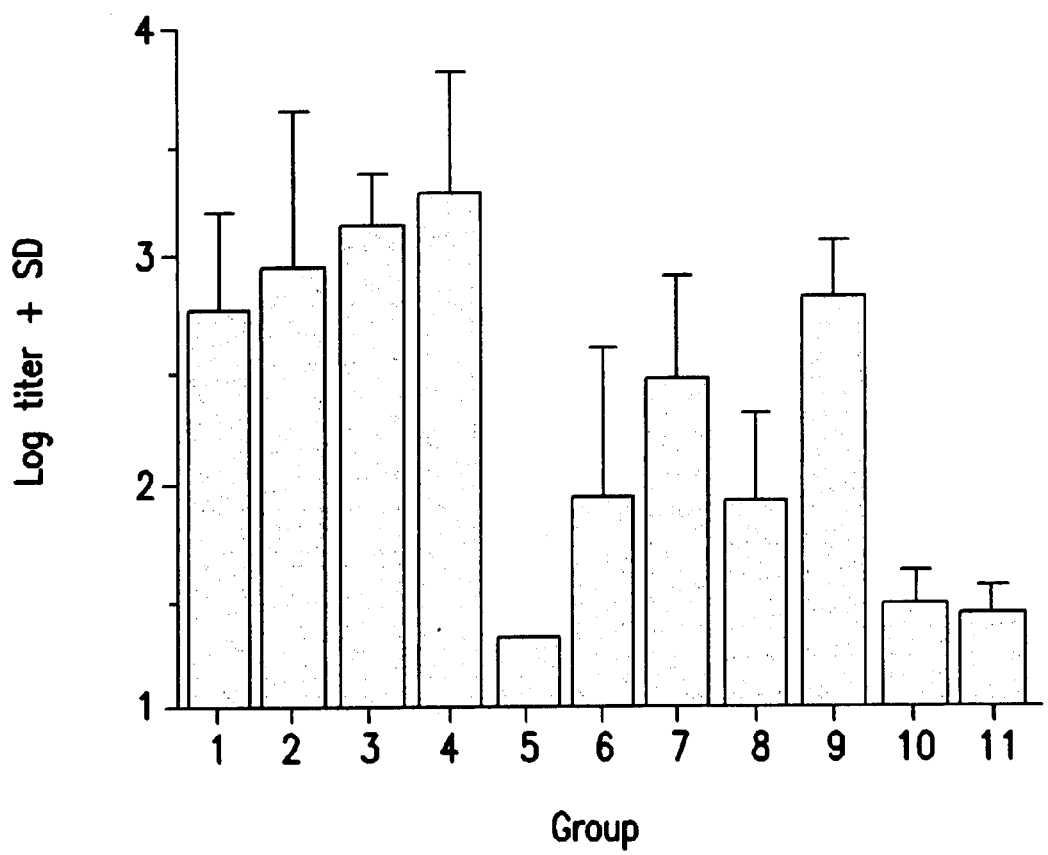

FIG. 10I shows the IgA antibody response to OVA in the genital tract secretions induced by formulations of iscoms with and without target seeking molecules or by OVA mixed with iscom-matrix as separate entities after two immunizations as listed on pages 39 and 40 (Example 4).

Figure 11A:
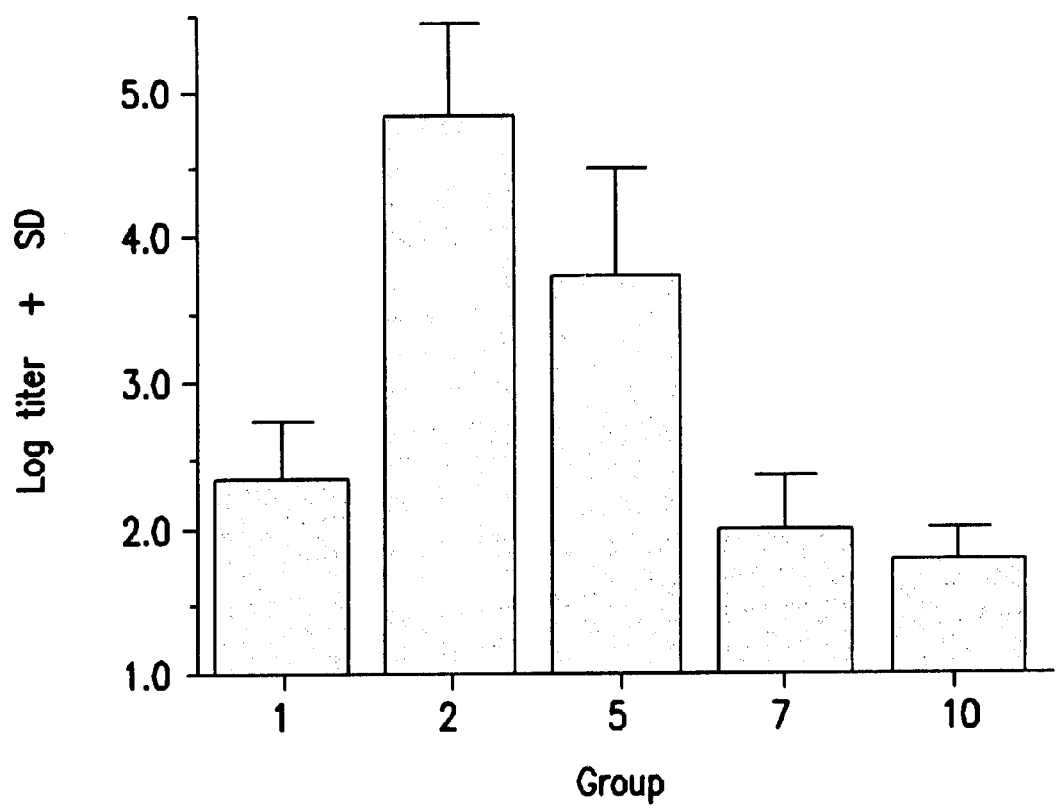

FIG. 11A shows the IgA-response in lung secretion (day 77) from mice two weeks after two i.n. immunizations with an interval of 9 weeks with ISCOM™ containing gB from Herpes simplex 2 (gB2) according to Example 5.

Figure 11B:
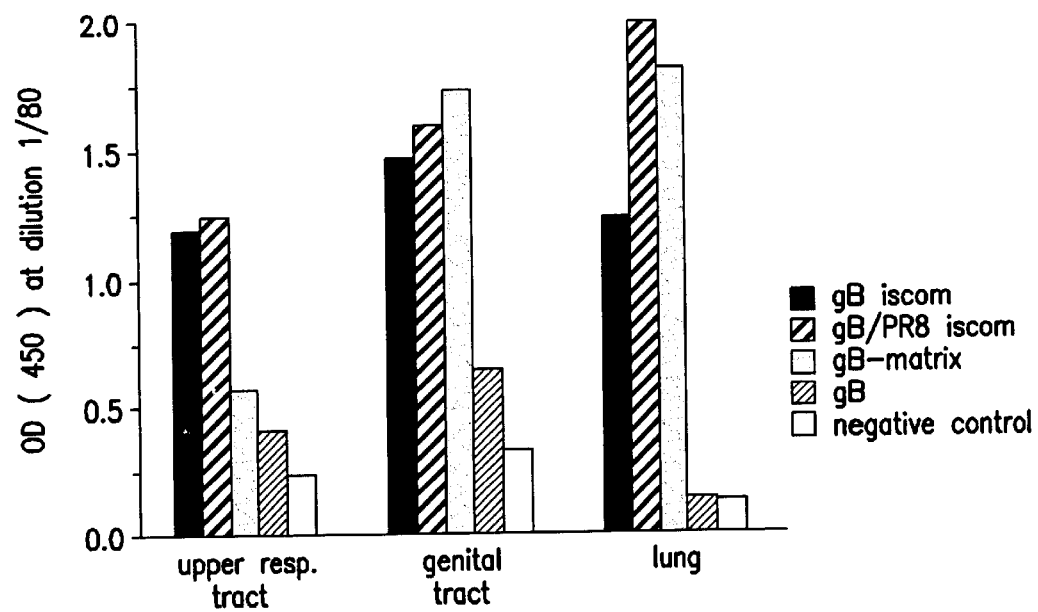

FIG. 11B shows the IgA-response to gB2 in secretions (day 113) from different mucous membranes from mice (lungs, upper respiratory tracts and the genital tract) which have been immunized i.n. with ISCOMs™ else as described in FIG. 11A and Example 5.

Figure 11C:
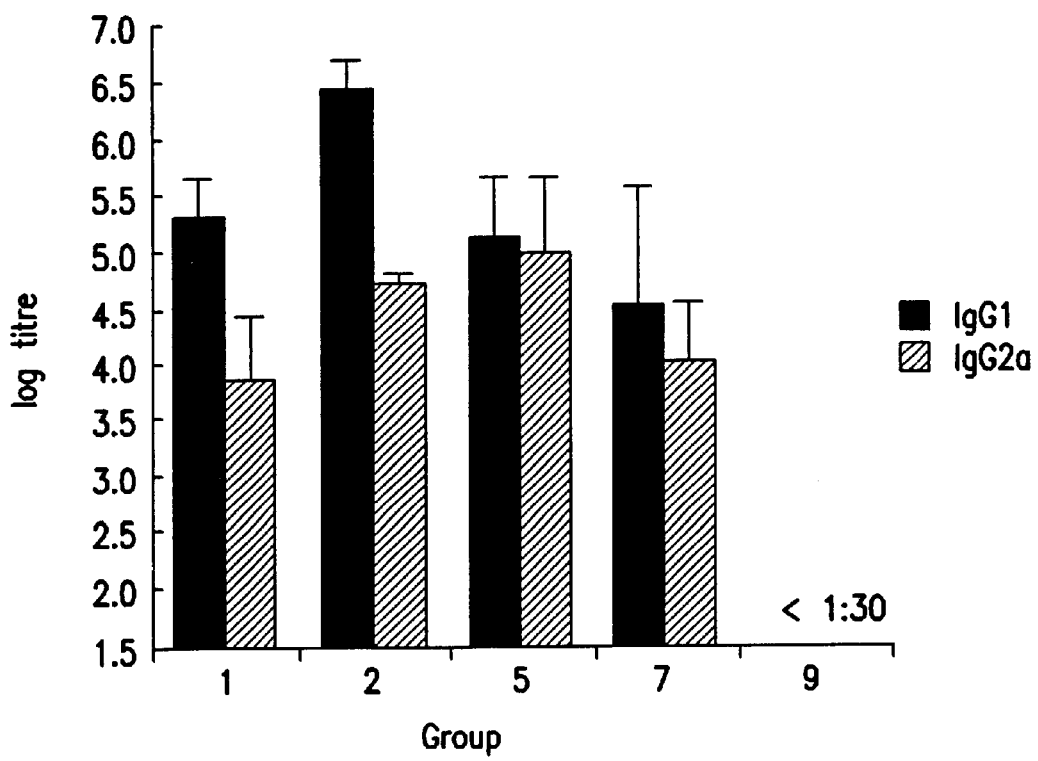

FIG. 11C shows the IgG subclass (IgG1 and IgG2a) response to gB2 in serum (day 77) after i.n. immunizations as described in FIG. 11A.

Figure 12A:
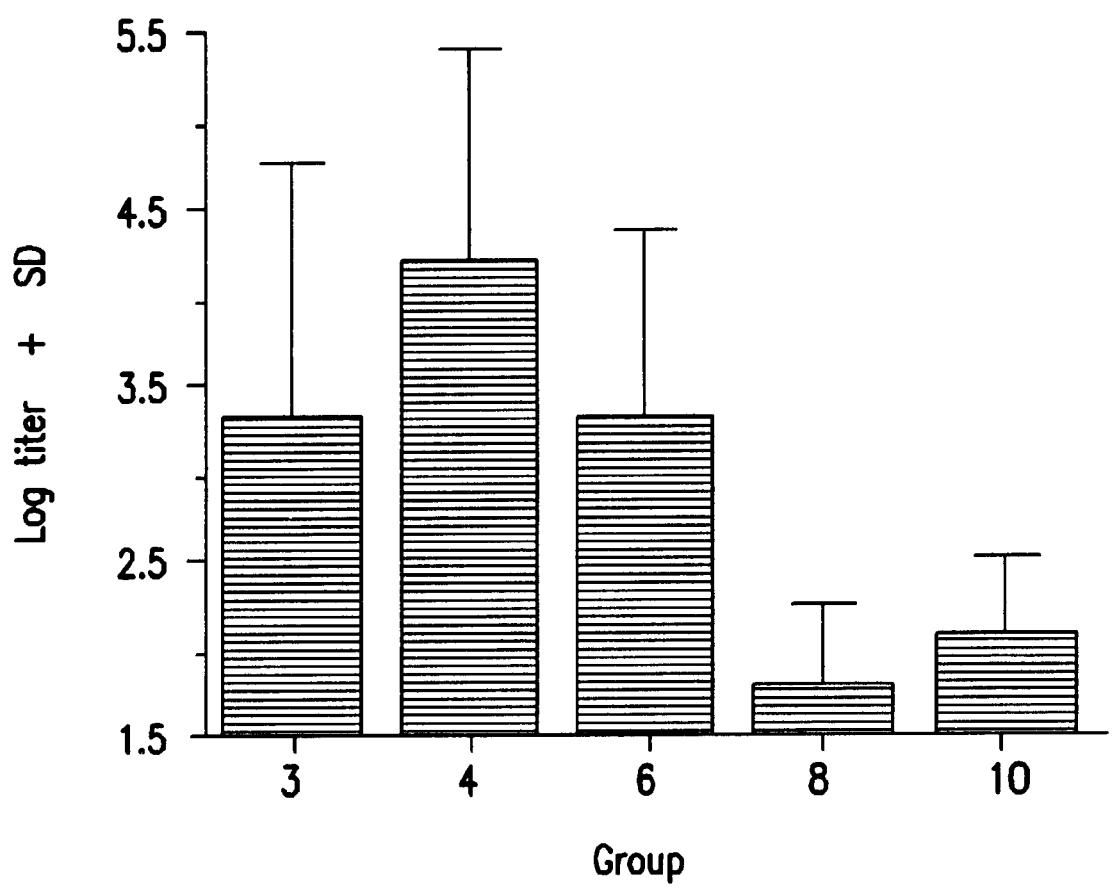

FIG. 12A shows the IgA-response in lung secretion from mice 14 days after two i.n. immunizations (day 77) with an interval of 9 weeks with ISCOMs™ containing gD from Herpes simplex 2 (gD2) according to Example 6.

Figure 12B:
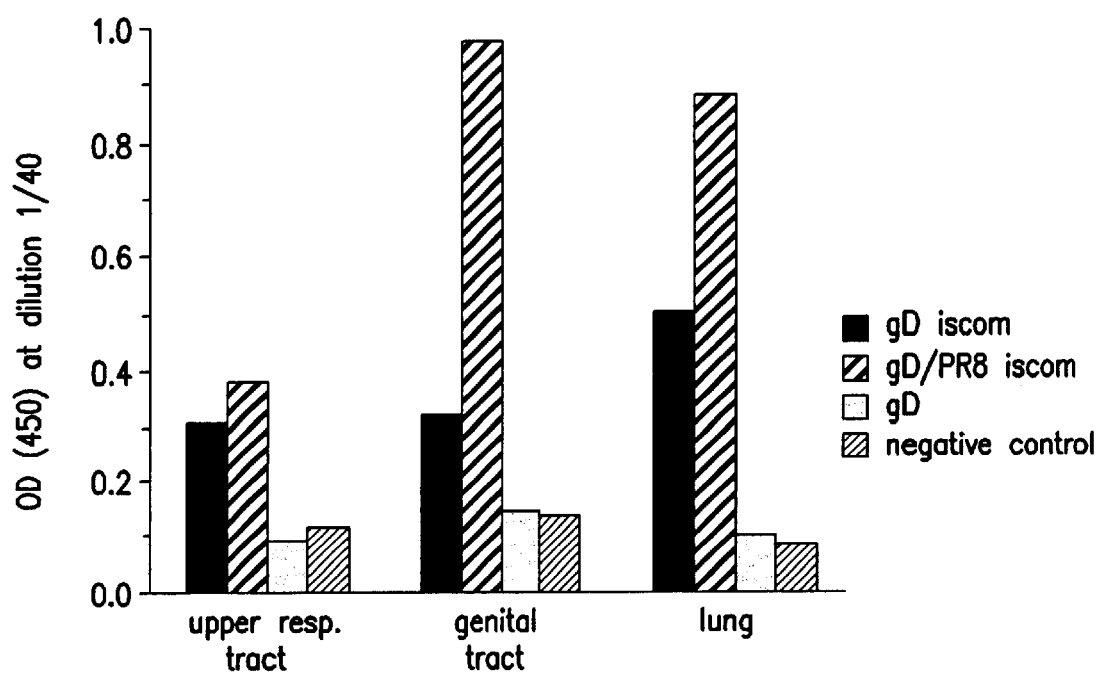

FIG. 12B shows the IgA-response to gD2 in secretions (day 113) from different organs in mice (lungs, upper respiratory tracts and genital tract) which have been immunized i.n. with ISCOMs™ that have been described in FIG. 12A and in Example 6.

Figure 12C:
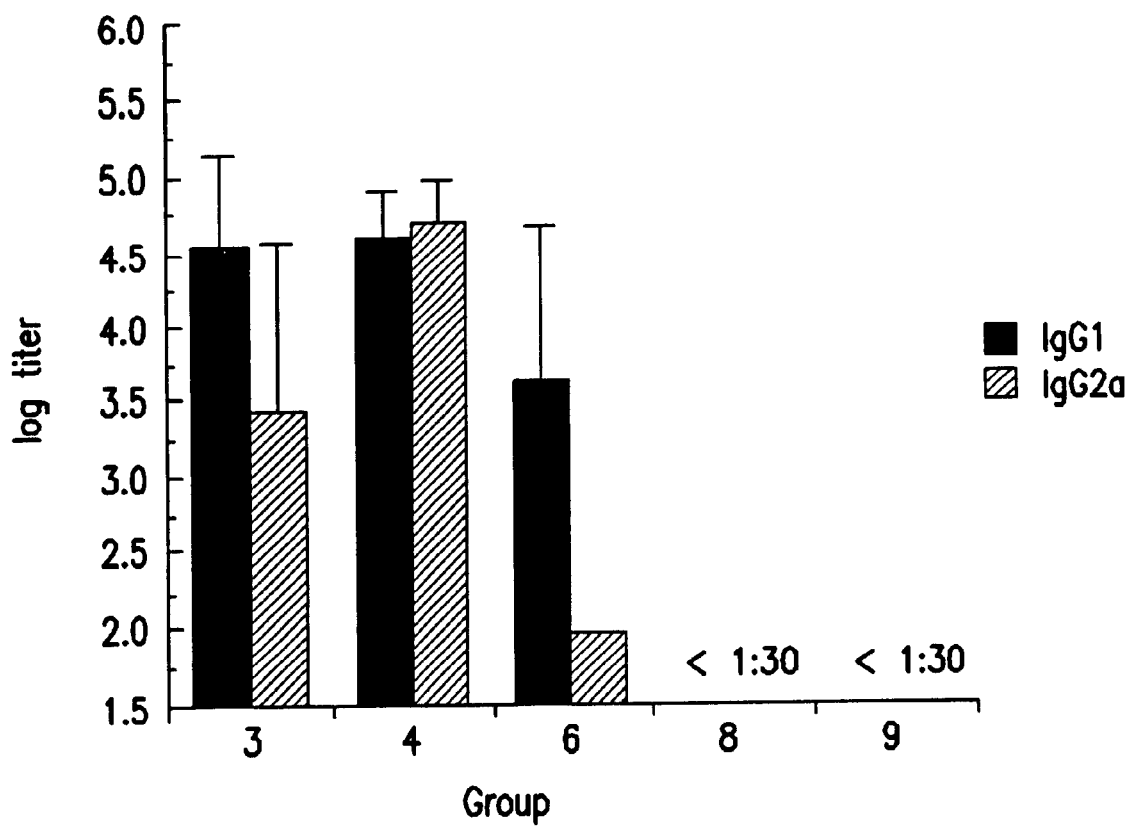

FIG. 12C shows the IgG subclass to gD2 (IgG1 and IgG2a) in serum (day 77) after i.n. immunizations as described in FIG. 12A.

Figure 13A:
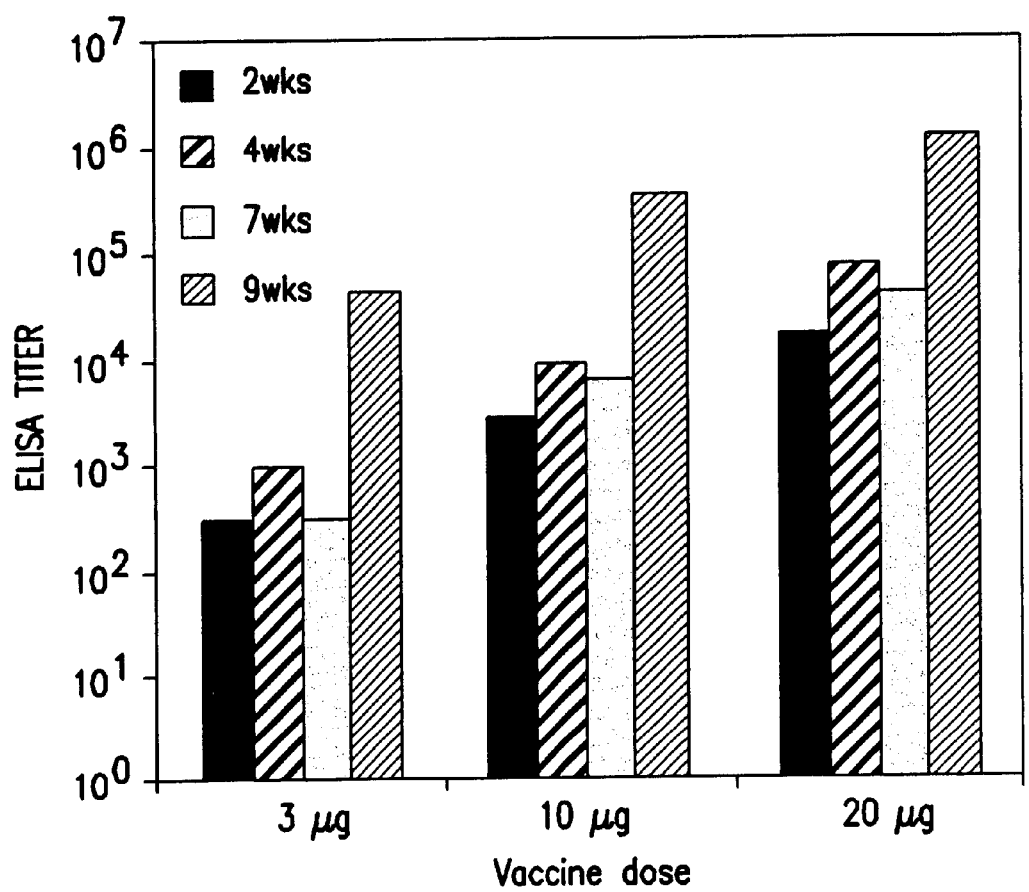

FIG. 13A. Total serum antibody responses measured in ELISA to Mycoplasma mycoides (Mm) of mice i.n. immunized twice 7 weeks apart with 3, 10 or 20 µg ISCOMs™. Sera were tested 2, 4 and 7 weeks post-first immunization and 2 weeks after booster dose.

Figure 13B:
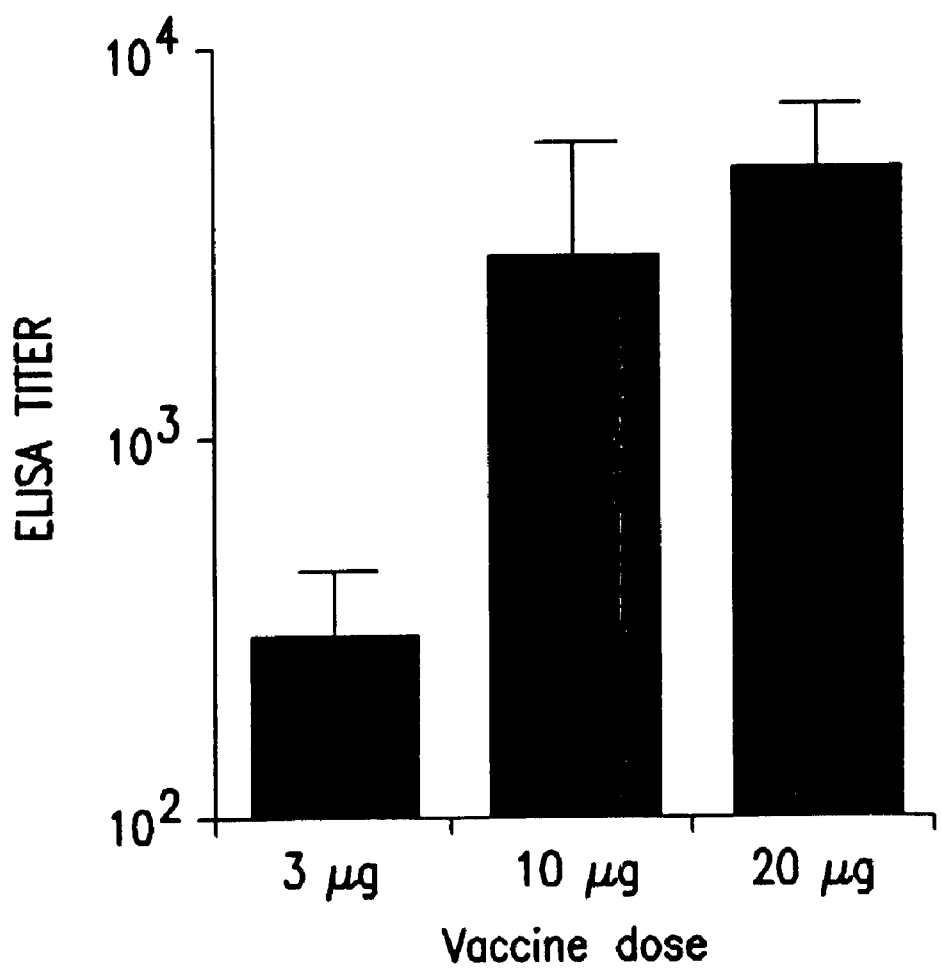

FIG. 13B. IgA response in serum measured in ELISA to Mycoplasma mycoides (Mm) collected two weeks after two intranasal immunizations of mice, seven weeks apart with different doses of ISCOMs™ containing Mm antigens.

Figure 13C:
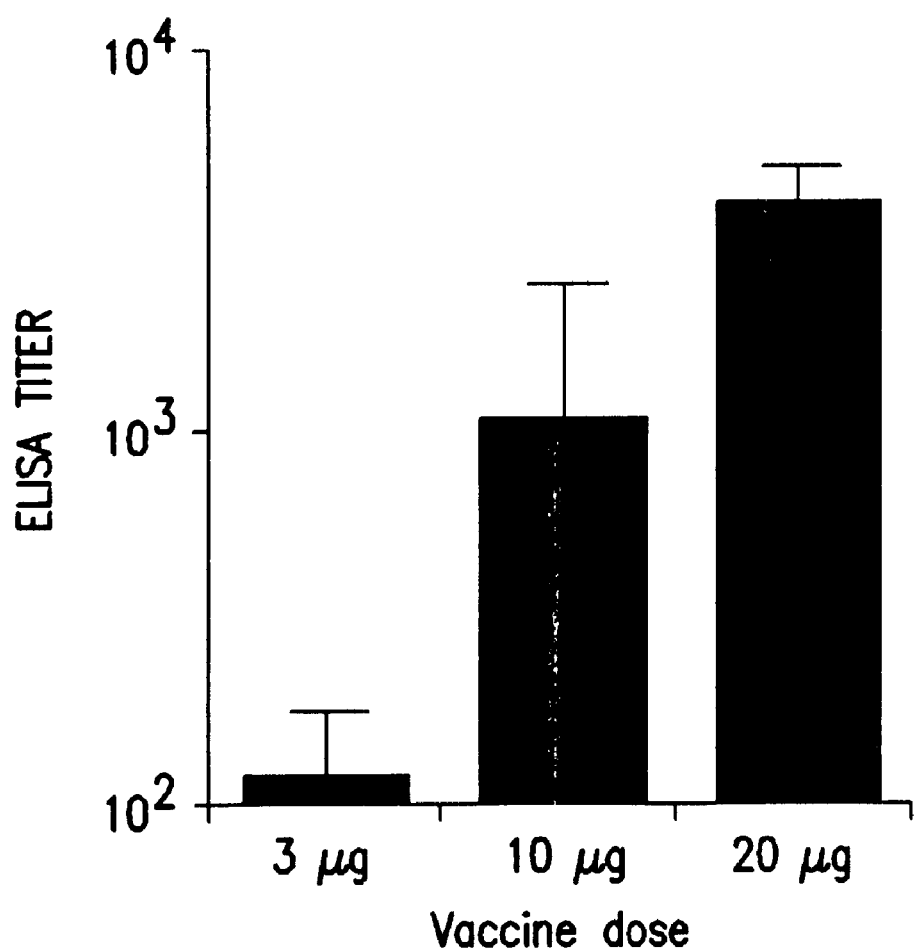
Figure 13D:
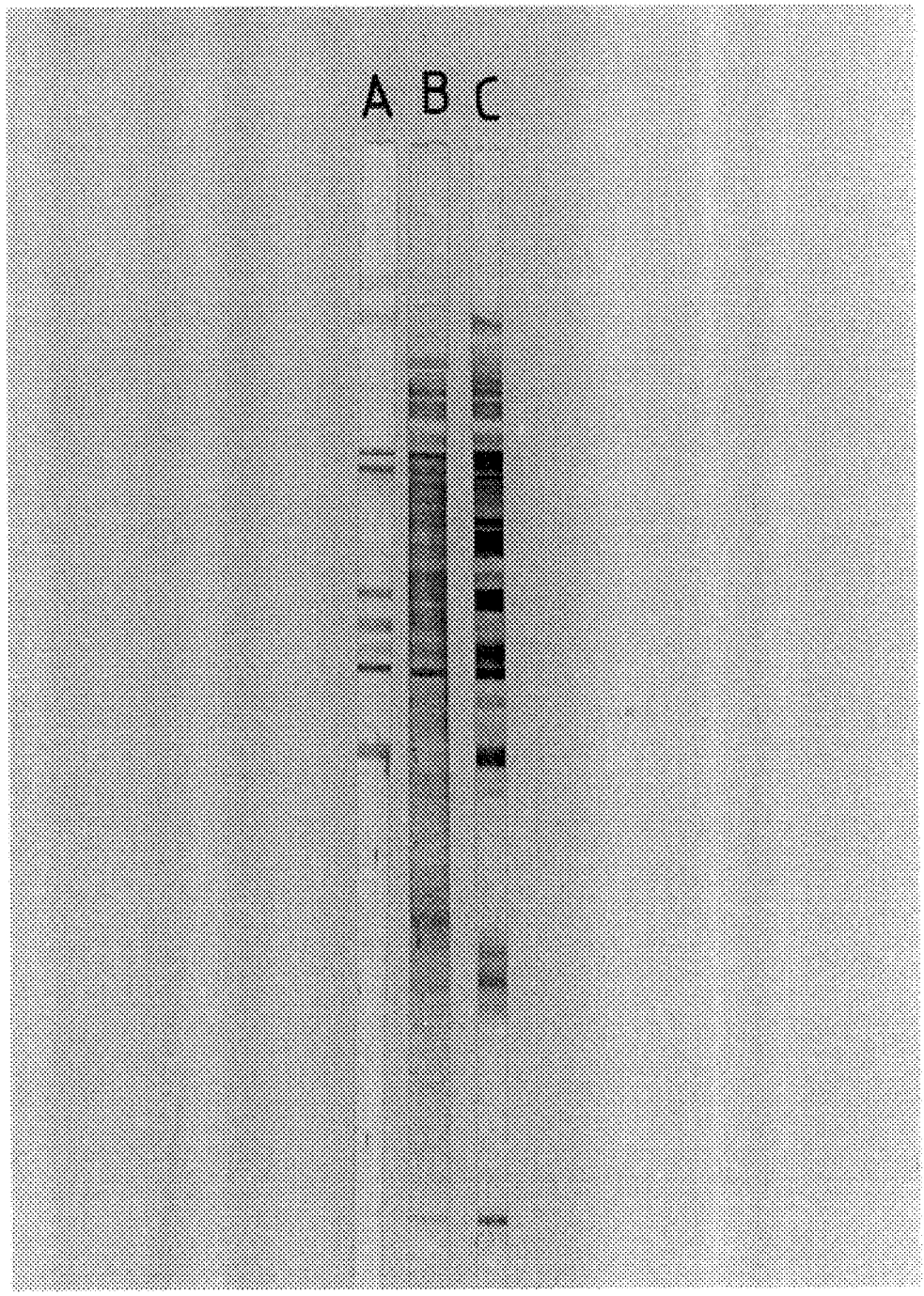
Figure 14A:
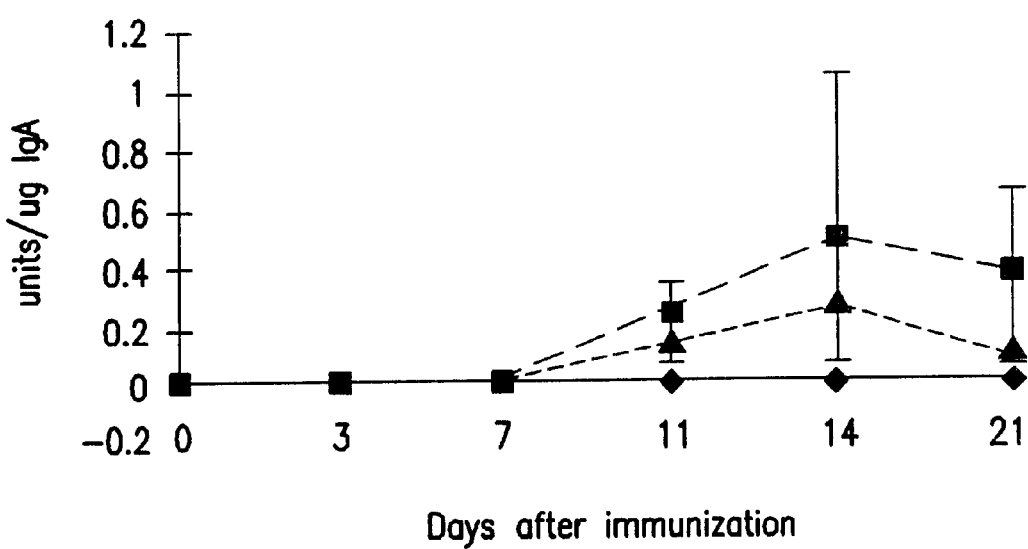
Figure 14B:
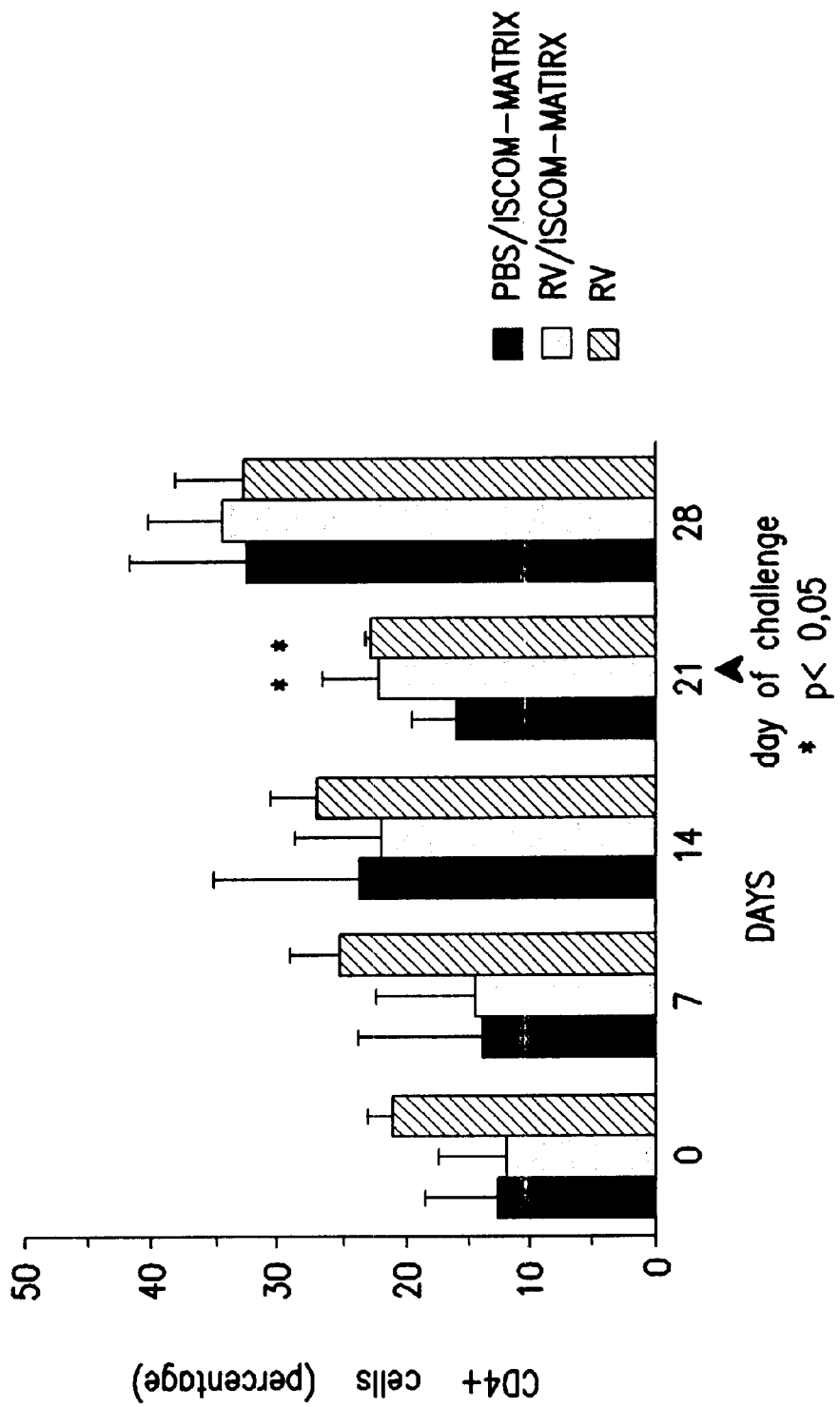
Figure 14C:
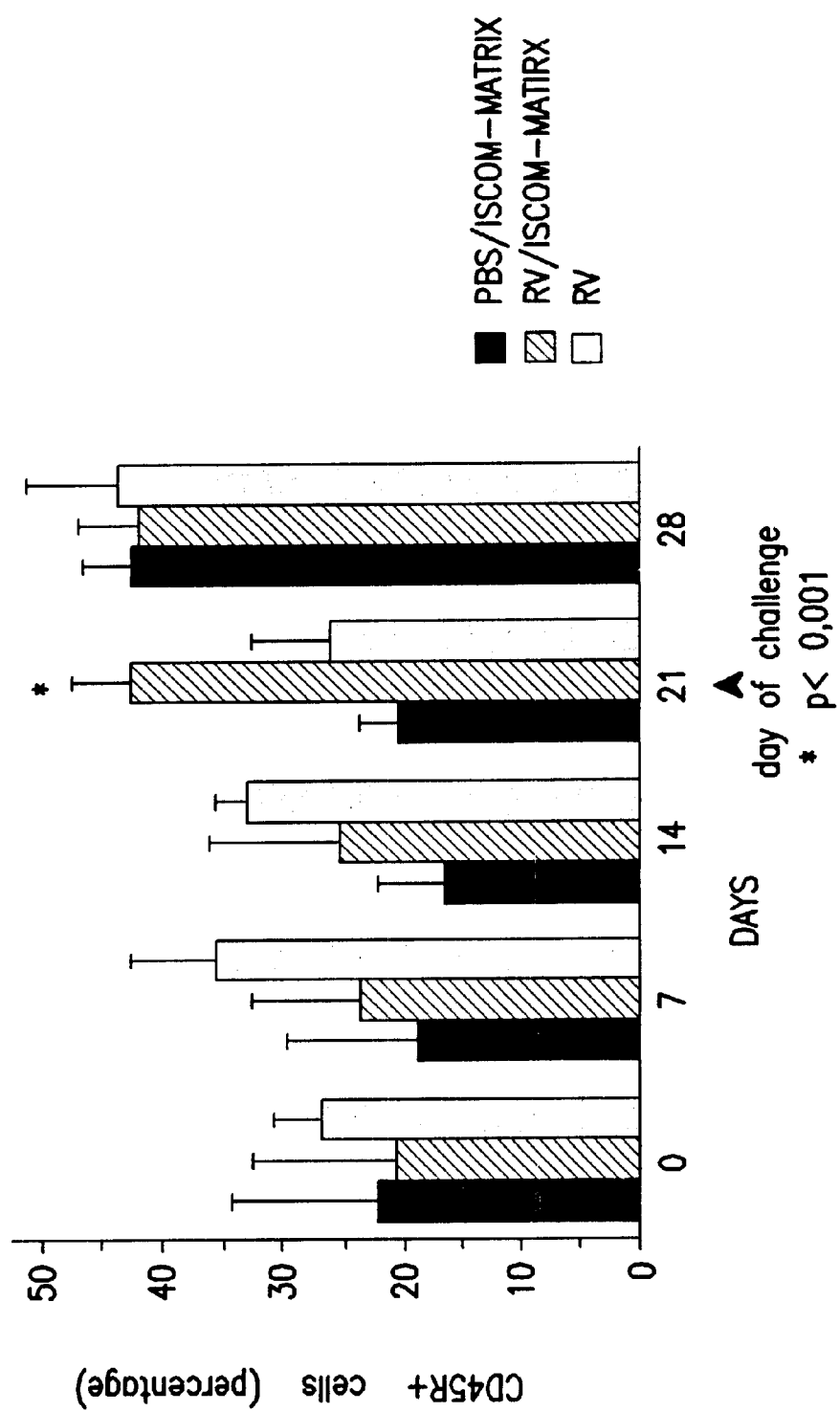
Figure 14D:
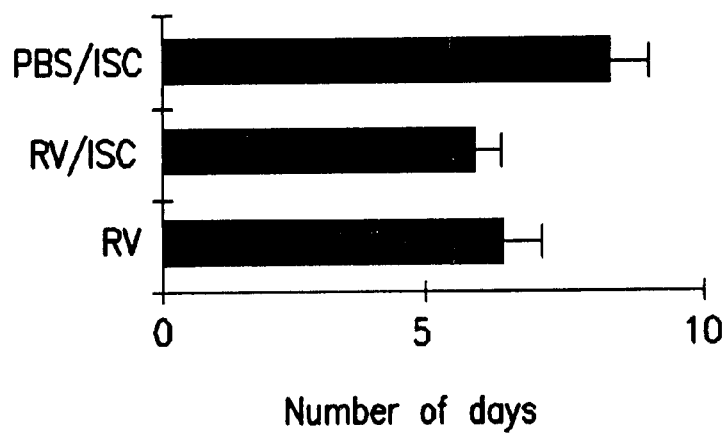
Figure 14E:
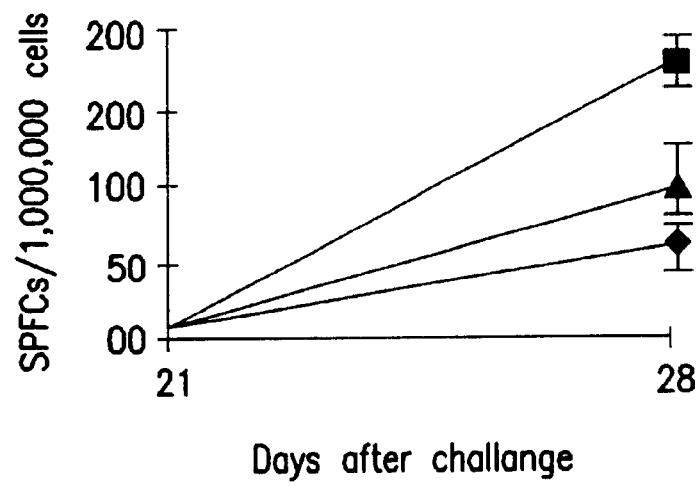
Figure 15A:
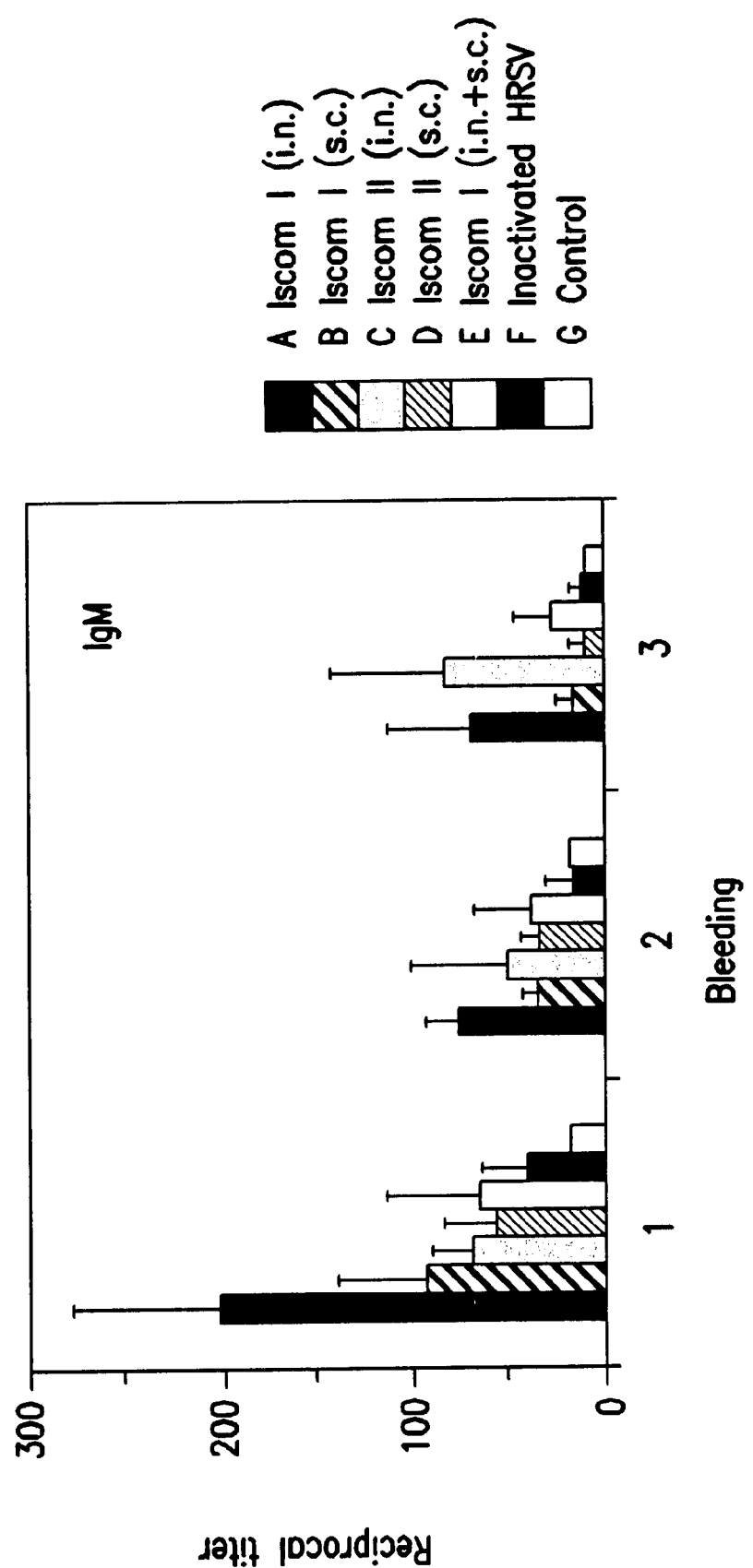
Figure 15B:
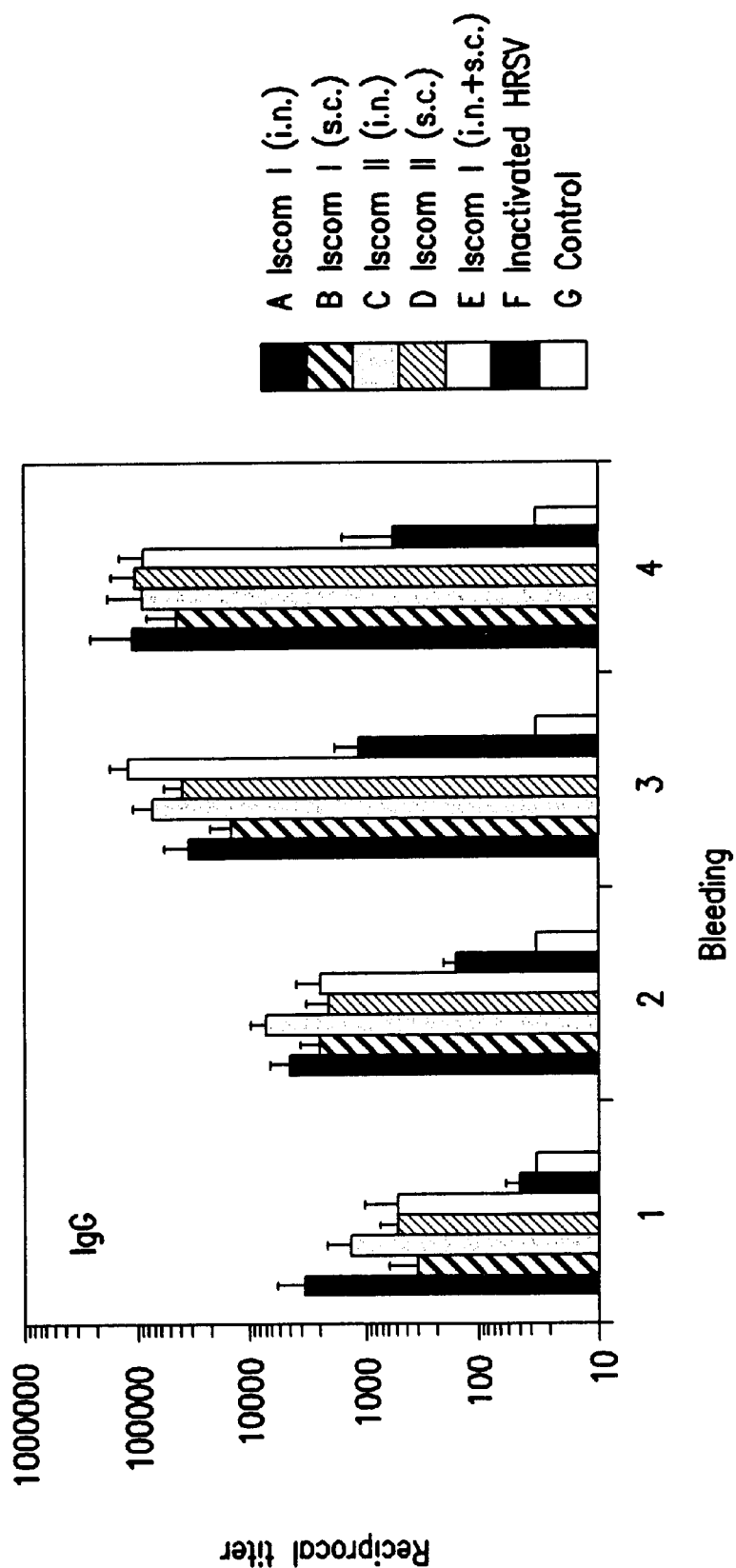
Figures 1, 15C:
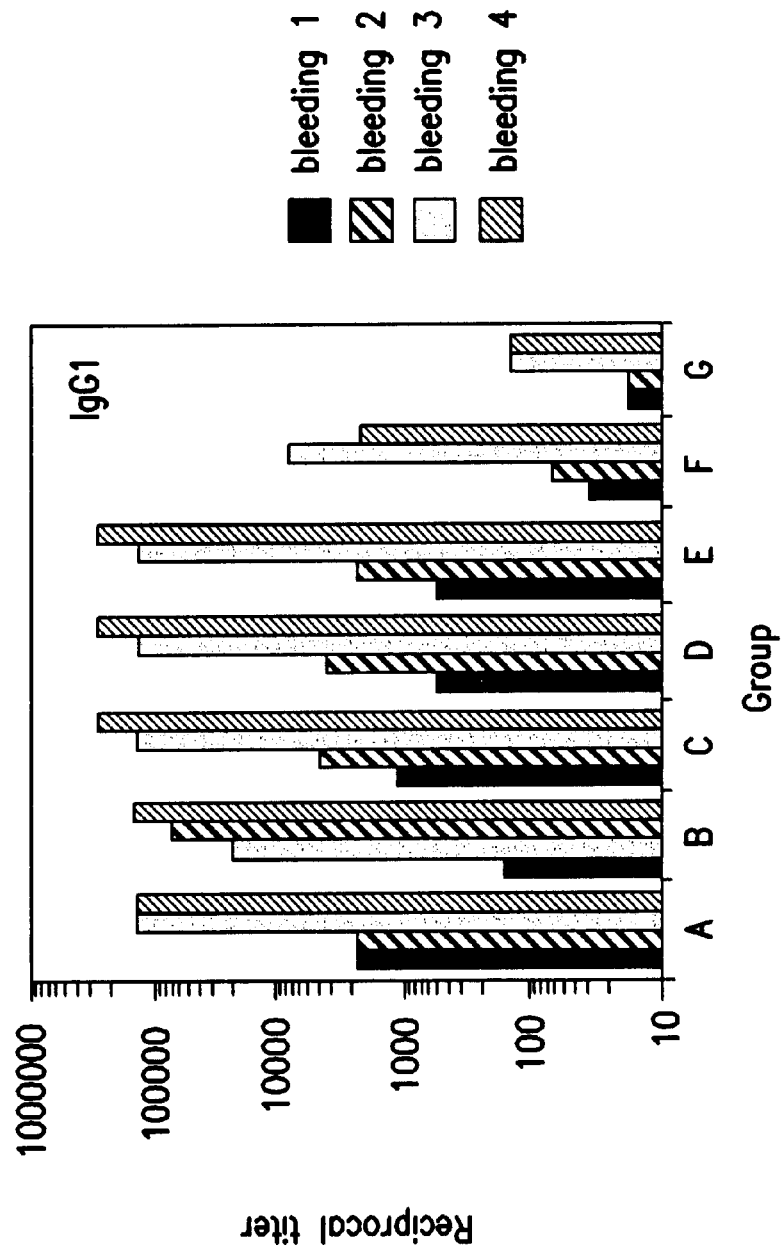
Figures 2, 15C:
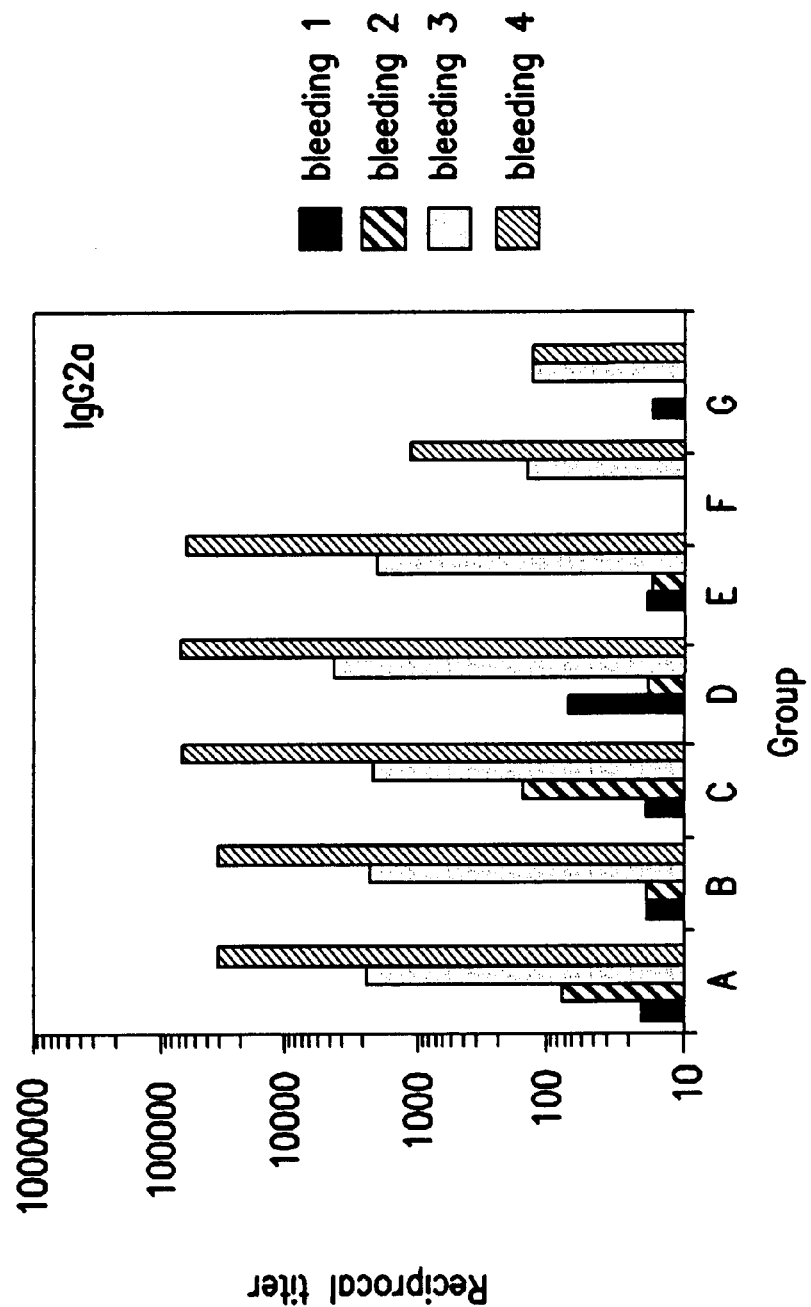
Figures 3, 15C:
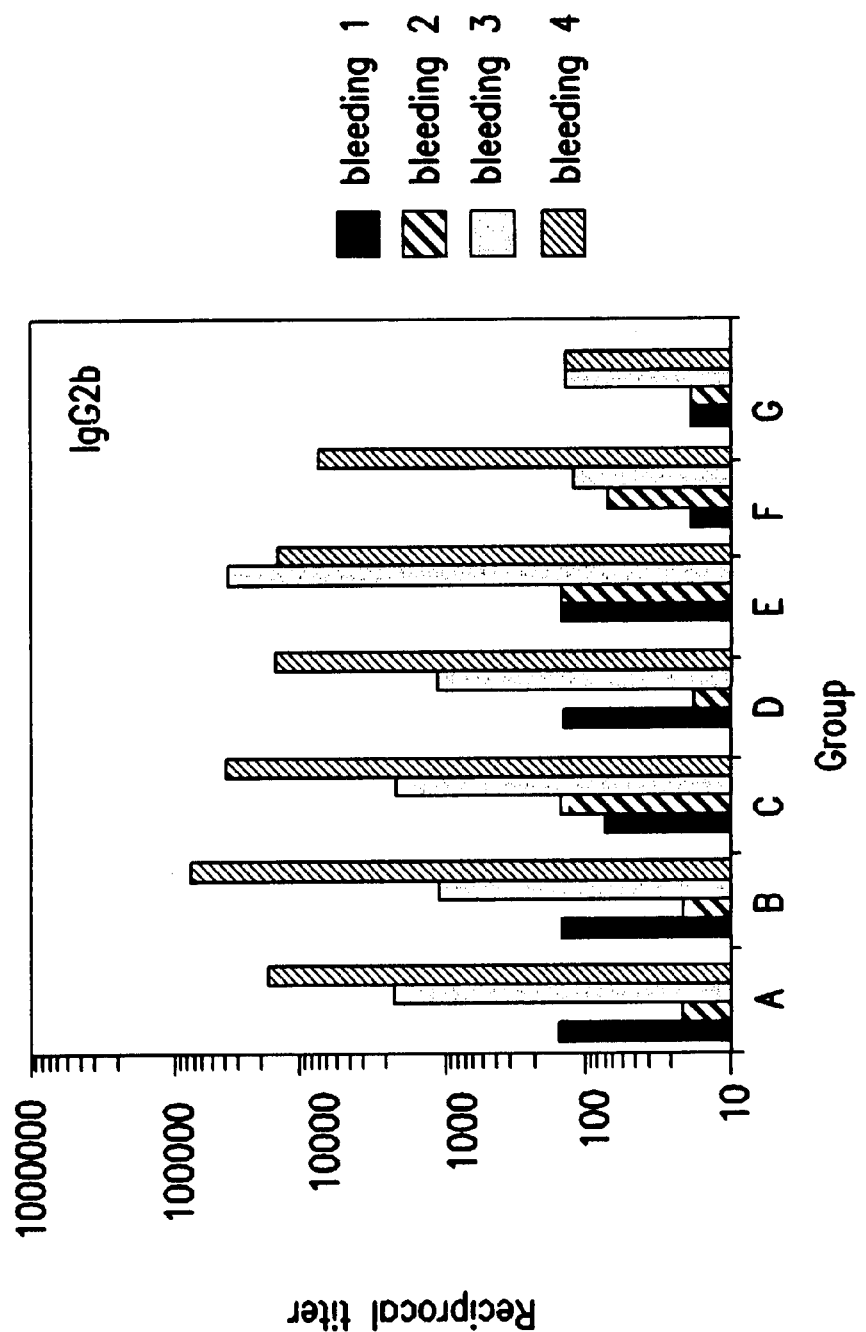
Figures 4, 15C:
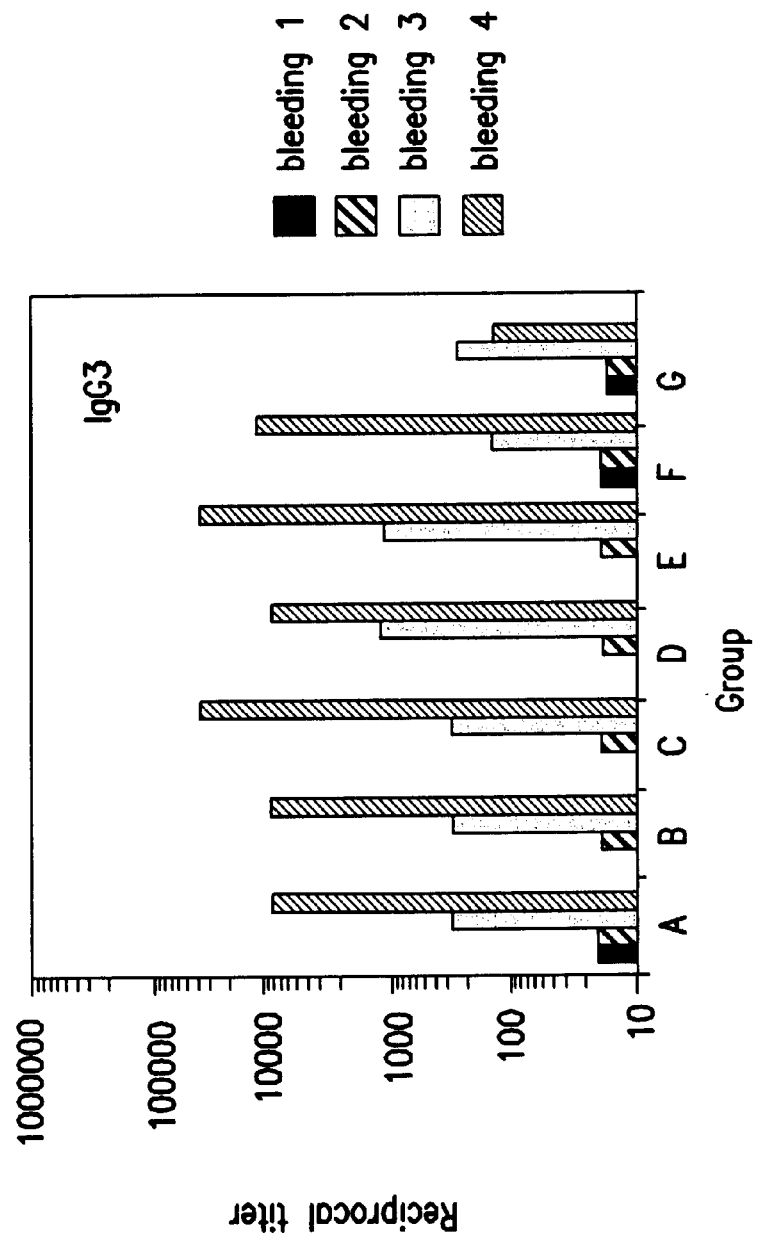
Figure 15D:
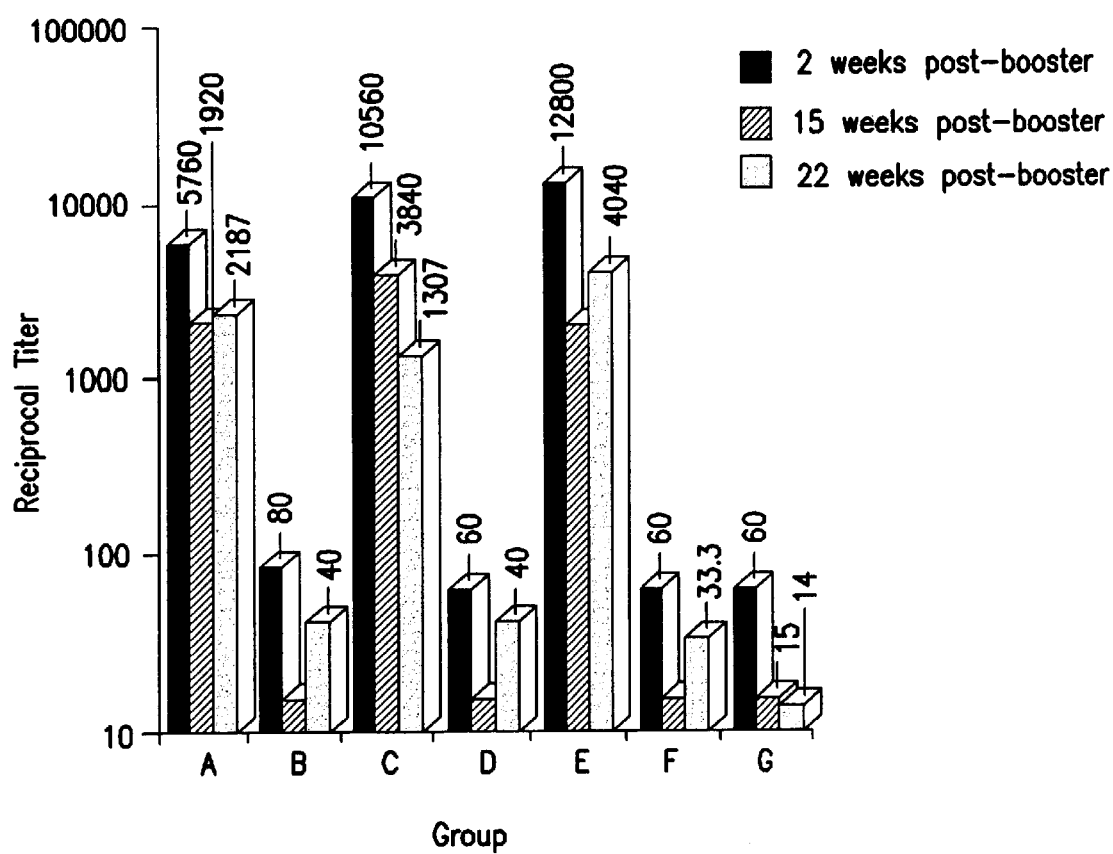
Figure 15E:
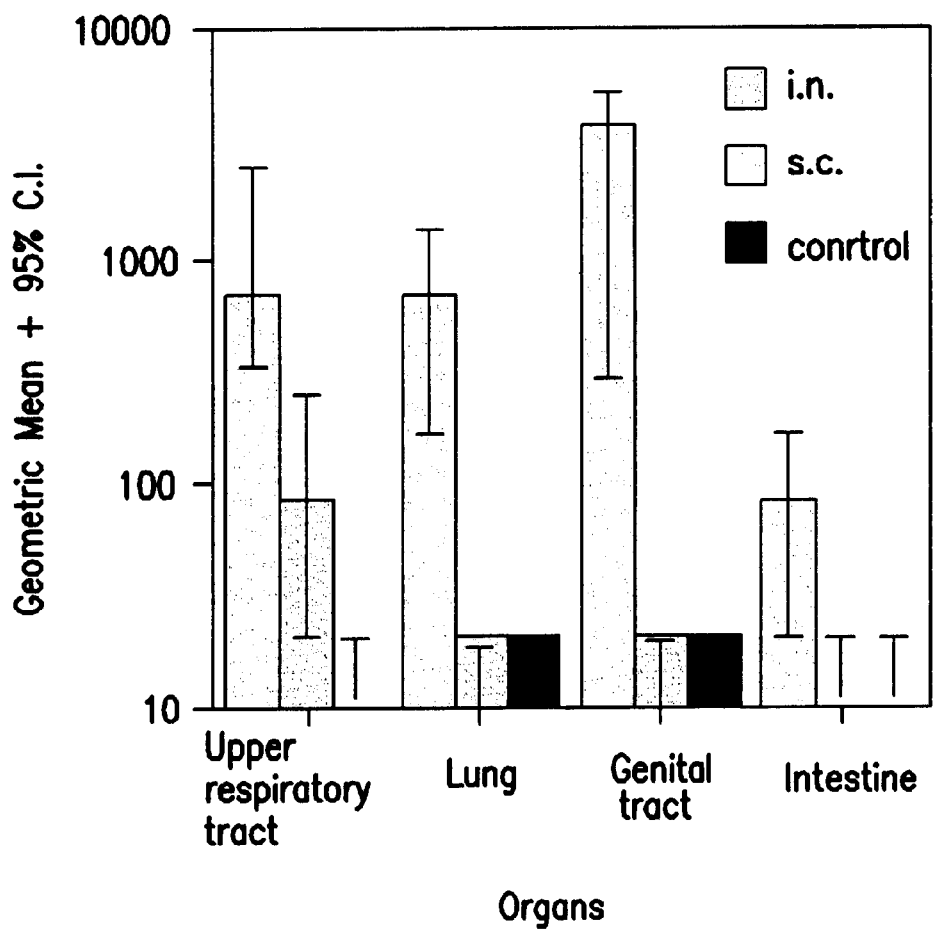

FIG. 13C. IgA response in lungs secretion measured in ELISA to Mycoplasma mycoides (Mm) collected two weeks after two intranasal immunizations of mice with three different doses of ISCOMs™ containing Mm antigens.

FIG. 13D. Western blot analysis against Mycoplasma mycoides (Mm) antigen: Lane A. Detection with lung secretion obtained from mice two weeks after the second immunization carried out intranasally (i.n.) seven weeks apart with iscoms containing Mm antigens. Lane B. Serum from mice immunized i.n. as described in Lane A; Lane C. Serum from mice immunized subcutaneously (s.c.) as the schedule in Lane A.

FIG. 14A. Specific IgG serum antibodies to rotavirus (RV) after oral vaccination; Means of groups were analyzed one-way ANOVA. RV-vaccinated group vs PBS-vaccinated group;

■ RV/ISC-matrix-vaccinated group

RV-vaccinated group

♦ PBS/ISC-matrix vaccinated group

FIG. 14B. The lymphocyte subpopulation of CD4+ cells (percentage) in peripheral blood at increasing time span after oral vaccination with rotavirus (RV) vaccines with and without ISCOM™-matrix adjuvant and subsequent challenge infection day 21 Means of groups were analyzed by one-way ANOVA.

FIG. 14C. The lymphocyte subpopulation CD45R+ cells (percentage) in peripheral blood at increasing time span after oral vaccination with rotavirus (RV) vaccines with and without ISCOM™-matrix adjuvant and subsequent challenge infection day 21 Means of groups were analyzed by one-way ANOVA.

FIG. 14D. Virus excretion after challenge infection.

FIG. 14E. Specific IgA producing cells in blood after vaccination and subsequent challenge infection day 21.

♦ PBS/ISCOM™-matrix (no RV antigen)

■ RV/ISCOM™-matrix

RV (inactivated virus)

FIG. 15A. IgM serum antibody titres (geometric mean titres and 95% confidence limits) of mice to respiratory syncytial virus (RSV) measured by ELISA following two intranasal or two subcutaneous immunizations 6 weeks apart, with HRSV iscos or inactivated virus. First bleeding (1): two weeks after the first immunization. Second bleeding (2): five weeks after the first immunization. Third bleeding (3): one week after the booster. The immunizations of the groups are described in the text page 64.

FIG. 15B. IgG serum antibody titres (geometric mean and 95% confidence limits) of mice to respiratory syncytial virus (RSV) measured by ELISA following with HRSV iscoms or inactivated HRSV as described in the text page 64. Bleedings as described in 15A. First bleeding (1): two weeks after the first immunization. Second bleeding (2): five weeks after the first vaccination. Third bleeding (3): one week after the booster. Fourth bleeding (4): three weeks after the booster.

FIG. 15C. Serum IgG subclass response to RSV measured by ELISA following intranasal or subcutaneous immunizations with HRSV iscoms or inactivated HRSV as described in the text page 64. Bleedings for serum were carried out as described in FIG. 15B.

FIG. 15D. IgA antibody titres from lung secretion of mice to respiratory syncytial virus (RSV) 2, 15 and 22 weeks after the booster measured by ELISA following the immunization schedules lined up in the text (page 64). The lungs were collected and secretions extracted as described in Example 2.

FIG. 15E. IgA antibody response to RSV in secretions from various organs i.e. upper respiratory tract, lung, genital tract and intestine. The secretions were extracted from the various organs two weeks after the second immunization as described in Example 2. The immunization schedule as described in the text page 64.

TABLE 1

| Group | IgG | IgG1 | IgG2a |
|---|---|---|---|
| 1 ova | 2,09 ± 0,68 | 2,30 ± 0,94 | 1,48 |
| 2 ova-iscom | 4,03 ± 0,65 | 4,17 ± 0,79 | 2,40 ± 1,04 |
| 3 ova-iscom + rCTB | 3,71 ± 0,90 | 4,00 ± 0,99 | 2,72 ± 1,06 |
| 4 ova/rCTB-iscom | 3,77 ± 0,61 | 4,03 ± 0,72 | 2,25 ± 0,96 |
| 5 ova-iscom S.C. | 4,59 ± 0,36 | 4,60 ± 0,30 | 4,17 ± 0,57 |
| 6 ova + rCTB | 1,55 ± 0,16 | 1,51 ± 0,08 | <1,48 |
| 7 ova + iscom-matrix | 4,37 ± 0,11 | 4,81 ± 0,07 | <1,48 |
| 8 negative control | <1,48 | <1,48 | <1,48 |

TABLE 2

| Group | IgG | IgG1 | IgG2a |
|---|---|---|---|
| 3 ova-iscom + rCTB | 4,90 ± 0,51 | 4,54 ± 0,23 | 3,77 ± 0,77 |
| 4 ova/rCTB-iscom | 5,11 ± 0,54 | 4,74 ± 0,72 | 4,21 ± 0,80 |
| 6 ova + rCTB | 3,30 ± 0 40 | 3,19 ± 0,32 | 1,70 ± 0,18 |
| 8 negative control | <1,48 | <1,48 | <1,48 |

What is claimed is:

1. A method of eliciting an immune response in a subject, comprising administering to a mucosal organ of a subject an effective amount of an immunogenic composition for eliciting an immune response comprising at least one passenger immunogen and an immunostimulating complex, said immunostimulating complex being formed from at least one saponin and at least one lipid, said composition further comprising at least one mucosal surface targeting agent, said targeting agent being a protein, protein derivative or carbohydrate, said targeting agent being a substance that targets lymphatic tissue and induces an immune response when administered locally on mucous membrane; and wherein administration of said composition to said mucosal organ elicits an immune response not only at said mucosal organ, but also at a further mucosal organ remote from said mucosal organ to which said composition is administered.

2. The method according to claim 1, wherein the mucosal surface targeting agent has been coupled to or mixed with the immunostimulating complex.

3. The method according to claim 1, wherein said at least one lipid is a sterol or a phospholipid.

4. The method of claim 1, where the lipid is GM1 ganglioside.

5. The method according to claim 1, wherein the complex comprises at least one adjuvant in addition to the saponin.

6. The method according to claim 1, wherein the mucosal surface targeting agent is a recombinant or synthetic product.

7. The method according to claim 1, wherein the mucosal surface targeting agent is selected from the group consisting of a peptide, a polypeptide, a protein, a glycoprotein, a peptidoglycan and a lipoprotein.

8. The method according to claim 1, wherein the passenger immunogen is selected from the group consisting of a peptide, a polypeptide, a protein, a glycoprotein, a peptidoglycan, a lipoprotein, a carbohydrate and a glycolipid.

9. The method according to claim 1, wherein the mucosal surface targeting agent is obtained from a microorganism that infects at a mucosal surface.

10. The method according to claim 1, wherein the mucosal surface targeting agent is a microbial surface protein.

11. The method according to claim 1, wherein the mucosal surface targeting agent is selected from the group consisting of cholera toxin (CT), its subunit B (CTB), the heat-labile toxin of *E-coli* (LT) and its subunit B (LTB).

12. The method according to claim 1, wherein the passenger immunogen is selected from the group consisting of internal antigens of bacteria, viruses, and protozoan and metazoan parasites.

* * * * *